United States Patent
Fischell et al.

(10) Patent No.: US 12,186,189 B2
(45) Date of Patent: Jan. 7, 2025

(54) METHOD AND APPARATUS FOR ANTEGRADE TRANSCATHETER VALVE REPAIR OR IMPLANTATION

(71) Applicant: Vantis Vascular, Inc., San Jose, CA (US)

(72) Inventors: Tim A. Fischell, Kalamazoo, MI (US); Frank Saltiel, Kalamazoo, MI (US)

(73) Assignee: Vantis Vascular, Inc., San Jose, CA (US)

( * ) Notice: Subject to any disclaimer, the term of this patent is extended or adjusted under 35 U.S.C. 154(b) by 0 days.

(21) Appl. No.: 18/410,953

(22) Filed: Jan. 11, 2024

(65) Prior Publication Data

US 2024/0138982 A1   May 2, 2024

Related U.S. Application Data

(63) Continuation of application No. 18/448,888, filed on Aug. 11, 2023, now Pat. No. 11,925,554, which is a continuation of application No. 18/151,414, filed on Jan. 6, 2023, now Pat. No. 11,766,328, which is a continuation-in-part of application No. 17/962,450, filed on Oct. 7, 2022, now Pat. No. 11,759,315.

(51) Int. Cl.
*A61F 2/24*   (2006.01)

(52) U.S. Cl.
CPC .................................. *A61F 2/243* (2013.01)

(58) Field of Classification Search
CPC ... A61F 2/24; A61F 2/243; A61B 2017/00243
See application file for complete search history.

(56) References Cited

U.S. PATENT DOCUMENTS

| | | |
|---|---|---|
| 6,709,418 B1 | 2/2004 | Aboul-Hosn et al. |
| 6,814,713 B2 | 11/2004 | Aboul-Hosn et al. |
| 8,591,460 B2 | 11/2013 | Wilson et al. |
| 10,307,575 B2 | 6/2019 | Alaswad |
| 11,304,803 B2 | 4/2022 | Huber |
| 11,491,313 B2 | 11/2022 | Fischell et al. |
| 11,759,315 B1 | 9/2023 | Fischell et al. |
| 11,766,328 B1 | 9/2023 | Fischell et al. |
| 11,925,554 B1 | 3/2024 | Fischell et al. |
| 2009/0005725 A1 | 1/2009 | Shorey |
| 2009/0112050 A1 | 4/2009 | Farnan et al. |
| 2009/0149950 A1 | 6/2009 | Wampler |
| 2010/0331939 A1 | 12/2010 | Elencwajg |

(Continued)

FOREIGN PATENT DOCUMENTS

| | | |
|---|---|---|
| WO | WO2021/167653 A1 | 8/2021 |
| WO | WO2022/271999 A1 | 12/2022 |

OTHER PUBLICATIONS

Fischell et al.; U.S. Appl. No. 18/484,398 entitled "Method and apparatus for catheter-based extracorperal membrane oxygenation (ECMO)," filed Oct. 10, 2023.

(Continued)

*Primary Examiner* — Matthew W Schall
(74) *Attorney, Agent, or Firm* — Shay Glenn LLP

(57) ABSTRACT

Methods, apparatuses, and systems for performing a valve replacement or repair. Apparatuses may include systems and may include an outer catheter, one or more interchangeable inner catheters, a guidewire and an expandable chordae tendinae deflector. Also described herein are rapid pacing sheaths that may be used with any of these apparatuses and methods.

15 Claims, 35 Drawing Sheets

(56) References Cited

U.S. PATENT DOCUMENTS

| | | |
|---|---|---|
| 2011/0152741 A1 | 6/2011 | Banchieri et al. |
| 2016/0082176 A1 | 3/2016 | Kelly et al. |
| 2019/0255299 A1 | 8/2019 | Fischell et al. |
| 2019/0307996 A1 | 10/2019 | Alaswad |
| 2020/0147343 A1 | 5/2020 | Fabro |
| 2020/0179661 A1 | 6/2020 | Fischell et al. |
| 2020/0409239 A1 | 12/2020 | Ito |
| 2022/0047303 A1 | 2/2022 | Willis et al. |

OTHER PUBLICATIONS

Fischell et al.; U.S. Appl. No. 18/592,373 entitled "Method and apparatus for catheter-based extracorperal membrane oxygenation (ECMO)," filed Feb. 29, 2023.

Fischell et al.; U.S. Appl. No. 18/642,779 entitled "Method and apparatus for catheter-based extracorporeal membrane oxygenation (ECMO)," filed Apr. 22, 2024.

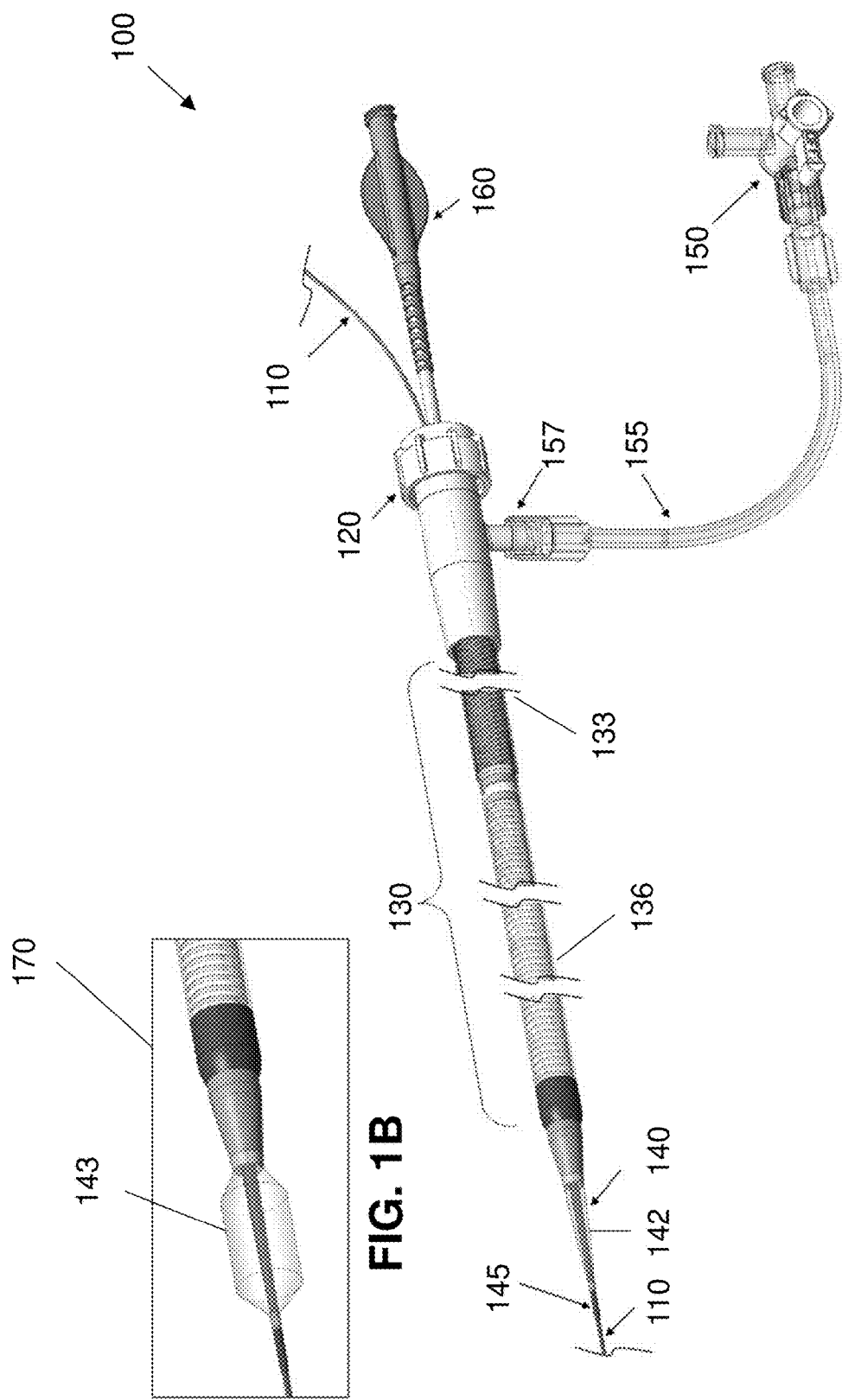

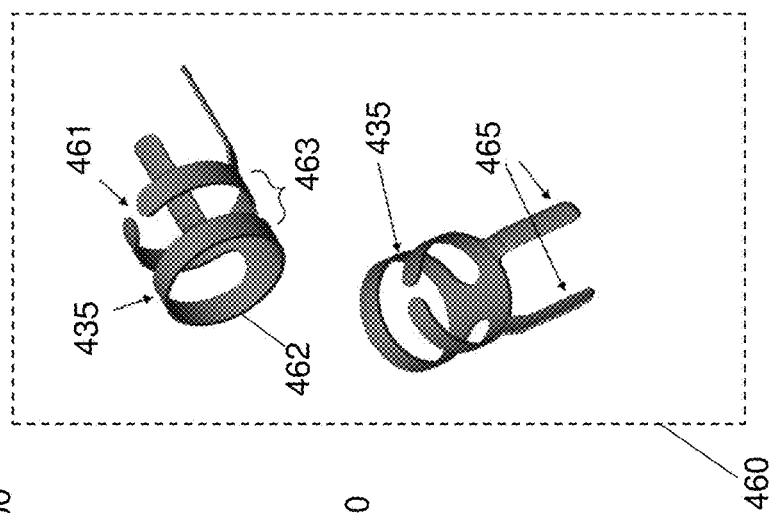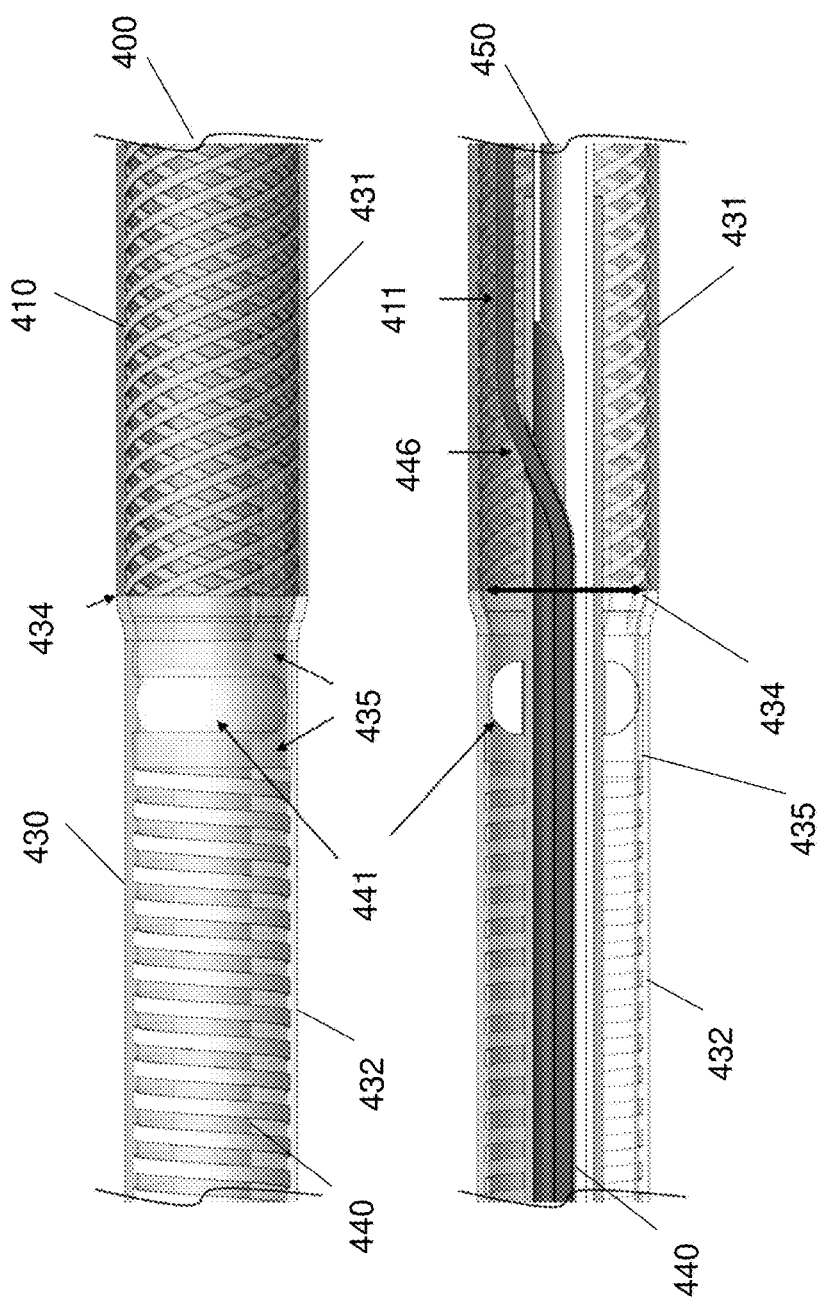

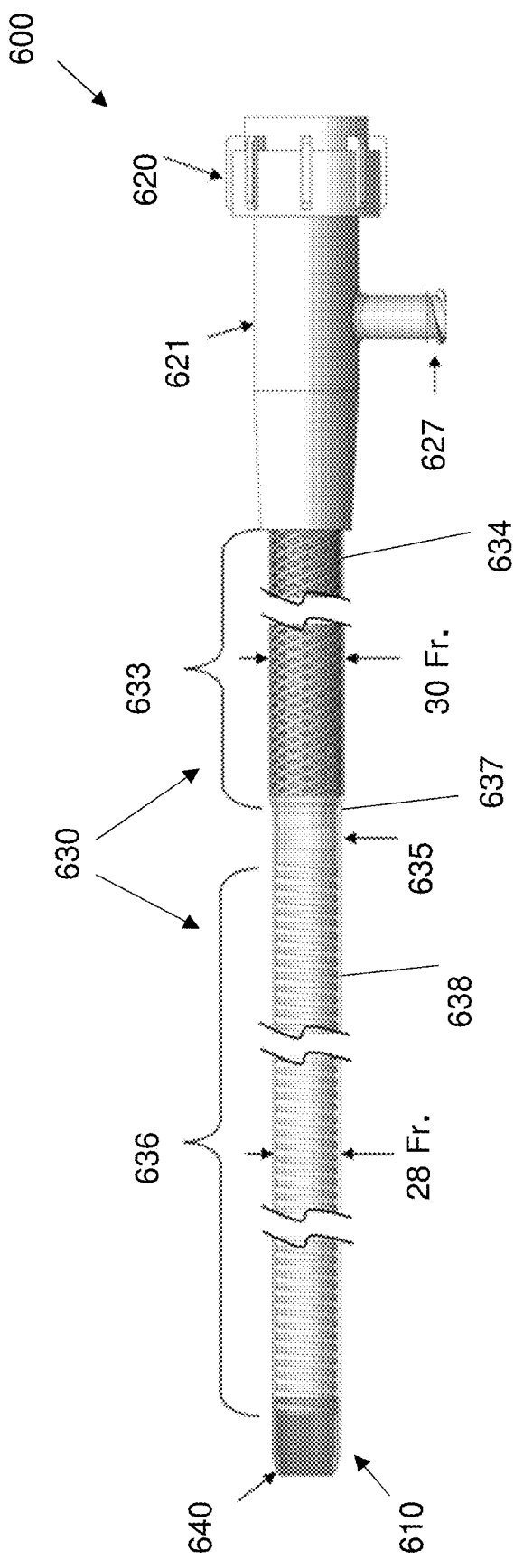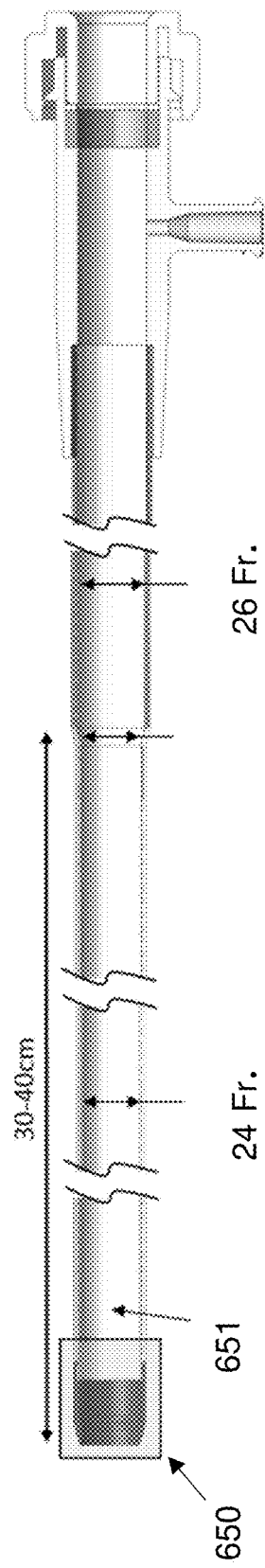
FIG. 6A
FIG. 6B

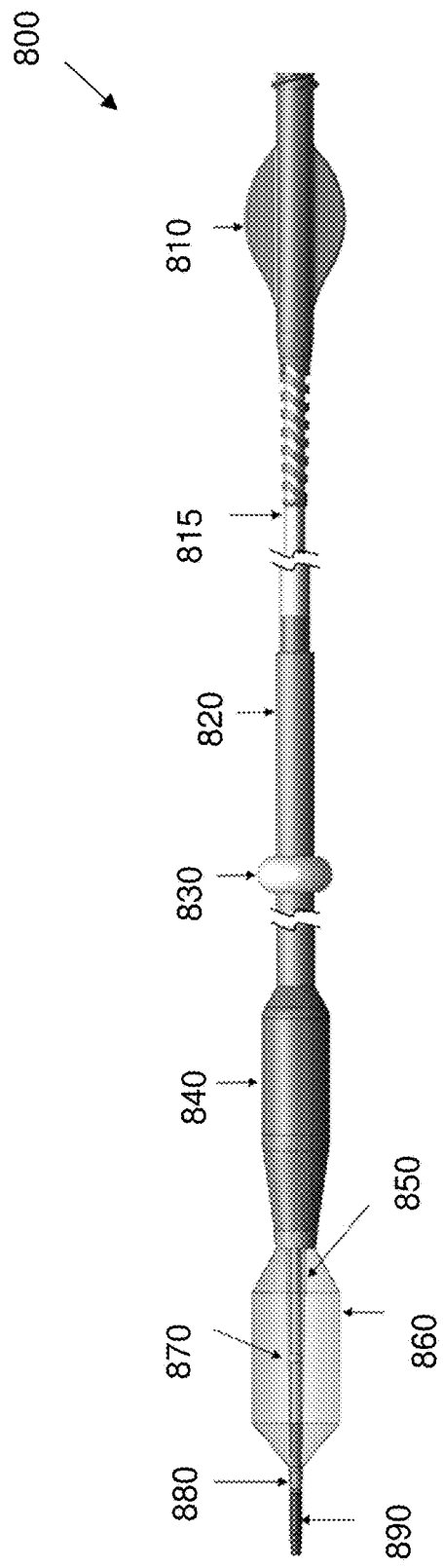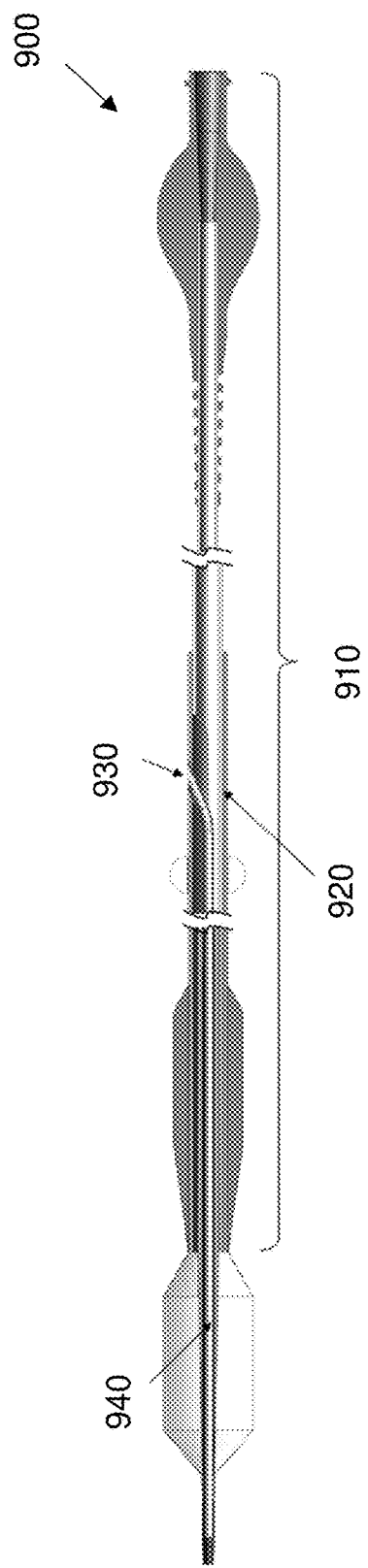
FIG. 8
FIG. 9

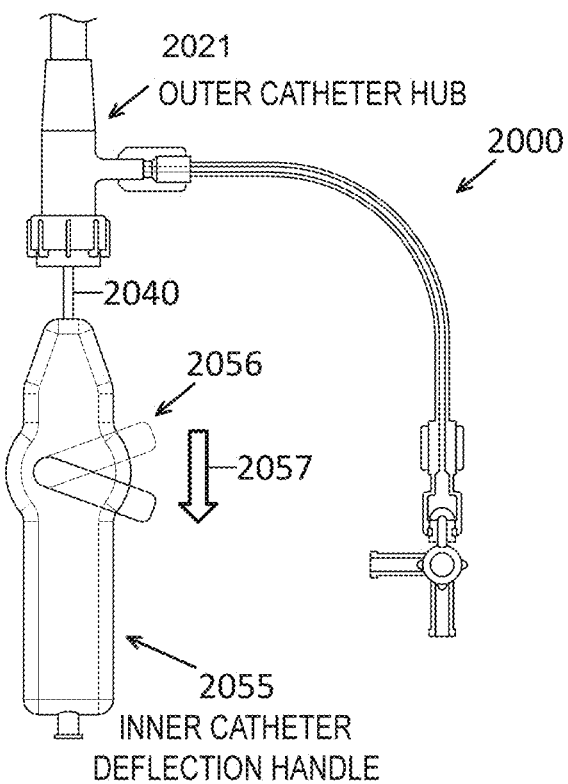
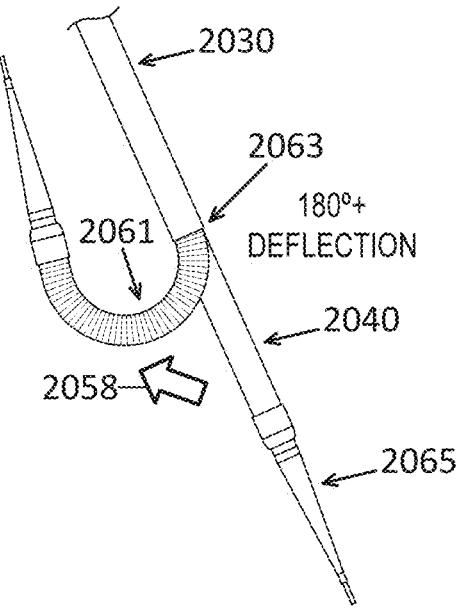
FIG. 20A  FIG. 20B
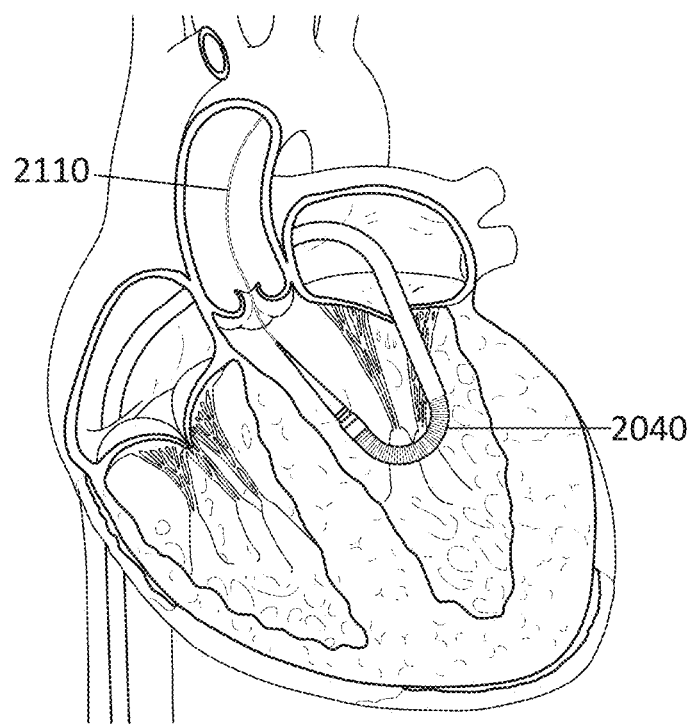
FIG. 21

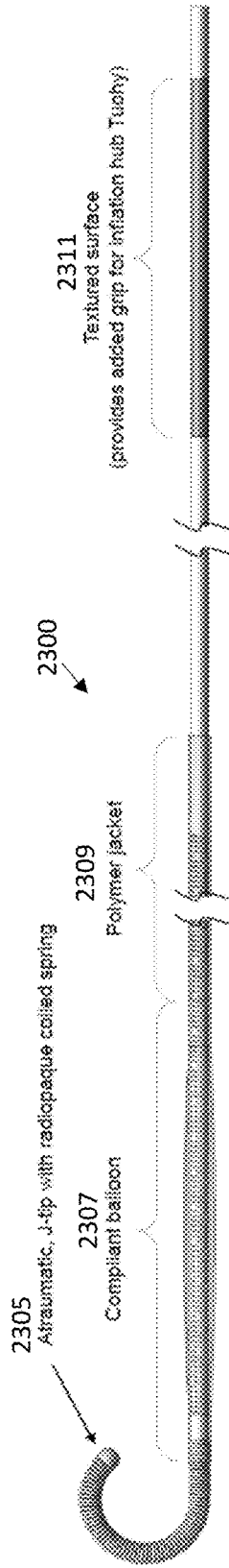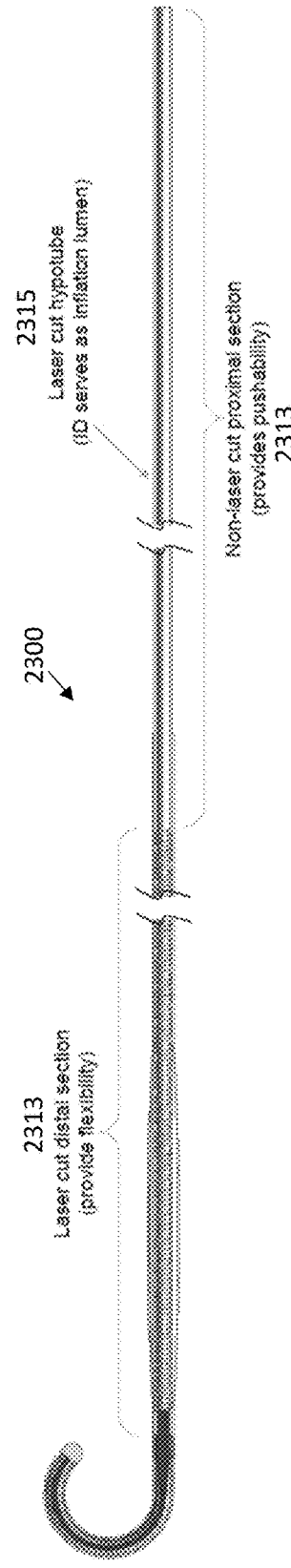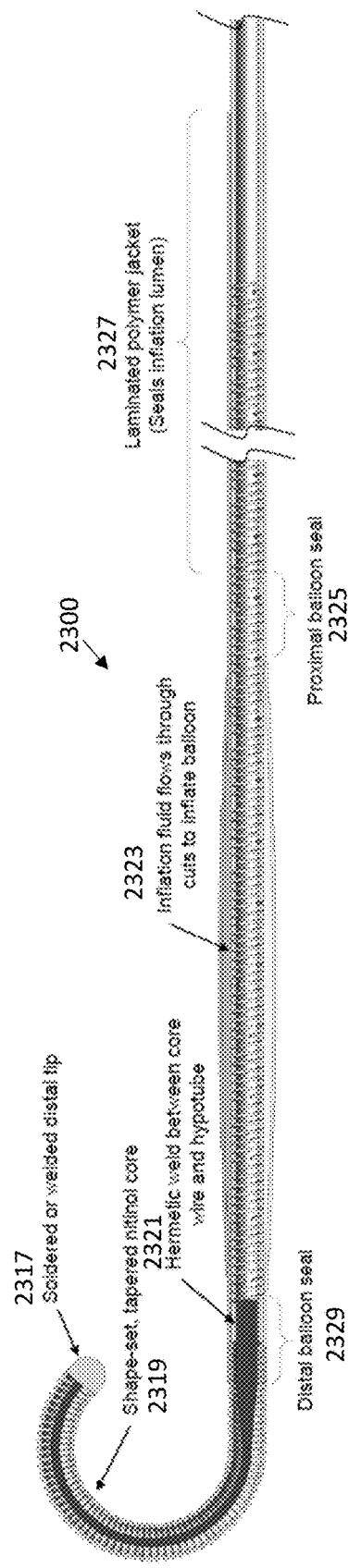

METHOD AND APPARATUS FOR ANTEGRADE TRANSCATHETER VALVE REPAIR OR IMPLANTATION

CLAIM OF PRIORITY

This patent application is a continuation of U.S. patent application Ser. No. 18/448,888, filed Aug. 11, 2023, which is a continuation of U.S. patent application Ser. No. 18/151,414, filed Jan. 6, 2023, now U.S. Pat. No. 11,766,328, which claims priority as a continuation-in-part to U.S. patent application Ser. No. 17/962,450, filed Oct. 7, 2022, now U.S. Pat. No. 11,759,315, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The methods and apparatuses described herein may be related to transcatheter aortic valve implantation procedures. More specifically, the methods and apparatuses described herein may relate to apparatuses that may enable a surgeon to implant an aortic valve into a patient's heart using an antegrade approach to the aorta.

BACKGROUND

Heart valve surgeries may encompass a variety of surgical approaches used to repair or replace diseased heart valves. Some heart valve surgeries may be open-heart procedures conducted under general anesthesia. An incision is made through the patient's sternum (sternotomy), and the patient's heart is stopped while blood flow is rerouted through a heart-lung bypass machine. This valve replacement surgery is a highly invasive procedure and is associated significant attendant risks and complications.

Transcatheter aortic valve replacement (TAVR) is one alternative to an open-heart surgical aortic valve replacement. The aortic valve is located between the left ventricle and the aorta. If the aortic valve does not operate correctly, blood flow from the heart to the body may be impaired. In this procedure, a collapsed replacement aortic valve is delivered to the implantation site through a catheter. The catheter is typically inserted into a patient's artery through an incision away from the heart. Using the catheter, a surgeon guides the replacement valve into place, in a retrograde approach. After confirming the position of the replacement valve, the surgeon implants the valve using the catheter.

Retrograde TAVR procedures (e.g., advancing the catheter in a direction opposite to or opposing blood flow) are often used because of a much simpler pathway for the catheter to approach the aortic valve. However, retrograde approaches may be associated with negative outcomes, such as major bleeding at the arterial access site or stroke from embolic debris from the aorta, particularly when the patient's aortic valve suffers from stenosis and/or may include calcification or other deposits. Antegrade TAVR procedures (e.g., advancing the catheter in the direction of blood flow) via a transseptal approach may overcome some of the disadvantages associated with retrograde TAVR procedures, by using venous access to reduce bleeding, and eliminating trauma to the aortic arch, to reduce stroke. Unfortunately, antegrade TAVR procedures have historically been more difficult to perform. Difficulties include a need for an atrial septal crossing, possible damage to the mitral valve, and problems related to delivering a large-profile implantation device through the left atrium to the left ventricle and the aortic valve. These challenges have caused antegrade TAVR procedures to be largely supplanted by other approaches.

Thus, there has been a long felt need for a method and apparatus of performing successful antegrade TAVR procedures.

SUMMARY OF THE DISCLOSURE

Described herein are apparatuses, systems, and methods to perform an antegrade aortic valve replacement. Example apparatuses (which may include systems, system devices, and/or software) may include an outer catheter, an inner catheter (or multiple interchangeable inner catheters) and a guidewire. Any of the inner catheters may be detachably coupled to the outer catheter. The inner catheter and outer catheter may surround the guidewire such that the inner and outer catheters may be advanced in a monorail fashion within the patient.

Any of the apparatuses and methods described herein may be configured to pass safely through the mitral valve without engaging the interstices of the chordae tendinae. For example, any of these methods and apparatuses may include an expandable deflector (e.g., an expandable balloon, cage, mesh, plurality of struts, etc.) that may be expanded to pass through the mitral valve orifice without engagement of the chordae tendinae within the left ventricle. In any of these methods and apparatuses the deflector may deflect the device away from the chordae tendinae.

Any of these apparatuses and methods described herein may include a rapid pacing sheath that is configured to apply a heart pacing stimulation during the procedure to allow pacing for bradycardia and/or rapid pacing to allow safe aortic valve deployment. Thus, these apparatuses may be configured to apply rapid pacing or escape pacing.

In general, these apparatuses (e.g., systems) are configured to navigate the venous vasculature cardiac anatomy for antegrade delivery of a heart valve (e.g., an aortic valve, a mitral valve, etc.). By utilizing a venous delivery these apparatuses are configured to prevent scraping of the aortic and arterial vasculature which may cause complications when repairing a heart valve from the retrograde direction, as this may release material (including clot and/or atherosclerotic material) may result in complications. Thus, these apparatuses may generally include an outer catheter having a distal end region that sealingly and releasably mates with a slightly proximal region of the inner catheter(s) to prevent any gaps between the two when engaged. The outer and/or inner catheter(s) may also be configured to be bent or steered from a region that is proximal to the distal end. The inner catheter(s) may include a steerable, pre-bent, and/or bendable (deflectable) region that is positioned between a tapered distal end region and a more proximal sealing region that engages the inner catheter with the distal end of the outer catheter. This steerable, pre-bent and/or bendable region may be configured to provide a very sharp bend (e.g., between about 30 and about 180 degrees of deflection (e.g., between about 40-180 degrees, between about 60-180, between about 80-180, between about 90-180 degrees, between about 100-180 degrees, between about 110-180 degrees, between about 120-180 degrees, greater than 120 degrees, etc.). In addition, the outer catheter may be particularly flexible and thin-walled, to allow it to track over the curves or bends formed by the inner catheter and track over the guidewire.

For example, a system for antegrade delivery of a replacement valve (e.g., aortic valve) that may include an outer catheter and an inner catheter comprising: a distal end region that is tapered, an engagement surface proximal to a distal end of the inner catheter, wherein the engagement surface is configured to detachably couple to a distal end region of the outer catheter so that an outer surface of the first inner catheter is flush with an outer surface of the outer catheter without a gap, and a bend region between the engagement surface and the distal end that is configured to assume a bend of greater than 120 degrees.

For example, a system for antegrade delivery of a replacement mitral valve may include an outer catheter and an inner catheter comprising: a distal end region that is tapered, an engagement surface proximal to a distal end of the inner catheter, wherein the engagement surface is configured to detachably couple to a distal end region of the outer catheter so that an outer surface of the first inner catheter is flush with an outer surface of the outer catheter without a gap, and a bend region between the engagement surface and the distal end that is configured to assume a bend of greater between about 60 and 120 degrees.

Any of these apparatuses and methods may be configured for repair of a valve, not limited to replacement of the valve. For example, any of these methods may be for insertion of repair tools, implants, etc. In general, the same apparatuses and procedures for using them described herein for valve replacement may be used for access and repair.

The distal end region may taper from a large proximal opening to a narrow distal opening (e.g., may taper from about 3 Fr or smaller to about 14 Fr or larger, e.g., 20 Fr or larger, etc.).

As mentioned, the outer catheter may comprise a thin-walled flexible outer layer of 14 Fr or larger that is configured to track with the inner catheter when the inner catheter is in a bent configuration. The outer catheter may comprise a pre-bent distal region. In some examples the outer catheter may be bendable.

The inner catheter may be steerable (e.g., controllably bendable/deflectable). For example in some examples the inner catheter includes a tendon or wire (e.g., pull wire) configured to bend the bend region. The wire may be attached at the distal end of the bending distal region. The distal region may include flexures (e.g., cut-outs, creases, etc.) to provide a predictable bending region. In any of these examples the bend region may comprise a bend setting material, such as a shape memory material (e.g., a nickel titanium alloy) that is configured to assume a bend. The bend region may be manually bent (shape set) prior to use to assume a bend once deployed out of the outer catheter and into the vasculature. This bendable inner catheter may impart a major bend to the distal portion of the flexible outer catheter to allow the relatively large outer catheter to track through the mitral valve, and or around the left ventricle to the left ventricular outflow track.

Any of the apparatuses described herein may include a second inner catheter comprising: a distal end region that is tapered, an engagement surface proximal to a distal end of the inner catheter, wherein the engagement surface is configured to detachably couple to a distal end region of the outer catheter so that an outer surface of the first inner catheter is flush with an outer surface of the outer catheter without a gap, and a bend region between the engagement surface and the distal end that is configured to assume a bend of greater than 30 degrees. Thus, the second (or subsequent) inner catheter may be similar to the first inner catheter but may have a different bend angle or range of bend angles.

In any of the systems described herein the inner catheter may have a bend region that is between about 3-10 mm from the distal tip of the inner catheter. As mentioned, this bend region may be between the tapered distal tip region and a proximal region that engages with the outer catheter.

In general, the inner catheter(s) may include a rapid exchange monorail connection for a guidewire. This may allow the inner catheters to be rapidly exchanged within the outer catheters. In some examples the outer catheter does not include a rapid exchange monorail but may be enclosed along its entire length. Any of these systems may include one or more guidewires, e.g., a first guidewire and a second guidewire, wherein the first guidewire is stiffer than the second guidewire. It may also include a guidewire with side-holes to allow contrast injection in the proximal aorta to allow more precise valve positioning. In general, these apparatuses may include one or more hemostasis valve that is coupled to or configured to couple to the outer catheter.

The inner catheter may have a decreasing stiffness along the distal end region. In general, the distal end may be significantly more flexible than the proximal end.

In any of these apparatuses, the inner catheter may comprise a dilation balloon disposed near a distal end region of the inner catheter. For example, the dilation balloon may be configured to open and or widen an opening through the septum or other anatomic region.

The inner catheter may include a skived hypotube configured to have a decreasing stiffness in a distal direction. In any of these apparatuses, the inner catheter may include a first section and a second section, and wherein the first section includes a braid configured to provide kink resistance and resistance to torsion and the second section includes a spiral coil configured to provide less stiffness than the braid. The first section may be configured to have an outer diameter of approximately 25 French (Fr.) (e.g., between 14 Fr and 35 Fr, between 20 Fr and 30 Fr, between 22 Fr, and 28 Fr, between 22 Fr and 30 Fr, etc.) and the second section may be configured to have an outer diameter of approximately 23 Fr (e.g., between 1-5 Fr smaller than the first section, etc.). For example, the first section may be configured to have an inner diameter of approximately 24 Fr. and the second section is configured to have an inner diameter of approximately 22 Fr. As TAVR valve technology provides smaller delivery diameters, smaller sheaths can be used. The outer catheter may include a coupler configured to engage with a lock ring disposed on the first inner catheter.

Also described herein are methods for percutaneous antegrade delivery and insertion (implantation) of a valve, such as an aortic valve. These methods may use any of the systems described herein. For example, a method for percutaneous antegrade delivery and implantation of a valve in a patient may include: advancing a first inner catheter that is distally tapered through a transseptal puncture, wherein a region of the first inner catheter proximal to a distal end of the first inner catheter is annularly engaged to an outer catheter at a distal end region of the outer catheter so that an outer surface of the first inner catheter is flush with an outer surface of the outer catheter without a gap; deflecting the first inner catheter within the left atrium so that a distal end region of the first inner catheter assumes a first bend; advancing the outer catheter and either the first inner catheter or a second inner catheter that has been exchanged for the first inner catheter so that the first or second inner catheter is in the left ventricle; advancing a guidewire out of the distal end of the first or second inner catheter and across a valve of the patient's heart; removing the first or second inner catheter, leaving the wire in place, and implanting a replacement valve in the patient's heart through the outer catheter.

In any of these methods, after advancing the guidewire out of the distal end of the first or second inner catheter, the first or second inner catheter within the left ventricle may be deflected so that the distal end region of the first or second inner catheter assumes a second bend and faces the patient's left ventricular outflow tract. Implanting the replacement valve may include implanting an aortic valve. For example, implanting the replacement valve may comprise implanting a mitral valve.

For example, a method for percutaneous antegrade delivery and implantation of a valve in a patient may include: advancing a first inner catheter that is distally tapered through a trans-septal puncture, wherein a region of the first inner catheter proximal to a distal end of the first inner catheter is annularly engaged to an outer catheter at a distal end region of the outer catheter so that an outer surface of the first inner catheter is flush with an outer surface of the outer catheter without a gap; deflecting the first inner catheter within the left atrium so that a distal end region of the inner catheter assumes a first bend; advancing the outer catheter and either the first inner catheter or a second inner catheter that has been exchanged for the first inner catheter so that the first or second inner catheter is in the left ventricle; deflecting the first or second inner catheter within the left ventricle so that the distal end region of the first or second inner catheter assumes a second bend turns towards the left ventricular outflow tract; advancing a guidewire out of the distal end of the first or second inner catheter and across an aortic valve of the patient's heart; removing the first or second inner catheter, leaving the wire in place, and implanting a replacement aortic valve in the patient's heart through the outer catheter.

Any of these methods may include advancing the outer catheter and the first or second inner catheter so that the first or second inner catheter passes through an aortic valve of the patient's heart and at least partially into the ascending aorta over a guidewire. Implanting the replacement aortic valve in the patient's heart may include implanting the replacement valve through the outer catheter and over the guidewire. If the aortic valve is delivered with the outer catheter across the aortic valve the outer catheter would be withdrawn in a proximal direction to "unsheathe" the valve prior to valve deployment.

Any of these methods may include advancing a second guidewire into the left ventricle after the first inner catheter has assumed the first bend. Implanting the replacement aortic valve may include advancing a transcatheter aortic valve replacement (TAVR) delivery system through the outer catheter.

In some examples the method may include expanding the trans-septal puncture with an expandable member on an outer surface of the first inner catheter. For example, the expandable member may comprise a balloon.

The first bend (e.g., of the inner catheter) may be at least about 30 degrees (e.g., between about 30-100 degrees, between about 30-90 degrees, between about 30-80 degrees, between about 30-70 degrees, between about 30-60 degrees, between about 3-45 degrees, etc.). The second bend may be at least about 120 degrees (e.g., between about 120-190 degrees, between about 120-180 degrees, between about 120-170 degrees, between about 120-160 degrees, between about 120-150 degrees, between about 120-140 degrees, etc.). Deflecting the first inner catheter may include actuating a pull wire within the first inner catheter to deflect the bending region of the inner catheter. In some examples deflecting the first inner catheter may include allowing the first inner catheter to assume a bent configuration (e.g., extending the inner catheter from out of the outer catheter, removing a stiffening member etc.).

As mentioned, the first inner catheter may be distally tapered from 3 Fr or smaller to 14 Fr or larger. This taper may prevent or reduce damage to the tissue in combination with the engagement region between the inner and outer catheter, preventing fish-mouthing (e.g., separation between the inner and outer catheters at the distal connection between the two, even while navigating through bent regions).

Any of these methods may include manually setting the first bend and/or the second bend prior to advancing the distally first inner catheter through the transseptal puncture.

The methods described herein may include advancing a distally tapered initial inner catheter through the transseptal puncture before advancing the first inner catheter, wherein the initial inner catheter is annularly engaged to the outer catheter at a distal end region of the outer catheter, so that the outer catheter passes through the transseptal puncture and into a left atrium.

In any of the methods described herein the method may use a single inner catheter and a single outer catheter. In some examples (as described above) a single outer catheter may be used with two or more inner catheters. For example, described herein are methods for percutaneous antegrade delivery and implantation of an aortic valve in a patient that include: advancing an inner catheter that is distally tapered through a transseptal puncture, wherein a region of the inner catheter proximal to a distal end of the inner catheter is annularly engaged to an outer catheter at a distal end region of the outer catheter so that an outer surface of the inner catheter is flush with an outer surface of the outer catheter without a gap; deflecting the inner catheter within the left atrium so that a distal end region of the inner catheter assumes a first bend; advancing the outer catheter and the inner catheter so that the inner catheter is in the left ventricle; deflecting the inner catheter within the left ventricle so that the distal end region of the inner catheter assumes a second bend and the distal end region is bent in a way to direct the catheter system into the left ventricular outflow tract; advancing a guidewire out of the distal end of the inner catheter and across an aortic valve of the patient's heart; removing the first or second inner catheter, leaving the wire in place, and implanting a replacement aortic valve in the patient's heart through the outer catheter.

Any of these methods may include advancing the outer catheter and the inner catheter so that the inner catheter passes through an aortic valve of the patient's heart and at least partially into the ascending aorta over a guidewire.

In general, implanting the replacement aortic valve in the patient's heart may include implanting the replacement valve through the outer catheter and over the guidewire.

Any of these methods may include advancing a second guidewire into the left ventricle after the inner catheter has assumed the first bend.

For example, implanting the replacement aortic valve comprises advancing a transcatheter aortic valve replacement (TAVR) delivery system through the outer catheter.

As mentioned, the methods described herein may include expanding the transseptal puncture with an expandable member on an outer surface of the inner catheter. The first bend may be at least about 30 degrees (e.g., between about 30-100 degrees, between about 30-90 degrees, between about 30-80 degrees, between about 30-70 degrees, between about 30-60 degrees, between about 3-45 degrees, etc.). The second bend may be at least about 120 degrees (e.g., between about 120-190 degrees, between about 120-180 degrees, between about 120-170 degrees, between about 120-160 degrees, between about 120-150 degrees, between about 120-140 degrees, etc.).

As mentioned above, deflecting the inner catheter may include actuating a pull wire within the inner catheter. In some examples, deflecting the inner catheter comprises allowing the inner catheter to assume a bent configuration. The inner catheter may be distally tapered from 3 Fr or smaller to 14 Fr or larger. Any of these methods may include manually setting the first bend and/or the second bend prior to advancing the distally inner catheter through the transseptal puncture.

The methods described herein may include advancing a distally tapered initial inner catheter through the transseptal puncture before advancing the inner catheter, wherein the initial inner catheter is annularly engaged to the outer catheter at a distal end region of the outer catheter, so that the outer catheter passes through the transseptal puncture and into a left atrium.

As mentioned in some examples these methods may include the use of a single outer catheter and two (or more) inner catheters that may be swapped (including by rapid exchange) at different points during the procedure. For example, a method for percutaneous antegrade delivery and implantation of an aortic valve in a patient may include: advancing a first inner catheter that is distally tapered through a transseptal puncture, wherein a region of the first inner catheter proximal to a distal end of the first inner catheter is annularly engaged to an outer catheter at a distal end region of the outer catheter so that an outer surface of the first inner catheter is flush with an outer surface of the outer catheter without a gap; deflecting the first inner catheter within the left atrium so that a distal end region of the first inner catheter assumes a first bend; advancing the outer catheter and the first inner catheter so that the first inner catheter is in the left ventricle; withdrawing the first inner catheter proximally from the outer catheter and inserting a second inner catheter through the outer catheter and into the left ventricle so that a region of the second inner catheter proximal to a distal end of the second inner catheter is annularly engaged to the outer catheter at the distal end region of the outer catheter; deflecting the second inner catheter so that a distal end region of the second inner catheter assumes a second bend that is greater than the first bend and a distal end of the second inner catheter is bent in a manner to allow passage of the catheter system into the left ventricular outflow tract; advancing a guidewire out of the distal end of the second inner catheter and across an aortic valve of the patient's heart; removing the first or second inner catheter, leaving the wire in place, and implanting a replacement aortic valve in the patient's heart through the outer catheter.

The methods described herein may include advancing the second outer catheter and the inner catheter so that the second inner catheter passes through an aortic valve of the patient's heart and at least partially into the ascending aorta before advancing the guidewire. Implanting the replacement aortic valve in the patient's heart may comprise implanting the replacement valve through the outer catheter and over the guidewire.

Any of these methods may include advancing a guidewire into the left ventricle after the first inner catheter has assumed the first bend. In some examples, implanting the replacement aortic valve comprises advancing a transcatheter aortic valve replacement (TAVR) delivery system through the outer catheter. Any of these methods may include expanding the transseptal puncture with an expandable member on an outer surface of the first inner catheter. As described above, the expandable member may comprise a balloon. Also, as described above, the first bend may be at least about 30 degrees and the second bend may be at least about 120 degrees. Deflecting the first inner catheter may comprise actuating a pull wire within the first inner catheter. In some examples deflecting the first inner catheter comprises allowing the first inner catheter to assume a bent configuration. The first inner catheter may be distally tapered from 3 Fr or smaller to 14 Fr or larger, as described above. Any of these methods may include manually setting the first bend and/or the second bend prior to advancing the distally first inner catheter through the transseptal puncture.

In some examples the method includes advancing a distally tapered initial inner catheter through the transseptal puncture before advancing the first inner catheter, wherein the initial inner catheter is annularly engaged to the outer catheter at a distal end region of the outer catheter, so that the outer catheter passes through the transseptal puncture and into a left atrium.

As described herein, any of the catheters may have a varying stiffness. For example, the stiffness of the outer catheter and any of the inner catheters may decrease as the catheter extends away from a surgeon or other user. In some examples, any of the catheters may include a braided liner, a spiral liner, or a combination thereof to change and/or control the stiffness of the catheter.

Any of the interchangeable inner catheters may include differently shaped distal tips that may be used to position and/or guide the guidewire within the patient. Alternatively, or in addition, any of the interchangeable inner catheters may include a distally located dilation balloon.

In any of the methods described herein, the inner and outer catheters may be percutaneously introduced to the patient. The apparatus may puncture and cross the atrial septum. A catheter may be advanced from the left atrium, into the left ventricle, and antegrade toward the aortic valve. From this position, a replacement aortic valve may be implanted.

Any of the methods described herein may perform a percutaneous antegrade delivery and implantation of an aortic valve. Any of the methods may include puncturing, using a guidewire, an atrial septum of a patient's heart, advancing a catheter across the atrial septum into a left atrium of the patient's heart and advancing the catheter from the left atrium to a left ventricle. Further, any of the methods described herein may include advancing, with the catheter, the guidewire through an aortic valve of the patient's heart, positioning the catheter across an annulus of the aortic valve, and implanting a replacement aortic valve within the patient's heart.

In any of the methods described herein, the puncturing may include using a radio-frequency device disposed on a distal end of the guidewire. Any of the methods described herein may also include entering a femoral artery with the catheter and the guidewire prior to puncturing the atrial septum.

In any of the methods, the catheter may include a first inner catheter and an outer catheter, wherein the first inner catheter is concentric and detachably coupled to the outer catheter. Furthermore, the guidewire may be concentric to, and enclosed by, the first inner catheter and the outer catheter.

In any of the methods described herein, advancing the catheter from the left atrium to the left ventricle may include advancing the guidewire through a mitral valve of the patient's heart. In some examples, advancing the catheter from the left atrium to the left ventricle may include replacing the first inner catheter with a second inner catheter having a curved distal tip, advancing the guidewire through the second inner catheter with the curved distal tip, through a mitral valve, and into the left ventricle, and withdrawing the second inner catheter from the outer catheter. In some aspects, the curved distal trip may have a curve of at least 30 degrees.

In any of the methods described herein, advancing the guidewire through the aortic valve may include using a third inner catheter having an acute angle curve distal tip having a curve of at least 120 degrees. Furthermore, positioning the catheter across the annulus of the aortic valve further may include withdrawing the third inner catheter.

In any of the methods described herein, advancing the guidewire through the aortic valve may include advancing the guidewire in an antegrade direction into an aorta of the patient's heart. In any of the methods, positioning the catheter across the annulus of the aortic valve may include positioning a distal tip of the outer catheter below the annulus of the aortic valve.

In any of the methods described herein, advancing the catheter across the atrial septum may further include advancing a dilation balloon into the atrial septum. In any of the methods described herein, advancing the catheter across the atrial septum further may include advancing a dilation balloon into the atrial septum. In addition, any of the methods may include inflating the dilation balloon to expand a puncture of the atrial septum; deflating the dilation balloon; and withdrawing the dilation balloon. In any of the methods described herein, the dilation balloon may be coupled to the catheter.

In any of the apparatuses described herein, the outer catheter may include a coupler configured to engage with a lock ring disposed on the first interchangeable inner catheter. Any of the apparatuses may further include a second interchangeable inner catheter configured to bend at least 30 degrees. Any of the apparatuses described herein may further include a third interchangeable catheter configured to bend at least 120 degrees. In any of the apparatuses described herein, the first interchangeable inner catheter and the outer catheter may include radiopaque markers.

The methods and apparatuses described herein may also or additionally include a filter for capturing material during valve positioning and deployment. The filter may be an expandable filter that may be attached or affixed to a wire, such as a guidewire. Thus, any of the guidewires described herein may include a filter ("filter wire"). The filter may be held collapsed by a sleeve that may be retracted proximally. The filter may be deployed from a wire, such as the guidewire, that is extended distally antegrade beyond the valve being replaced or repaired. For example, in some variations, the method may include advancing the guidewire out of the distal end of the first or second inner catheter and across an aortic valve of the patient's heart, and the guidewire may include a filter. Thus, any of these methods may include deploying a filter attached to the guidewire distally of the aortic valve.

Also described herein are guidewires that are configured to deliver contrast material from one or more side ports. These guidewires may be used in place of any of the guidewires described herein (including for use with a filter as mentioned above). The guidewire may include an array of side-facing ports or openings into a central lumen through which contrast material may be injected. These guidewires may be referred to herein as contrast-deploying guidewires. A contrast-deploying guidewire may have a solid distal tip/distal end region and may be hollow along the length of the contrast-deploying guidewire proximal to the distal tip region. The distal tip region of the contrast-deploying guidewire may extend any appropriate length (e.g., about 0.5 cm or less, about 1 cm or less, about 2 cm or less, about 3 cm or less, about 4 cm or less, about 5 cm or less, between about 0.5-10 cm, between about 1-8 cm, between 0.5-7 cm, between about 0.5-6 cm, between about 0.5-5 cm, etc.). Any number of side-opening ports or holes may be used and may be arranged down the length of the contrast-deploying guidewire. In some examples the ports or holes may be arranged on the same side of the contrast-deploying guidewire; in some examples the ports or holes may be distributed around the width of the contrast-deploying guidewire. For example, any of the methods described herein may include delivering a contrast material out of one or more side-facing ports of the guidewire.

As mentioned above, any of the methods and apparatuses described herein may include a deflector for deflecting chordae tendinae of the ventricle during a procedure. For example, described herein are methods method for percutaneous antegrade delivery and implantation of a valve in a patient comprising: advancing a first inner catheter that is distally tapered into a left atrium through a transseptal puncture, wherein a distal region of the first inner catheter is flush with an outer catheter at a distal end region of the outer catheter; expanding an expandable deflector to allow safe passage through the mitral valve without engagement of the chordae tendinae of the left ventricle; advancing the outer catheter and either the first inner catheter or a second inner catheter that has been exchanged for the first inner catheter, so that the first or second inner catheter is in a left ventricle while deflecting away from the chordae tendinae; advancing a guidewire out of the distal end of the first or second inner catheter and across a valve of the patient's heart; removing the first or second inner catheter, leaving the guidewire in place, and implanting a replacement valve in the patient's heart through the outer catheter.

For example, a method for percutaneous antegrade delivery and implantation of a valve in a patient may include: advancing a first inner catheter that is distally tapered through a transseptal puncture, wherein a region of the first inner catheter proximal to a distal end of the first inner catheter is annularly engaged to an outer catheter at a distal end region of the outer catheter so that an outer surface of the first inner catheter is flush with an outer surface of the outer catheter without a gap; deflecting the first inner catheter within the left atrium so that a distal end region of the inner catheter assumes a first bend; expanding an expandable deflector to deflect away from the chordae tendinae of the left ventricle; advancing the outer catheter and either the first inner catheter or the second inner catheter that has been exchanged for the first inner catheter so that the first or second inner catheter is in the left ventricle while deflecting away from the chordae tendinae; deflecting the first or second inner catheter within the left ventricle so that the distal end region of the first or second inner catheter assumes a second bend and faces the patient's left ventricular outflow tract; advancing a guidewire out of the distal end of the first or second inner catheter and across an aortic valve of the patient's heart; removing the first or second inner catheter, leaving the wire in place, and implanting a replacement aortic valve in the patient's heart through the outer catheter.

Any of these methods may include deflecting the first inner catheter within the left atrium so that a distal end region of the first inner catheter assumes a first bend.

Expanding the expandable deflector may include expanding the expandable deflector on a guidewire extending through the first inner catheter or a second inner catheter that has been exchanged for the first inner catheter. In some examples expanding the expandable deflector comprises expanding the expandable deflector on the first inner catheter or the second inner catheter that has been exchanged for the first inner catheter. Expanding the expandable deflector may include expanding the expandable deflector on the second inner catheter that has been exchanged for the first inner catheter.

Any of these methods may include, after advancing the guidewire out of the distal end of the first or second inner catheter: deflecting the first or second inner catheter within the left ventricle so that the distal end region of the first or second inner catheter assumes a second bend and faces the patient's left ventricular outflow tract. For example, the method may include deflecting away from the chordae tendinae of the left ventricle with the expandable deflector as the distal end region of the first or second inner catheter assumes the second bend. In any of these methods, advancing the outer catheter and either the first inner catheter or the second inner catheter may include advancing with the expandable deflector expanded.

An expandable deflector may be any appropriate deflector, including inflatable deflector (e.g., balloons), mechanical deflectors (e.g., struts, cages, mesh, etc.), or the like. For example, expanding the expandable deflector comprises expanding a balloon. These methods and apparatuses may include one or more expandable deflectors. For example, the expandable deflector may be on the inner catheter, the outer catheter and/or a guidewire (or, more generally, a guide element). As used herein a guide wire may include a wire, thin guide tube or catheter, etc.

The expandable deflector may expand fully or partially and/or may be expanded to a diameter that is appropriate for the anatomy (e.g., the ventricle), such as to between about 1 cm and 5 cm. The mechanical deflector may have a rounded and/or smooth outer profile, which may help avoid entrapment between the chordae tendinae and/or trauma to the interior of the ventricle. For example the expandable deflector may include an outer surface, which may be configured as a cover or sleeve. In some cases the expandable deflector may include mechanical ribs or struts that may be covered by an elastic or elastomeric layer.

The expandable deflector may be expanded in in the ventricle (e.g., in the left ventricle), including (but not limited to) expanding the expandable deflector at the mitral orifice, e.g., prior to or just after inserting through the mitral orifice/mitral valve.

As mentioned above, any of these methods may include applying electrical pacing to the patient's heart during the procedures described herein. In any of these methods and apparatuses the outer catheter may be configured as a sheath (e.g., a pacing sheath), including a plurality of electrodes. For example, any of these methods may include applying a pacing signal to the patient's heart from electrodes on the outer catheter (sheath) through which the inner catheter is inserted.

In any of these methods and apparatuses, implanting the replacement aortic valve may include advancing a transcatheter aortic valve replacement (TAVR) delivery system through the outer catheter.

Also described herein are system for antegrade delivery of a replacement valve that may be used in any of the methods described herein. For example, any of these apparatuses and methods may include an outer catheter configured as a sheath to receive the inner catheter, the outer catheter (sheath) comprising: an elongate body having a lumen configured to receive the inner catheter, wherein the elongate body is configured to extend from outside of a body to a left ventricular apex of the heart; a hub at a proximal end of the elongate body, the hub comprising a hemostatic valve; a plurality of electrodes at a distal end region of the elongate body; a plurality of electrical connectors extending proximally from the elongate body; and a plurality of conductor cables (which may form a bundle) extending from the plurality of electrical connectors to the plurality of electrodes, so that each electrical connector electrically connects to a corresponding electrode of the plurality of electrodes.

Thus, any of these methods and apparatuses may include an outer catheter configured as a sheath, e.g., a pacing or sheath adapted to quickly and easily apply a pacing signal (a "quick pacing sheath"). Also described herein are methods including any of these outer catheters (pacing sheaths) and a pacing controller configured to electrically couple to the plurality of electrical conductors of the sheath, the pacing controller comprising one or more processors and a non-transitory computing device readable medium having instructions stored thereon that are executable by the one or more processors to cause the pacing controller to apply a heart pacing stimulation from the plurality of electrodes.

Any of these apparatuses (e.g., systems) may also include an inner catheter wherein the inner catheter comprises: a distal end region that is tapered, an engagement surface proximal to a distal end of the inner catheter, wherein the engagement surface is configured to sealingly couple to a distal end region of the outer catheter (sheath) so that an outer surface of the first inner catheter is flush with an outer surface of the sheath without a gap. The inner catheters may be any of the inner catheters described herein. For example, as described above, the inner catheter may include a bend region between the engagement surface and the distal end that is configured to assume a bend of greater than 120 degrees.

The outer catheter (sheath) may include a side port at the proximal end of the elongate body, wherein the side port is in fluid communication with the lumen. The side port may be used to apply a fluid (e.g., saline, etc.) or to withdraw fluid (e.g., blood).

The plurality of electrodes may be any appropriate electrodes. In some examples the electrodes are ring electrodes arranged circumferentially around the distal end region. In some examples the electrodes may be arranged in series along the distal end region. For example, the electrodes may be arranged adjacent to each other along the longitudinal length of the elongate body of the sheath. For example, the electrodes of the plurality of electrodes may be separated from each other by between about 1 cm and 9 cm (e.g., between about 2 cm and 7 cm, between about 4 cm and 6 cm, etc.).

The conductor cables may form a bundle that extends helically around the elongate body from the plurality of electrical connectors to the plurality of electrodes. This arrangement may be particularly advantageous to provide the apparatus a thin profile, while permitting flexibility for the elongate body.

The outer catheters configured as pacing sheaths described herein may also include a yoke coupled to the plurality of electrical connectors.

For example, a system for antegrade delivery of a replacement valve may include: an outer catheter configured as a pacing sheath; an inner catheter comprising: a distal end region that is tapered, an engagement surface proximal to a distal end of the inner catheter, wherein the engagement surface is configured to sealingly couple to a distal end region of the outer catheter so that an outer surface of the first inner catheter is flush with an outer surface of the outer catheter without a gap; wherein the outer catheter is configured to receive the inner catheter, the outer catheter comprising: an elongate body having a lumen configured to receive the inner catheter, wherein the elongate body is configured to extend from outside of a body to a left ventricular apex of the heart; a hub at a proximal end of the elongate body, the hub comprising a hemostatic valve; a plurality of electrodes arranged along a distal end region of the elongate body, wherein the plurality of electrodes is spaced from the distal end region by a standoff distance; a plurality of electrical connectors extending proximally from the elongate body; and a plurality conductor cables forming a bundle extending helically around the elongate body from the plurality of electrical connectors to the plurality of electrodes, so that each electrical connector electrically connects to a corresponding electrode of the plurality of electrodes; and a pacing controller configured to electrically couple to the plurality of electrical conductors of the outer catheter, the pacing controller comprising one or more processors and a non-transitory computing device readable medium having instructions stored thereon that are executable by the one or more processors to cause the pacing controller to apply a heart pacing stimulation from the plurality of electrodes.

Also described herein are methods including pacing, including methods using any of the pacing sheaths described herein. For example, a method for percutaneous antegrade delivery and implantation of a valve in a patient may include: advancing a first inner catheter that is distally tapered into a left atrium through a transseptal puncture, wherein a distal region of the first inner catheter is flush with an outer catheter at a distal end region of the outer catheter, further wherein the outer catheter is configured as a pacing sheath having a plurality of pacing electrodes; advancing the outer catheter and either the first inner catheter or a second inner catheter that has been exchanged for the first inner catheter, so that the first or second inner catheter is in a left ventricle; applying a pacing signal to the heart from the outer catheter to maintain a sinus rhythm of the heart; advancing a guidewire out of the distal end of the first or second inner catheter and across a valve of the patient's heart; removing the first or second inner catheter, leaving the guidewire in place, and implanting a replacement valve in the patient's heart through the outer catheter All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIG. 1A is an example transcatheter aortic valve replacement (TAVR) apparatus.

FIG. 1B is an enlarged view of the tip region of FIG. 1A showing an expandable region in an expanded state.

FIGS. 4A-4C show example views of a midshaft section of the TAVR apparatus of FIG. 1A.

FIGS. 6A-6B show an example detailed views of an outer catheter of the TAVR apparatus of FIG. 1. FIG. 6A shows an outer view; FIG. 6B shows a section through the apparatus of FIG. 6A.

FIG. 8 shows an example detail view of an inner catheter.

FIG. 9 shows an example inner view of an inner catheter.

FIGS. 20A and 20B illustrate an example of a system as described herein.

FIG. 21 shows an example of a method of using a system as described in FIGS. 21A-21B.

FIGS. 23A-23C illustrate an example of a mitral valve centering guidewire including an expandable deflector. This example is a 0.035" diameter centering guidewire having a J-tip.

FIG. 23A shows a side perspective view of the mitral valve centering guidewire. FIG. 23B shows a section through the view of FIG. 23A. FIG. 23C is a slightly enlarged view of the distal end region of the device of FIGS. 23A-23B with the expandable deflector (e.g., balloon) in a collapsed configuration.

FIG. 25A shows a side perspective view of the mitral valve centering guidewire. FIG. 25B shows a section through the view of FIG. 25A. FIG. 25C is a slightly enlarged view of the distal end region of the device of FIGS. 25A-25B with the expandable deflector (e.g., balloon) in a collapsed configuration. FIG. 25D shows the expandable deflector of FIGS. 25A-25C in an expanded configuration.

FIG. 26A shows a side perspective view of the distal end region of the inner catheter.

FIG. 26B shows a section through the view of FIG. 26A. FIG. 26C is a section (section C-C') transverse through the distal end region of FIG. 26B.

DETAILED DESCRIPTION

Figure 2A:
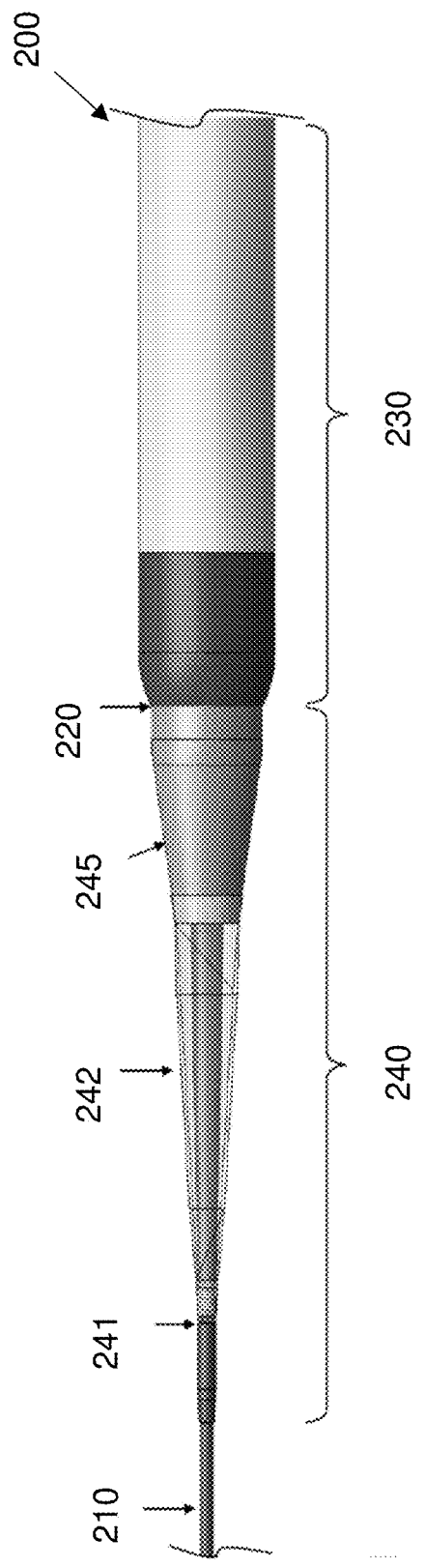
FIG. 2A shows an example distal tip section of the TAVR apparatus of FIG. 1A.

The present disclosure describes apparatuses (e.g., device, systems, etc.) and methods for inserting, guiding, and implanting a replacement a cardiac valve (e.g., aortic valve, mitral valve, etc.) using an antegrade approach. In some examples, a transcatheter valve replacement apparatus may include an outer catheter and at least one inner catheter that may be detachably coupled together. The inner and outer catheters may have a decreasing stiffness as in a distal direction away from the surgeon or handle of the apparatus. Any of the catheters may be pre-shaped or shaped by the surgeon. In addition, or in the alternative, any of the inner catheters may include a pre-shaped or shapable distal tip. Any of the apparatuses may include a dilation balloon to assist in enlarging a puncture or hole, such as an atrial septum puncture.

The apparatuses and methods described herein may include or may be configured for use with an expandable deflector to prevent entanglement with the chordae tendinae. The expandable deflector may be integrated as part of the inner catheter and/or guidewire. Any of these method and apparatuses may also include pacing of the heart during the procedure. In particular, any of these methods and apparatuses may include an outer catheter configured as a pacing sheath adapted to apply a pacing signal.

FIG. 1A is an example transcatheter aortic valve replacement (TAVR) apparatus 100. Although described herein as a system, the TAVR apparatus 100 may be a device (e.g., an inner catheter). The TAVR apparatus 100 may be configured as a system including an optional guidewire 110, an optional hemostasis valve 120, an outer catheter 130, an inner catheter 140, an optional 3-way stopcock 150, and an inflation bulb 160. The inner catheter may include a dilation balloon 142, a distal tip 145. Other example TAVR apparatuses may include fewer, more, or different components than the TAVR apparatus 100 shown in FIG. 1A.

The TAVR apparatus 100 may be used for percutaneous delivery of a replacement valve using an antegrade approach via the left ventricle. The TAVR apparatus 100 may be well suited for percutaneous delivery through a variety of blood vessels, including but not limited to femoral arteries. In some examples, flexibility of the TAVR apparatus 100 may vary from a proximal end (e.g., an end adjacent to the hemostasis valve 120) to a distal end (e.g., an end adjacent to the distal tip 145). For example, the flexibility of the outer catheter 130 and/or the inner catheter 140 may vary from relatively stiff near the hemostasis valve 120 to relatively flexible near the distal tip 145. The inner catheter 140 may be interchangeable with other inner catheters having, for example, differently shaped distal tips. These other inner catheters are described in more detail in conjunction with FIGS. 18A-18L.

One or more guidewires may be included as part of the system. In some examples, the guidewire 110 may be approximately 0.035 inches in diameter. In some other examples, the guidewire 110 may be any other greater diameter, such as diameters greater than 0.035 inches (including, but not limited to 0.040, 0.045, 0.050, or any other feasible greater diameter). In some other examples, the guidewire 110 may be any other lesser diameter, including diameters less than 0.035 inches (including, but not limited to 0.030, 0.025, 0.020, or any other feasible smaller diameter). The guidewire 110 may be formed form any feasible material, including Nitinol.

The hemostasis valve 120 may provide a hemostatic barrier for any attached catheter, including the outer catheter 130 and the inner catheter 140. The hemostasis valve 120 may attach to, and otherwise be coupled to the outer catheter 130. The inner catheter 140 may be detachably coupled to the outer catheter 130. The hemostasis valve 120 may also receive and direct air from the inflation bulb 160. Alternatively, or in addition, the hemostasis valve 120 may receive the guidewire 110. Although not shown, the guidewire 110 may travel through one or more concentric lumens and may exit through the distal tip 145. The surgeon may manipulate the guidewire 110 to assist in positioning a dilatation balloon 142 in a desired region. The inner catheter(s) may include a rapid exchange monorail connection for a guidewire, as will be described in greater detail herein.

The outer catheter 130 may be concentric with respect to the inner catheter 140. In some examples, the outer catheter 130 may include a first section 133 and a second section 136. The first section 133 may be stiffer (e.g., less flexible) with respect to the second section 136. Construction of the outer catheter 130 is described in more detail in conjunction with FIGS. 4A-4C. The inner catheter 140 may be coupled to the dilation balloon 142 and the inflation bulb 160. In some examples, the inner catheter 140 may slide easily with respect to the outer catheter 130. Introduction of air by the inflation bulb 160 may cause the dilation balloon 142 to expand. As shown, when not inflated the dilation balloon 142 may be collapsed and relatively close in size to the guidewire 110. View 170 (FIG. 1B) shows a dilation balloon 143 in its expanded state.

The hemostasis valve 120 is shown coupled to the 3-way stopcock 150 by connection tubing 155 through a flush port 157. The 3-way stopcock 150 may enable any feasible liquid to be percutaneously introduced to the patient through the hemostasis valve 120.

FIG. 2A shows an example distal tip section 200 of the TAVR apparatus 100 of FIG. 1A. The distal tip section 200 may include a guidewire 210, an outer catheter 230 and an inner catheter 240. The guidewire 210, the outer catheter 230, and the inner catheter 240 may be examples of the guidewire 110, the outer catheter 130, and the inner catheter 140 of FIG. 1A, respectively.

A transition 220 from the outer catheter 130 to the inner catheter 140 may be relatively smooth and seamless. A smooth and seamless transition 220 may aid in the insertion and manipulation of the TAVR apparatus 100 and may prevent gaps that may catch on and/or scrape the lumen of the body into which the system is inserted. The inner catheter 240 may include a tapered element 245. The tapered element 245 enables a size (diameter) reduction from the transition 220 to the guidewire 110.

The inner catheter 240 may extend partially or wholly through the outer catheter 230. A distal tip 241 may be coupled to, or integral with the inner catheter 240. The distal tip 241 may have a low crossing profile to aid in maneuvering, manipulating, and inserting the TAVR apparatus 100. In addition, in some examples the distal tip 241 may be highly flexible. An expandable member (e.g., a dilation balloon 242) may be disposed on the inner catheter 240. As shown, the dilation balloon 242 may be collapsed and/or folded. Other expandable members may include expandable frames or struts, or the like.

Figure 2B:
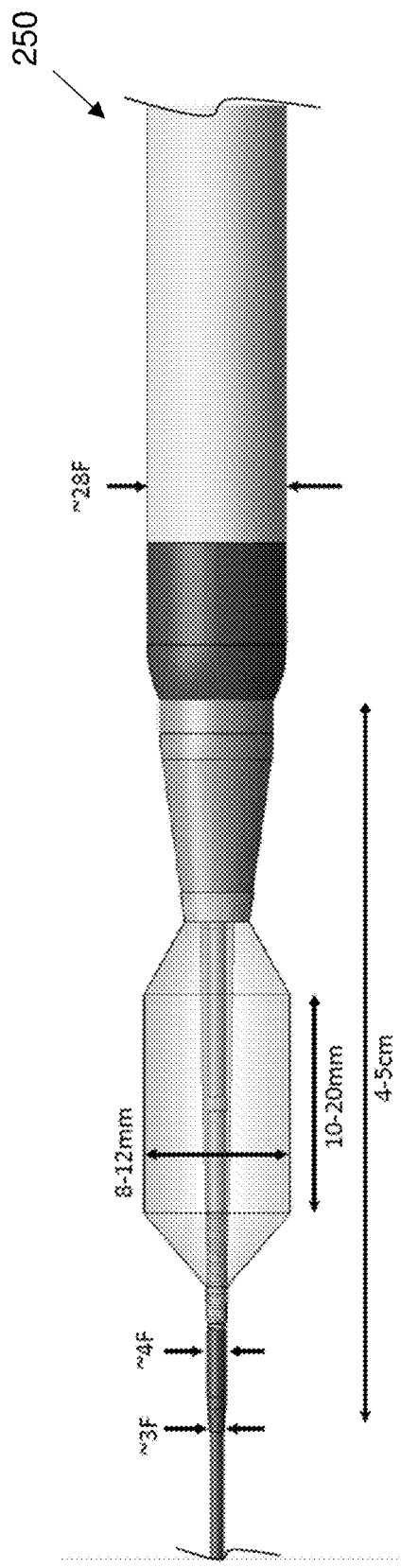
FIG. 2B shows example measurements associated with a distal tip section.

FIG. 2B shows example measurements associated with a distal tip section 250. The outer catheter may be, e.g., 28 French (Fr.). In this example, the exposed portion of the inner catheter may be between 4 and 5 centimeters (cm). The dilation balloon may be between approximately 8 and 12 millimeters (mm) and between approximately 10 and 20 mm in length. The distal tip may taper from 4 Fr. to 3 Fr.

Figure 3A:
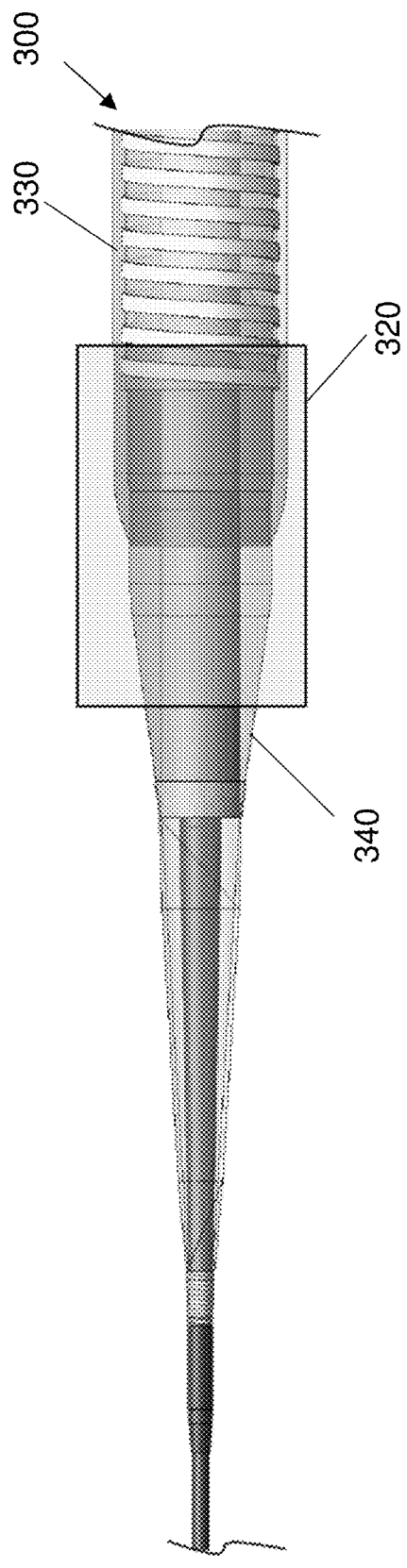
FIGS. 3A-3C shows an example distal tip region of the TAVR apparatus of FIG. 1A.
Figure 3C:
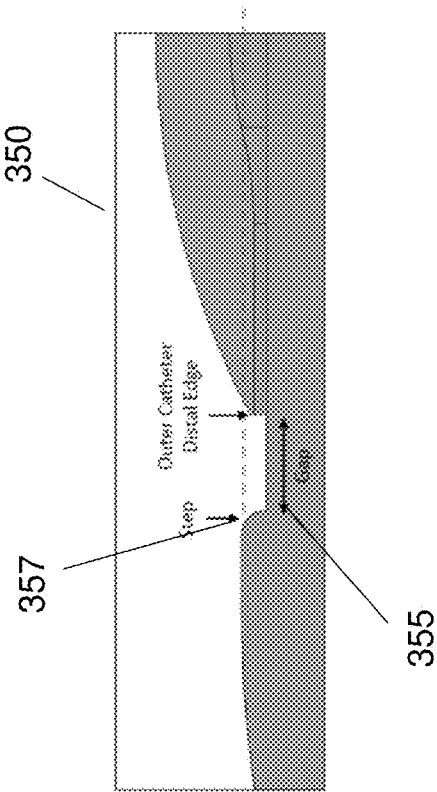
Figure 3B:
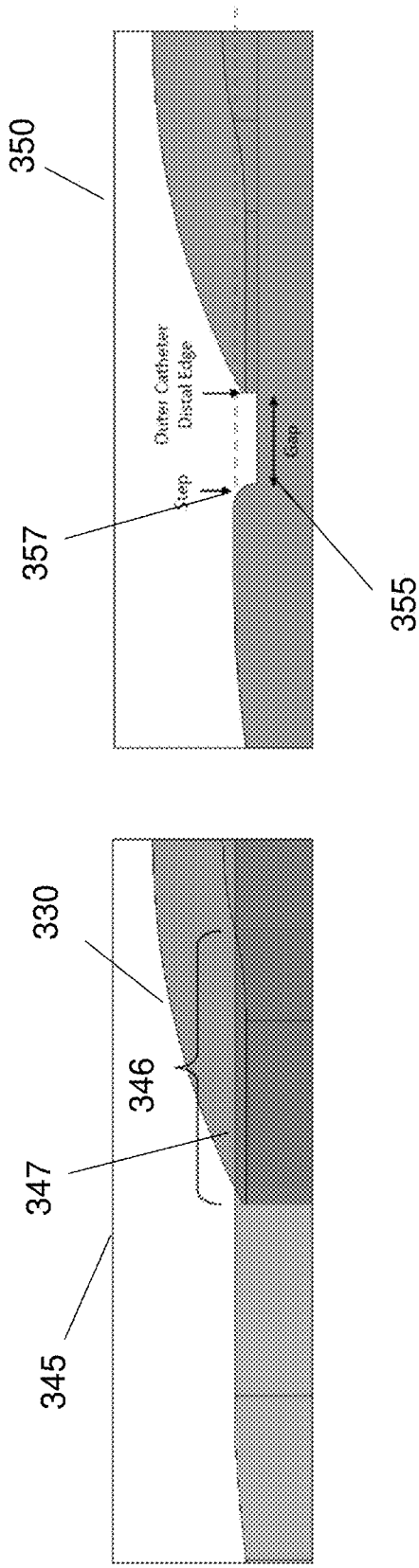

FIGS. 3A-3C show an example distal tip region 300 of the TAVR apparatus 100 of FIG. 1A. The distal tip region 300 shown in FIG. 3A may include an outer catheter 330 and an inner catheter 340. The outer catheter 330 and the inner catheter 340 may be examples of the outer catheter 230 and the inner catheter 240 of FIG. 2, respectively. The distal tip region 300 may include a transitional area 320.

In some examples, a transition from the outer catheter 330 to the inner catheter 340 may be accomplished with an interference fit as shown in view 345 (FIG. 3B) of the transitional area 320. For example, a mechanical interference may exist between the outer catheter 330 and the inner catheter 340 such that a tapered element 347 of the inner catheter 340 may compress a distal portion of the outer catheter 330. In some examples, the mechanical interference region may be 346.

In some examples, a transition from the outer catheter 330 to the inner catheter 340 may include a gap 355 as shown in view 350 (FIG. 3C) of the distal tip region 300. The view 350 also shows a step 357 that may hide or occlude an outer edge of the outer catheter 330. The step 357 may help smooth the transition between the outer catheter 330 and the inner catheter 340. In addition, the gap 355 may enable tolerance and/or manufacturing variations between a variety of parts of the TAVR apparatus 100.

FIGS. 4A-4C show example views of a midshaft section of the TAVR apparatus 100 of FIG. 1A. A midshaft region 410 is shown. FIG. 4B shows a section through the device of FIG. 4A. The midshaft region 410 includes an outer catheter 430 and an inner catheter 440. In some examples, the outer catheter 430 may include a first section 431 and a second section 432. In some examples, the outer catheter 430 may be stiffer (e.g., less flexible) proximally toward the hemostasis valve (not shown) and more flexible distally away from the hemostasis valve. In some examples, the first section 431 may be stiffer than the second section 432. A transition 434 between the first section 431 and the second section 432 may also be a transition between stiffness (e.g., durometer) and/or internal reinforcements.

The inner catheter 440 may include a lock ring 441. The outer catheter 430 may include a coupler 435. As the inner catheter 440 is inserted into the proximal end of the outer catheter 430, the lock ring 441 may slip into a space formed within the coupler 435. In this manner the inner catheter 440 may be captured and locked (e.g., detachably coupled) together with respect to the outer catheter 430.

A cross-sectional view 450 of the midshaft region 410 is shown which includes the outer catheter 430, the inner catheter 440, the lock ring 441, and the coupler 435. In some examples, the outer catheter 430 may decrease in diameter at the transition 434. For example, the first section 431 may be 2-3 Fr. larger than the second section 432. In some other examples, the first section 431 may be greater than 3 Fr. larger than the second section 432. In still other examples, the first section 431 may be less than 1 Fr. larger than the second section 432.

In some examples, the inner catheter 440 may include a rapid exchange port 446 through which a guidewire 411 (which may be an example of the guidewire 110 of FIG. 1A) may pass therethrough.

View 460 in FIG. 4C shows detail associated with the coupler 435. The coupler 435 may be formed from stainless-steel, Nitinol, or any other feasible material. In some examples, the coupler 435 may be formed by laser cutting feasible material. The coupler 435 may include a split ring 461 that enables the lock ring (not shown) to pass therethrough. The coupler 435 may also include a solid ring 462 that prevents further distal travel of the lock ring. The lock ring may be captured in a space 463 within the coupler 435. The coupler 435 may include two or more flared tabs 465 that allow the coupler 435 to be welded or otherwise attached to the outer catheter 430.

Figure 5:
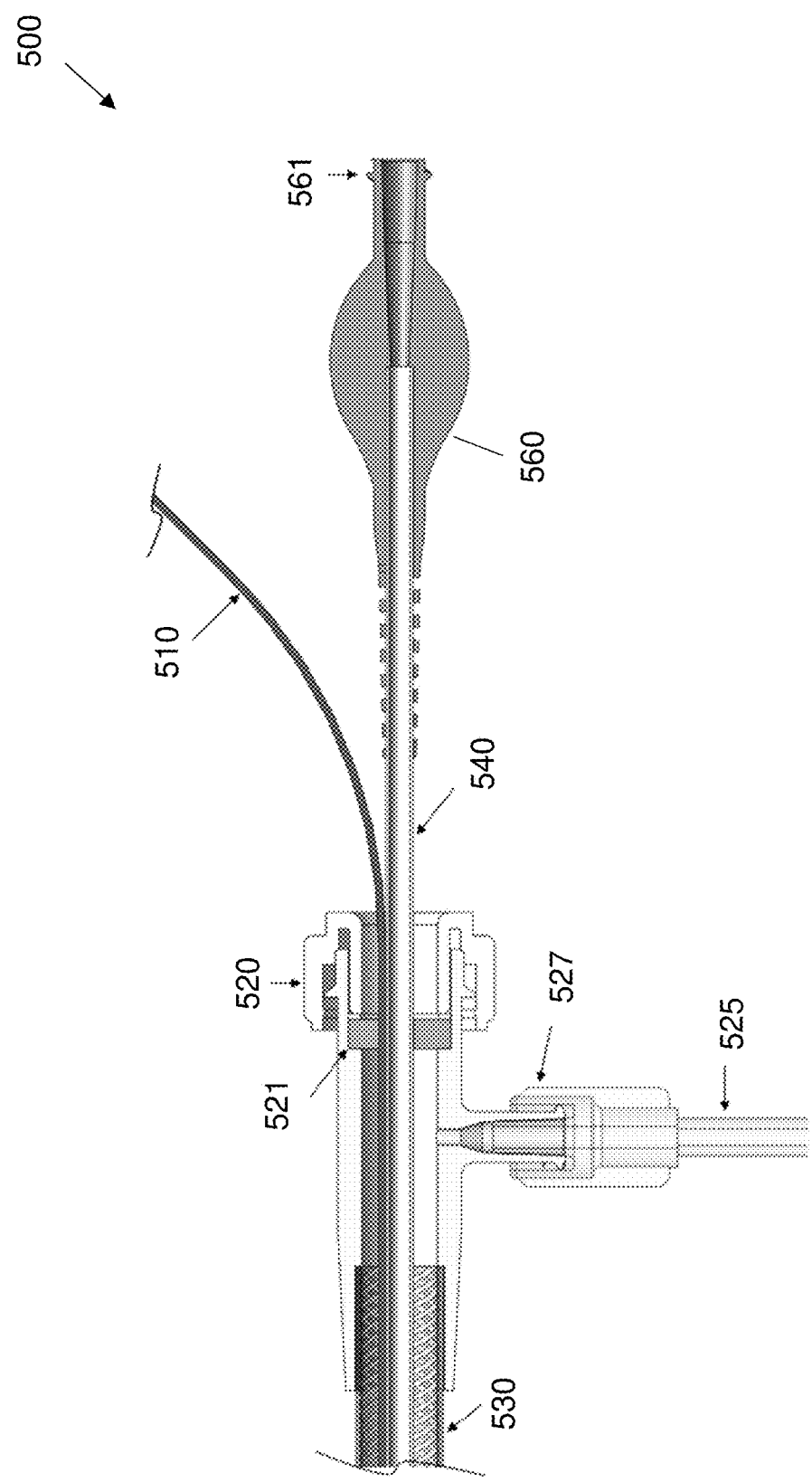
FIG. 5 shows a proximal view of the TAVR apparatus of FIG. 1A.

FIG. 5 shows a proximal view 500 of the TAVR apparatus 100 of FIG. 1A. The view 500 shows a guidewire 510, a hemostasis valve 520, an outer catheter 530, an inner catheter 540, and an inflation bulb 560 which may be examples of the guidewire 110, the hemostasis valve 120, the outer catheter 530, the inner catheter 540, and the inflation bulb 160 of FIG. 1A. The inflation bulb 560 may include an air inlet 561.

The hemostasis valve 520 may be coupled with the outer catheter 530, may also rotate with respect to the outer catheter 530. The hemostasis valve 520 may include a seal 521 to prevent and/or limit the unintended passage of fluids from the outer catheter 530. A flush port 527 may be coupled to connection tubing 525. The connection tubing 525 may be coupled directly or indirectly to any feasible fluid source.

Thus, the connection tubing 525 may deliver a fluid to the flush port 527 and to the outer catheter 530.

FIGS. 6A-6B show an example of detailed views of an outer catheter of the TAVR apparatus 100 of FIG. 1A. A first example view 610 may include a hemostasis valve 620 and an outer catheter 630, which may be examples of the hemostasis valve 120 and the outer catheter 130 of FIG. 1A. In addition, the view 610 may show an outer catheter distal tip 640 and a coupler 635. The coupler 635 may be an example of the coupler 435 of FIG. 4A.

The outer catheter 630 may include a first section 633 and a second section 636. As shown, there may be a transition 637 between the first section 633 and the second section 636. In some examples, the first section 633 may be stiffer relative to the second section 636. For example, the first section 633 may include a braid 634 that may offer stiffness, kink resistance, and resistance to torsion (e.g., torqueability). In contrast, the second section 636 may include a spiral, or spiral-like reinforcement 638. The spiral or spiral-like reinforcement may offer less stiffness, with respect to the first section 633. However, the second section 636 may still have kink resistance and resistance to torsion. In addition, the first section 633 may be 30 F in diameter and the second section 636 may be 28 F in diameter. These diameters are exemplary and are not meant to be limiting. The first section 633 and the second section 636 may be any feasible diameter. In some examples, the diameter of the second section 636 may be less than the diameter of the first section 633. A smaller diameter may enable the second section 636 to be more flexible relative to the first section 633.

The hemostasis valve 620 may be rotatable with respect to the outer catheter 630. In some examples, the hemostasis valve 620 may include a hub 621 that enables 360 degrees of rotation between a proximal and a distal portion of the hemostasis valve 620. The hemostasis valve 620 may include a flush port 627.

The outer catheter distal tip 640 may include any feasible radiopaque material (e.g., a radiopaque marker) to enable the surgeon to visualize and/or locate the distal end of the outer catheter 630 using fluoroscopy or other feasible or similar procedures. In some examples, the outer catheter distal tip 640 may include a tungsten loaded polymer, such as a tungsten loaded Pebax®.

A second example view 650 shows example dimensions of the outer catheter 630. In some examples, the second section of the outer catheter 630 may be approximately between 30 and 40 cm in length. The inner diameter of the first section of the outer catheter 630 may be about 26 Fr. The inner diameter of the second section of the outer catheter 630 may be about 24 Fr. Furthermore, in some examples, an inner diameter of the outer catheter distal tip 640 may be about 23 Fr. (or a decrease of about 1 Fr. with respect to the inner diameter of the second section. The inner diameter 651 of the outer catheter 630 may include any feasible lubricious liner such as any feasible polytetrafluoroethylene (PTFE).

Figure 7:
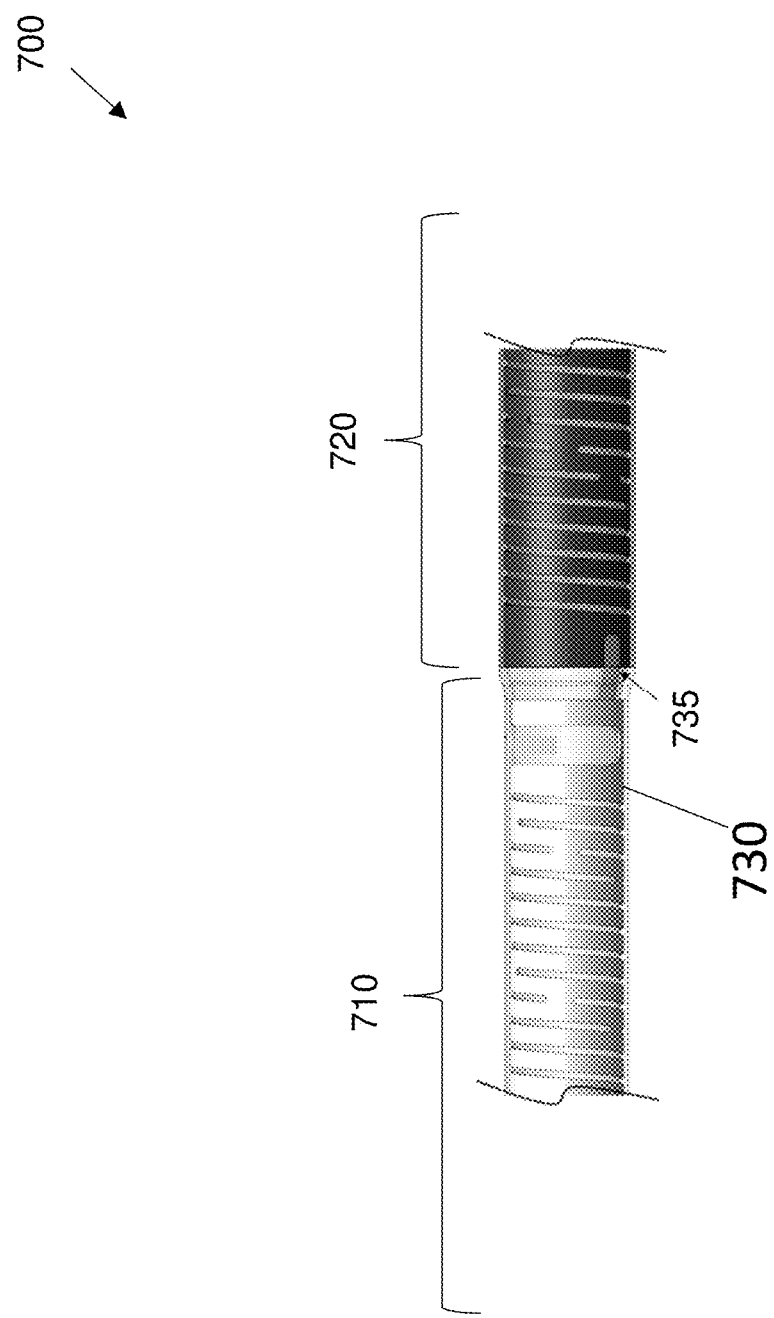
FIG. 7 shows an example detail view of a transition area of an outer catheter.

FIG. 7 shows an example detail view of a transition area 700 of an outer catheter. The transition area 700 may include a distal section 710 and a proximal section 720. A coupler 730 may be included in the distal section 710. The coupler 730 may be an example of the coupler 435 of FIG. 4A.

In some examples, the distal section 710 and/or the proximal section 720 may include overlapping layers of coil and/or braid reinforcement to increase kink resistance and resistance to torsion. In some examples, the distribution and/or type of coil and braid material may vary proximally to distally along the outer catheter. In this manner, the stiffness of the outer catheter may be made stiffer in the proximal section 720 and less stiff in the distal section 710.

In some examples, the distal section 710 and/or the proximal section 720 may include overlapping coils that are wound in opposite directions (clockwise and counterclockwise). This configuration of overlapping coils may allow for increased flexibility and resistance to torsion.

In some examples a coil section from the distal section 710 may be welded to a coil section from the proximal section 720 through the coupler 730. For example, the coupler 730 may be integral to a coil of the distal section 710. Tabs 735 of the coupler 730 may be welded to a coil of the proximal section 720. Coils of the distal section 710 and the proximal section 720 may be laser cut to control and/or modify flexibility, stiffness, resistance to torsion, and the like.

FIG. 8 shows an example detail view of an inner catheter 800. The inner catheter 800 may include an inflation bulb 810, a proximal shaft 815, a distal shaft 820, a lock ring 830, a proximal tapered element 840, a distal tapered shaft 850, a dilation balloon 860, an inner shaft 880, and a distal tip 890.

The optional inflation bulb 810 may be used to inflate the optional dilation balloon 860 through a lumen included or formed by the inner catheter 800. In some examples, the proximal shaft 815 may be formed from a stainless-steel shaft. In some other examples, the proximal shaft 815 may be formed from any other feasible material. The distal shaft 820 may include a braided inner layer and durable outer layer. The lock ring 830, which may be an example of the lock ring 441, may be disposed on the distal shaft 820.

The proximal tapered element 840 may be distal with respect to the lock ring 830 and/or the distal shaft 820. The distal tapered shaft 850 may extend beyond the proximal tapered element 840. As shown, the distal tapered shaft 850 may be enclosed and/or encircled by the dilation balloon 860. The dilation balloon 860 is shown in a possible inflated state. A radiopaque marker band 870 may be disposed on the distal tapered shaft 850 to assist the surgeon in locating the dilation balloon 860 within the patient.

The inner catheter 800 may include a coil or braid reinforced microcatheter inner shaft. The distal tip 890 may also include a radiopaque material (e.g., a radiopaque marker).

FIG. 9 shows an example inner (sectional) view of an inner catheter 900. The inner catheter 900 may include an inflation lumen 910, a skived hypotube 920, and a rapid exchange port 930. The inflation lumen enables air to be transferred from an inflation bulb to a dilation balloon. The skived hypotube 920 may be adjacent to the inflation lumen 910. The skiving may be variable as described in more detail in FIG. 10.

The inner catheter 900 may also include the rapid exchange port 930 to allow the insertion of a guidewire. In some examples, the inner catheter 900 may include an inner lumen 940. The inner lumen 940 may be coated with and/or include a lubricious coating of PTFE, for example.

Figure 10:
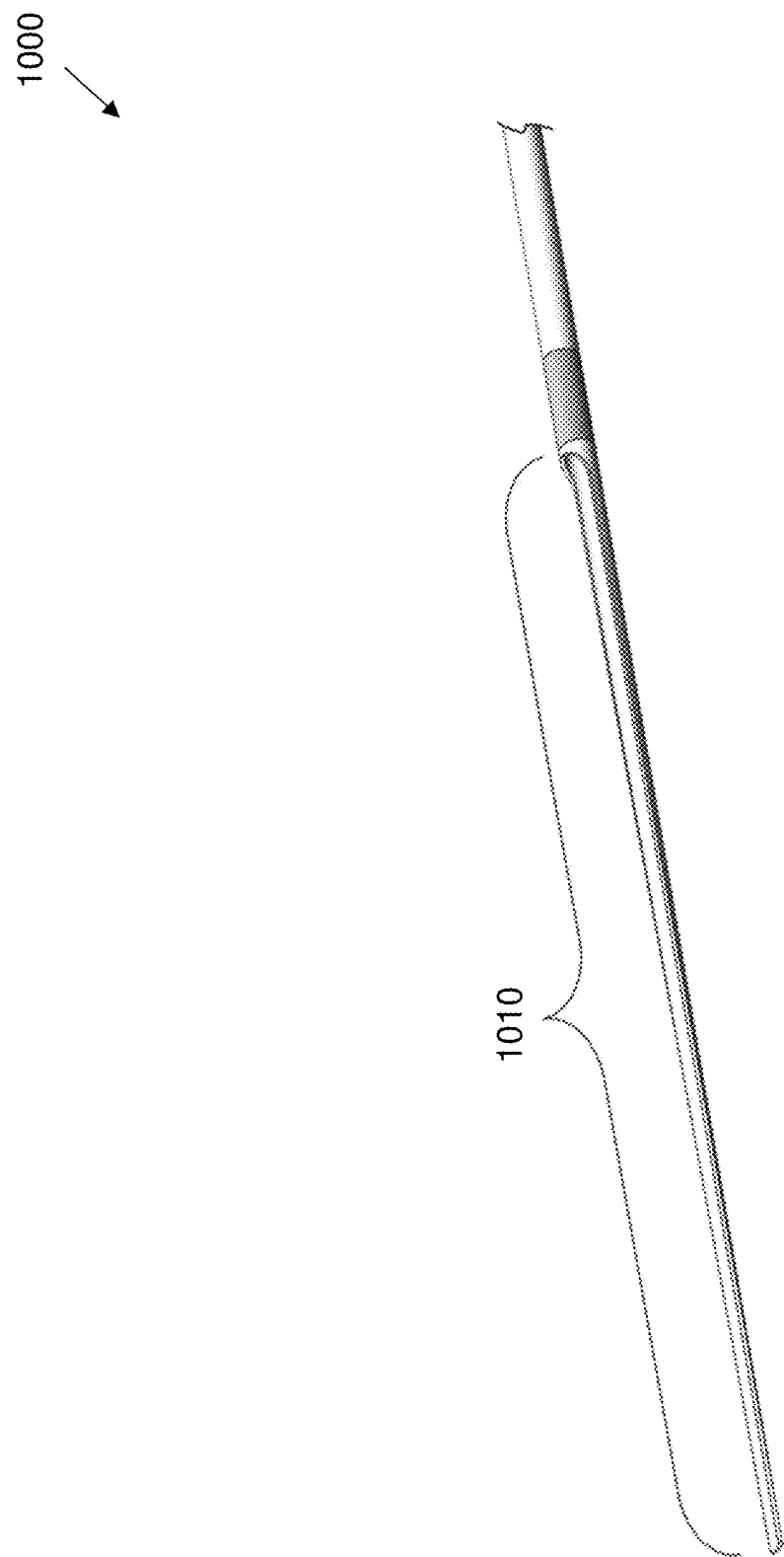
FIG. 10 shows an example of a skived hypotube.

FIG. 10 shows an example of a skived hypotube 1000. The skived hypotube 1000 may be an example of the skived hypotube 920 for FIG. 9. As shown, the skived hypotube 1000 may include a continuous linear skive 1010 that has a more material proximally and less material distally. The transition of material from the proximal end to the distal end may be smooth and continuous. The continuous linear skive 1010 may provide more flexibility toward the distal end of the skived hypotube 1000.

Figure 11A:
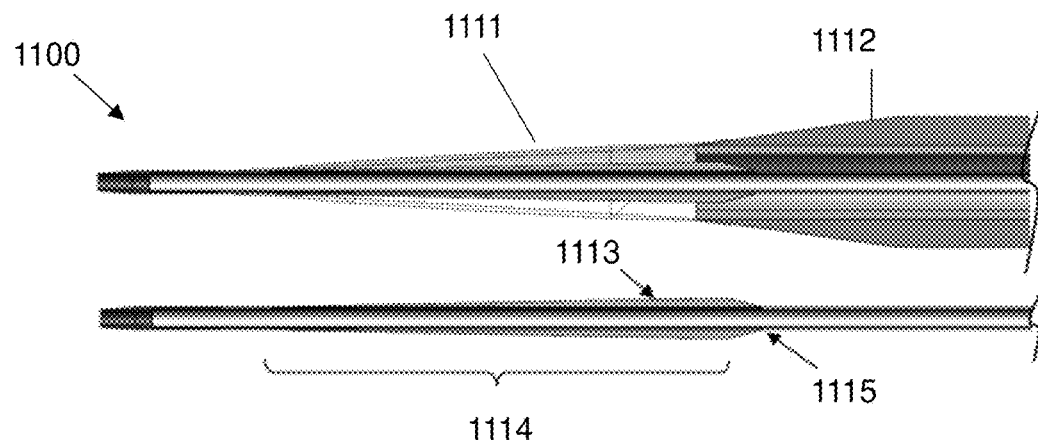
FIGS. 11A-11C show examples of an inner catheter, particularly under a dilation balloon.
Figure 11B:
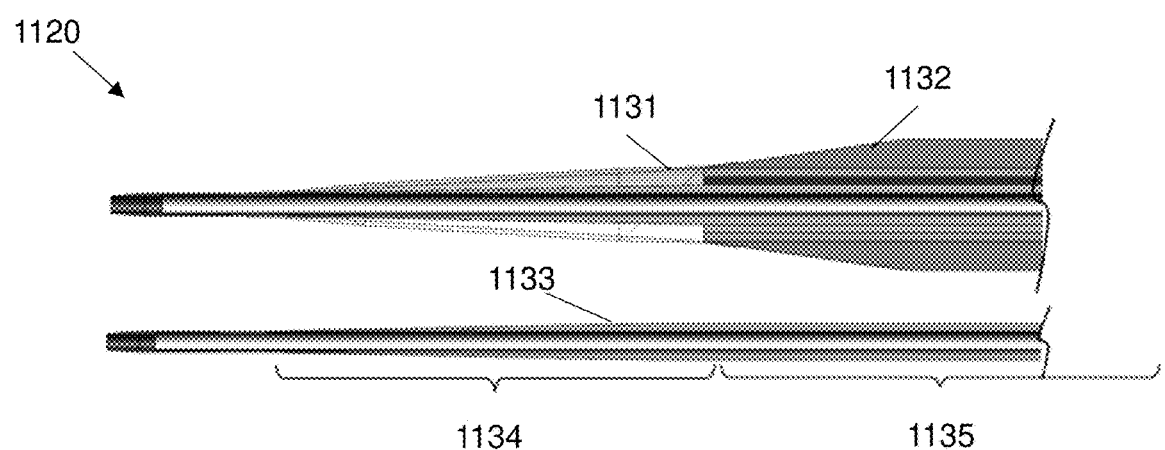
Figure 11C:
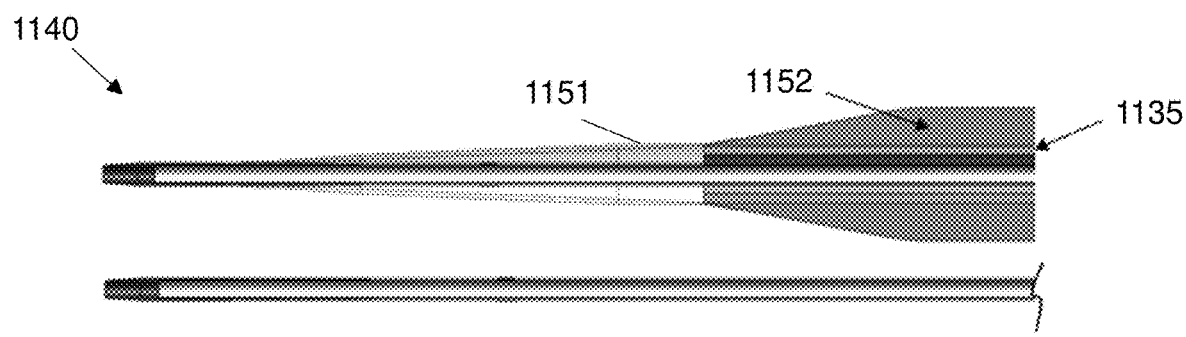

FIGS. 11A-11C show examples of an inner catheter, particularly under a dilation balloon. The examples shown here may be examples of a distal end of the inner catheter 800 of FIG. 8. FIG. 11A shows a first example of an inner catheter 1100. The inner catheter 1100 may include a dilation balloon 1111 and a first tapered element 1112. As shown, the dilation balloon 1111 may be collapsed (not deployed or inflated). The inner catheter 1100 may include a second tapered element 1113 that is disposed substantially under the balloon region 1114. Notably, the second tapered element 1113 ends approximately near a region 1115 that the dilation balloon 1111 may contact the first tapered element 1112.

FIG. 11B shows a second example of an inner catheter 1120. The inner catheter 1120 may include a dilation balloon 1131, a first tapered element 1132, and a second tapered element 1133. As shown the second tapered element may be tapered under the balloon region 1134 and have a constant outer diameter the rest of the length of the inner catheter 1135.

FIG. 11C shows a third example of an inner catheter 1140. The inner catheter 1140 may include a dilation balloon 1151 and a tapered element 1152. The tapered element 1152 may be thicker than the corresponding first tapered elements of FIGS. 11A and 11B. In some examples, an inflation lumen 1135 integral to the inner catheter 1140 may be thinner than corresponding inflation lumens of the inner catheter 1100 and 1120.

Figure 12A:
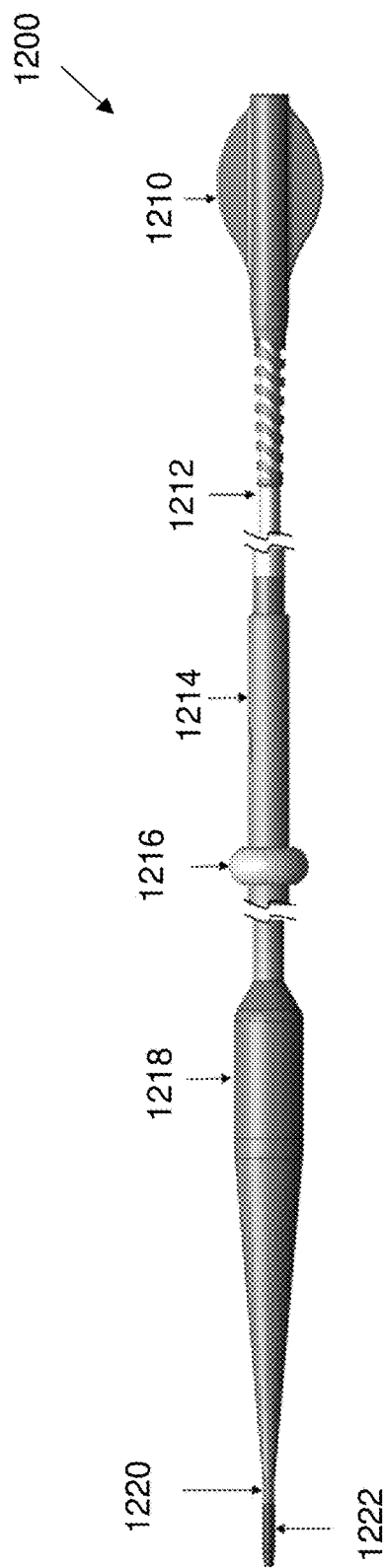
FIG. 12A shows an example inner catheter.

FIG. 12A shows an example inner catheter 1200. The inner catheter 1200 may not include a dilation balloon. The inner catheter 1200 may include a handle 1210, a proximal shaft 1212, a distal outer shaft 1214, a lock ring 1216, a tapered element 1218, an inner shaft 1220, and a distal tip 1222.

The handle 1210 may enable the surgeon to insert the inner catheter 1200 into an outer catheter (such as the outer catheter 130 of FIG. 1, or any other feasible outer catheter). In some examples, the lock ring 1216 may engage with a coupler of the outer catheter (not shown). The proximal shaft 1212 may be formed from stainless-steel and be relatively stiff. The stiffness of the inner catheter 1200 may get progressively more flexible, the farther away to get from the handle 1210.

The distal outer shaft 1214 may be distal to the proximal shaft 1212. In some cases, the distal outer shaft 1214 may cover the proximal shaft 1212. The lock ring 1216 may be disposed on the distal outer shaft 1214. The inner catheter 1200 may be inserted into any feasible outer catheter. In some examples, the lock ring 1216 may engage with a corresponding coupler, such the coupler 435 of FIG. 4A.

The tapered element 1218 may be disposed on a distal end of the distal outer shaft 1214. The shape of the tapered element 1218 may enable the inner catheter 1200 to be inserted and enlarge blockages or punctures in lumens, although other uses are possible. Distal to the tapered element 1218 is the inner shaft 1220. In some examples, the inner shaft 1220 may be reinforced with a coil and/or a braid similar to as described with respect to the outer catheter of FIGS. 6A-6B.

The distal tip 1222 may be distal with respect to the inner shaft 1220 and the tapered element 1218. In some examples, the distal tip 1222 may include a radiopaque material (e.g., a radiopaque marker) to enable the surgeon to locate and track the inner catheter using fluoroscopy or other similar methods.

Figure 12B:
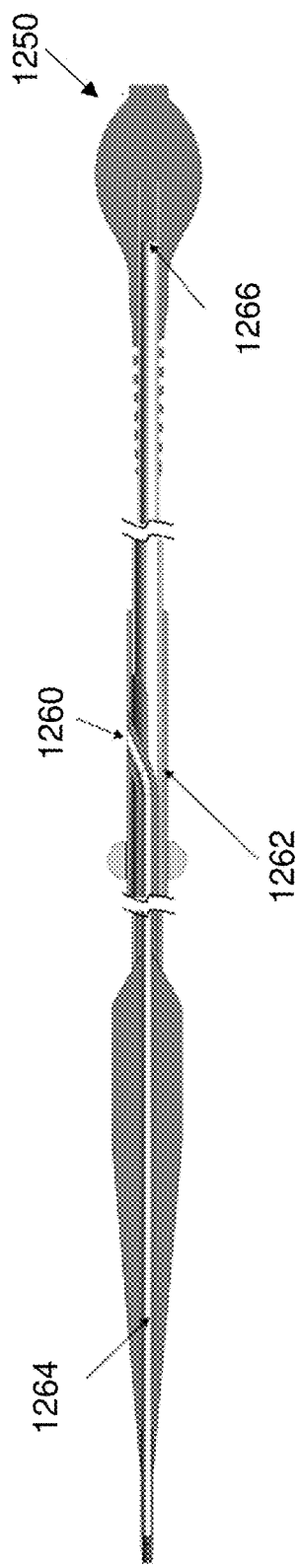
FIG. 12B shows a cross section of the inner catheter.

FIG. 12B shows a cross section 1250 of the inner catheter 1200. The cross section 1250 may show a rapid exchange port 1260, a skived hypotube 1262 and a guidewire lumen 1264. The rapid exchange port 1260 may enable a guidewire to be inserted into the guidewire lumen 1264. The skived hypotube may be an example of the skived hypotube 1000 of FIG. 10. The proximal shaft may be blocked (shown at 1266) since there is no dilation balloon that needs to be inflated.

Figure 13A:
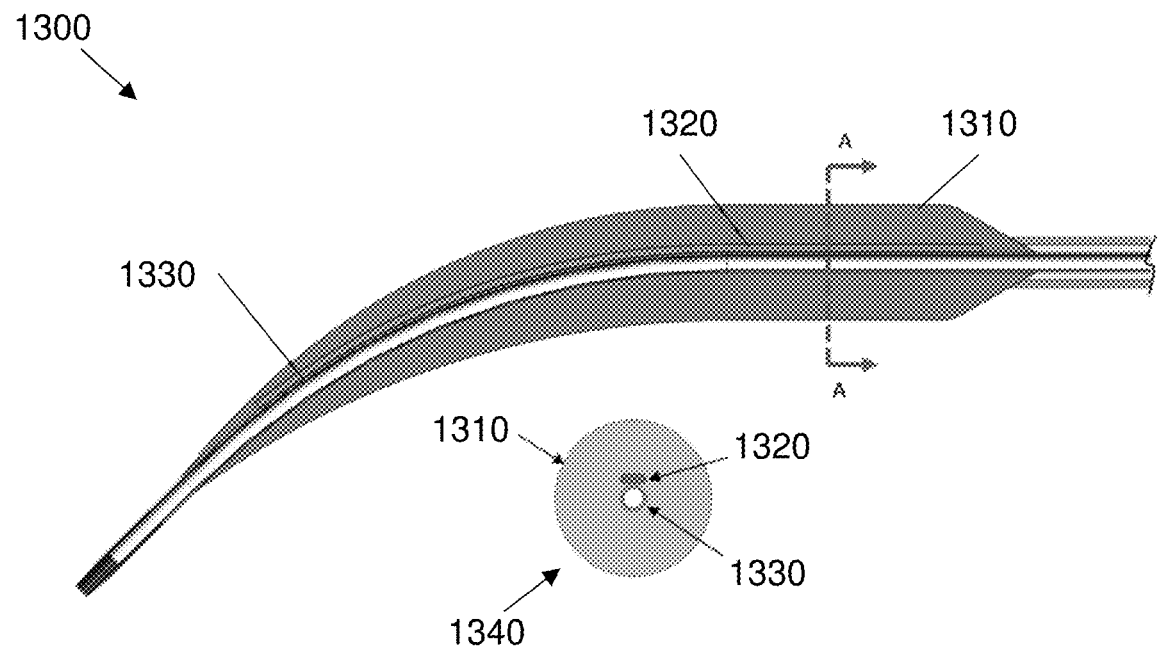
FIG. 13A shows an example distal end of any feasible inner catheter.

FIG. 13A shows an example distal end 1300 of any feasible inner catheter. In some examples, the distal end 1300 may be the distal tapered shaft 850 of FIG. 8, any of the tapered elements of FIG. 11A-11C, the tapered element 1218 of FIG. 12A, or the like. The distal end 1300 may include a tapered element 1310, an embedded shape wire 1320, and a guidewire lumen 1330. The embedded shape wire 1320 may be laminated and/or encapsulated within the tapered element 1310. In some examples, the embedded shape wire 1320 may be a stainless-spring steel, Nitinol, or any other feasible material.

The distal end 1300 may be shaped into any feasible shape including a curve, as shown. The tapered element 1310 may be shaped, at least in part, by the embedded shape wire 1320. In some examples, the embedded shape wire 1320 may hold or retain the shape thereby causing the tapered element 1310 to maintain a desired shape.

A cross-section 1340 of the distal end 1300 is shown. The cross section 1340 shows a cross-section of the tapered element 1310, the embedded shape wire 1320, and the guidewire lumen 1330. As shown, the cross-section of the embedded shape wire 1320 may be a flattened oval, however other cross-sections are possible. For example, the cross-section of the embedded shape wire 1320 may be round, flat/ribbon, square, or any other feasible shape.

In addition, or alternatively, the distal end 1300 may be shaped by application of heat. For example, the tapered element 1310 may be formed from or include a heat set polymer. The tapered element 1310 may be placed into a heat set die to shape into a desired shape. In some other examples, the shape of the tapered element 1310 may be controlled through pull-wires. The pull wires may be anchored to the tapered element 1310 and made available to the surgeon.

In some examples, the tapered element 1310 may include a stylet channel (not shown). Different semi-rigid shaped stylets could be inserted through a port causing the tapered element 1310 to conform to the shape of the stylet.

Figure 13B:
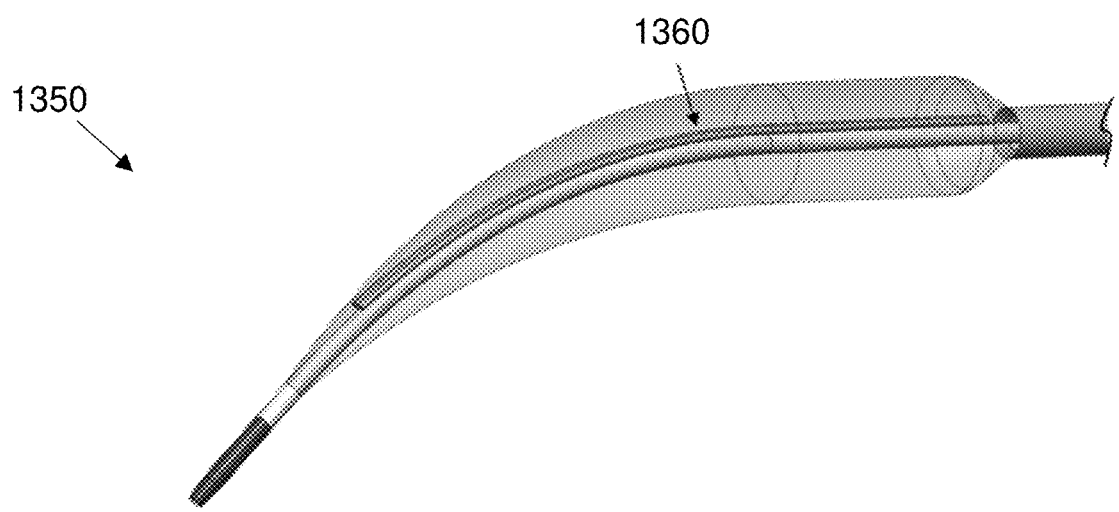
FIG. 13B shows another example distal end.

FIG. 13B shows another example distal end 1350. Construction of the distal end 1350 may be similar to the construction of the distal end 1300, however in some examples the distal end 1350 may include a shapable embedded shape wire 1360. The shapable embedded shape wire 1360 may be any feasible ductile material or metal that may be manual shaped by the surgeon or other user.

Figure 14A:
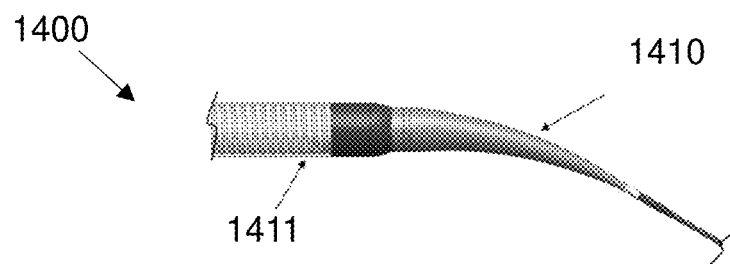
FIGS. 14A-14C show example shapes of a distal end of any feasible inner catheter.
Figure 14B:
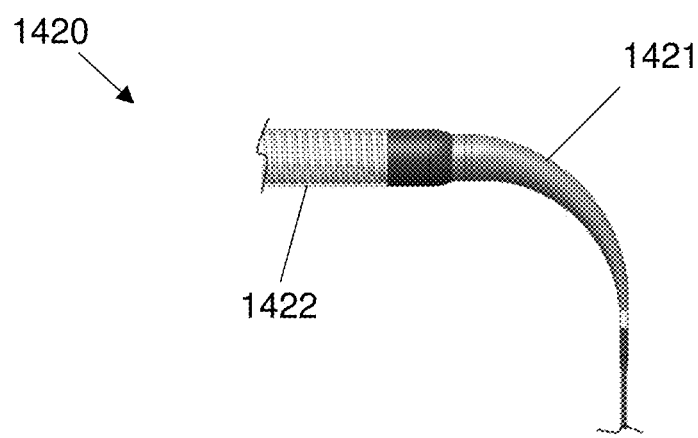
Figure 14C:
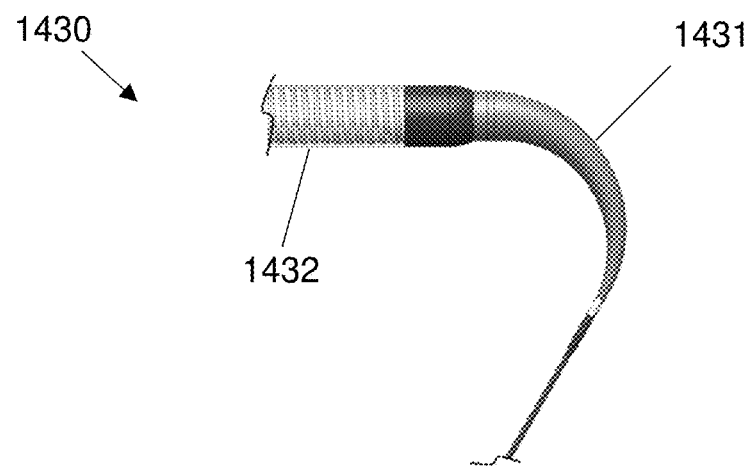

FIGS. 14A-14C show example shapes of a distal end of any feasible inner catheter. FIG. 14A shows a distal end 1400 that includes a tapered element 1410 and a distal outer shaft 1411. In this example, the tapered element 1410 may be shaped to have an approximate 30 degree bend. FIG. 14B shows a distal end 1420 that includes a tapered element 1421 and a distal outer shaft 1422. In this example, the tapered element 1421 may be shaped to have an approximate 90 degree bend. FIG. 14C shows a distal end 1430 that includes a tapered element 1431 and a distal outer shaft 1432. In this example, the tapered element 1431 may be shaped to have an approximate 120 degree bend.

The bends shown in FIGS. 14A-14C are meant to be exemplary and non-limiting. In other implementations, the distal end of the inner catheter may have any feasible bend.

In some examples, the distal end of the inner catheter may be bent, but relatively flexible. The guidewire may straighten the distal end, when inserted. Conversely, when the guidewire is withdrawn from the distal end (from the tapered element), the distal end may revert to a pre-determined shape.

Figure 15A:
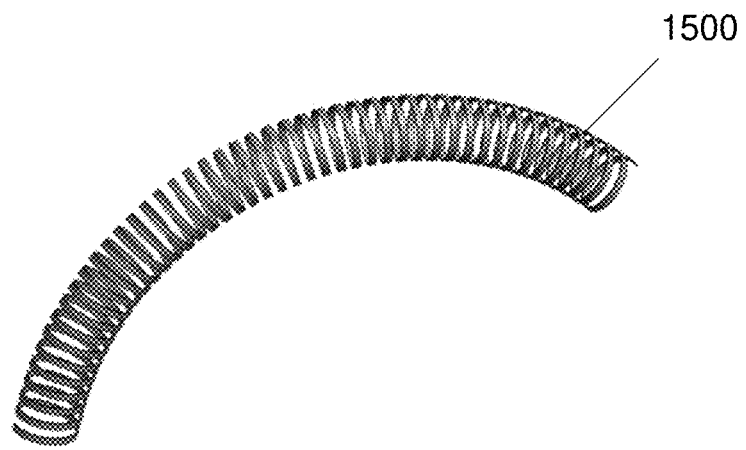
FIG. 15A shows an example distal end of an outer catheter.

FIG. 15A shows an example distal end of an outer catheter. The outer catheter may be any feasible outer catheter, including the outer catheter 130 of FIG. 1A. The outer catheter may include a shape-set coil 1500. The shape-set coil 1500 may provide a pre-determined desired shape to a distal end of the outer catheter. In some examples, the shape-set coil 1500 may be Nitinol, stainless-steel, or any other feasible material. In some examples, the shape-set coil 1500 could be heat set to a desired shape. In some examples, an initial shape of the shape-set coil 1500 may be "more aggressive" (e.g., have more of a curvature or angle) because when the shape-set coil 1500 is laminated to form the outer catheter, some of the curvature or angle may be lost.

In some examples, the shape-set coil 1500 may be transferred to a dowel, shaft, or other form. A low durometer polymer and a thin liner may be applied. The polymer and the liner may enable the shape-set coil 1500 to determine, at least in part, the shape of the distal end of the outer catheter.

In some examples, a hybrid design may include the shape-set coil 1500 and a non-shaped coil. The shape-set coil 1500 may be distally located with respect to the non-shaped coil. In this manner, the distal portion of the outer catheter may be shaped while a proximal portion of the outer catheter may be relatively straight.

Figure 15B:
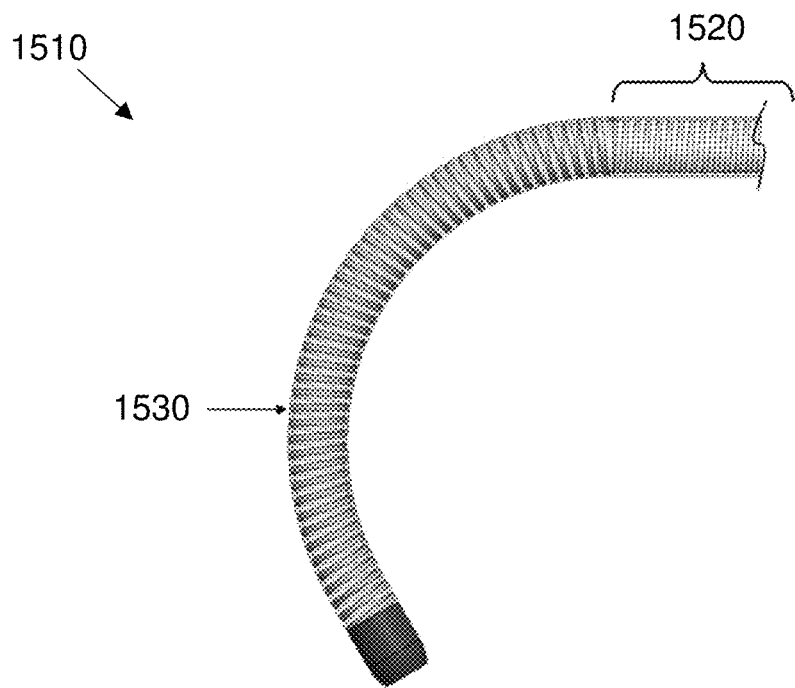
FIG. 15B shows an example distal end of a shaped outer catheter.

FIG. 15B shows an example distal end of a shaped outer catheter 1510. As shown, the shaped outer catheter 1510 may include an unshaped coil 1520 and a shaped coil 1530. The shaped outer catheter 1510 is shown in an unconstrained shape.

Figure 16:
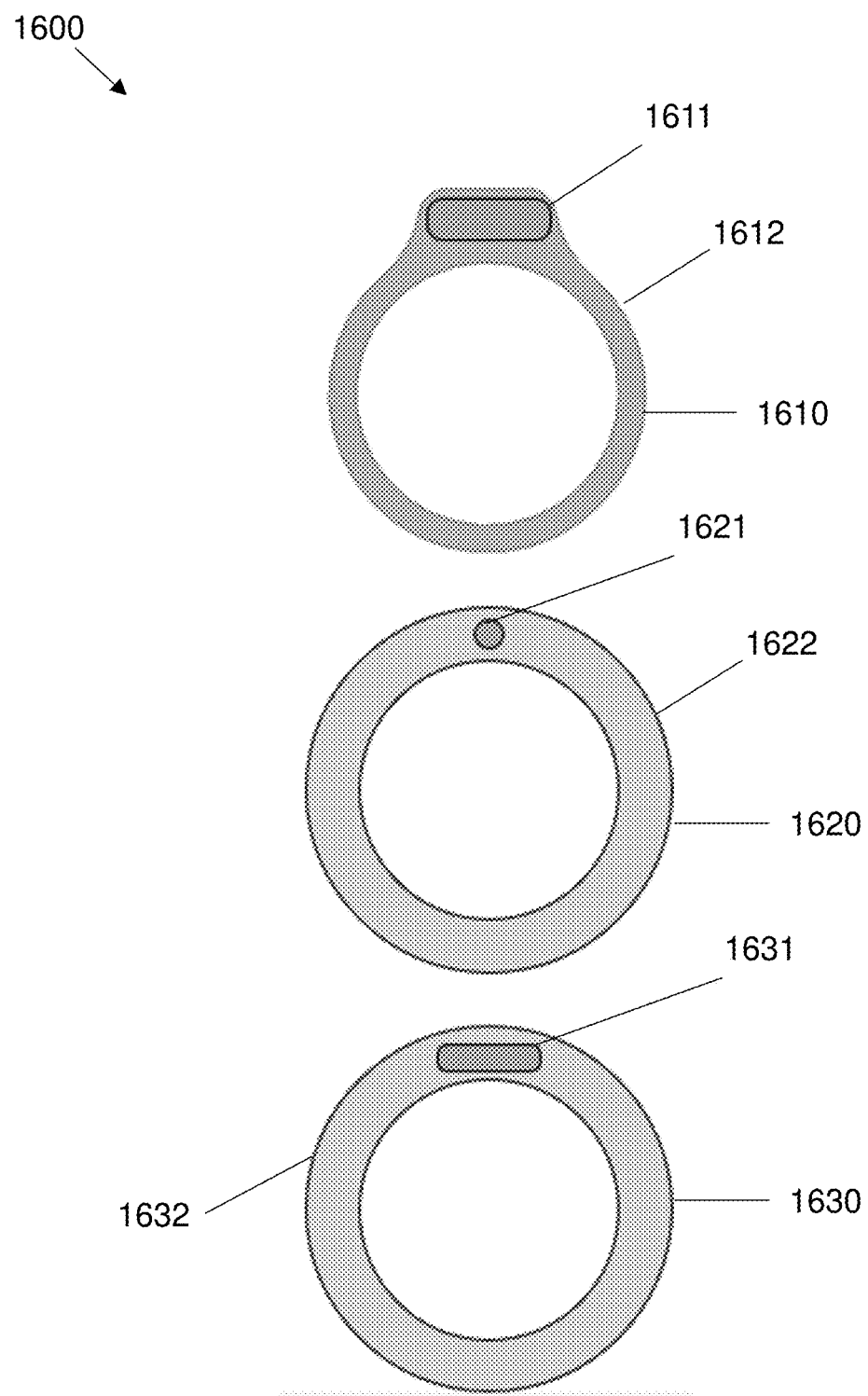
FIG. 16 shows possible cross-sections for an outer catheter.

FIG. 16 shows possible cross-sections 1600 for an outer catheter. As described herein, a shape-set wire may be incorporated into, encapsulated, or laminated within the outer catheter. Cross-sections 1600 includes an example cross-section 1610 with a rectangular (ribbon) shape-set wire 1611 as part of an outer catheter 1612. Example cross-section 1620 includes a round shape-set wire 1621 as part of an outer catheter 1622. Example cross-section 1630 includes a flat (ribbon) shape-set wire 1631 as part of an outer catheter 1632.

In some examples, any of the cross-sections 1600 may include a heat-set polymer to form all or part of the outer catheter. In some examples, any of the cross-sections 1600 may include one more pull-wires to control the shape of the outer catheter. In some other examples, any of the cross-sections 1600 may include a stylet channel.

Figure 17B:
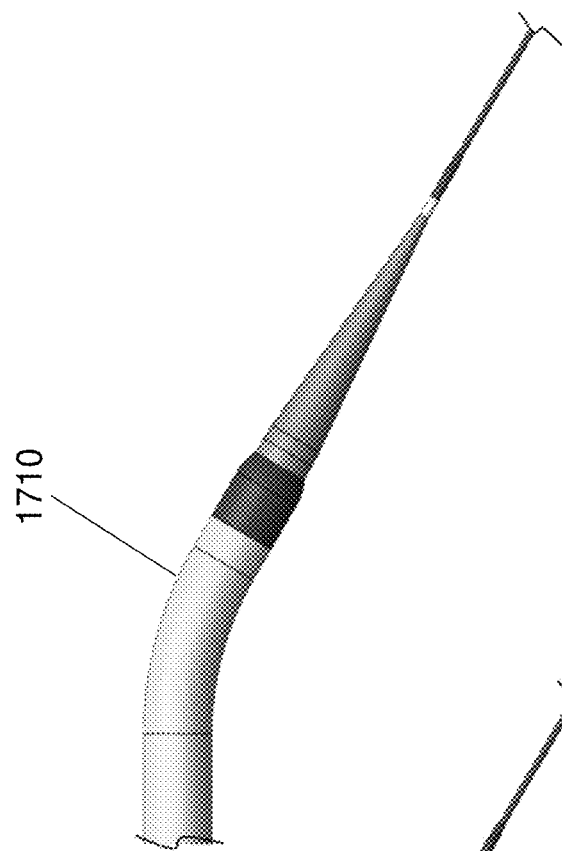
FIGS. 17A-17D show example outer catheter shapes.
Figure 17A:
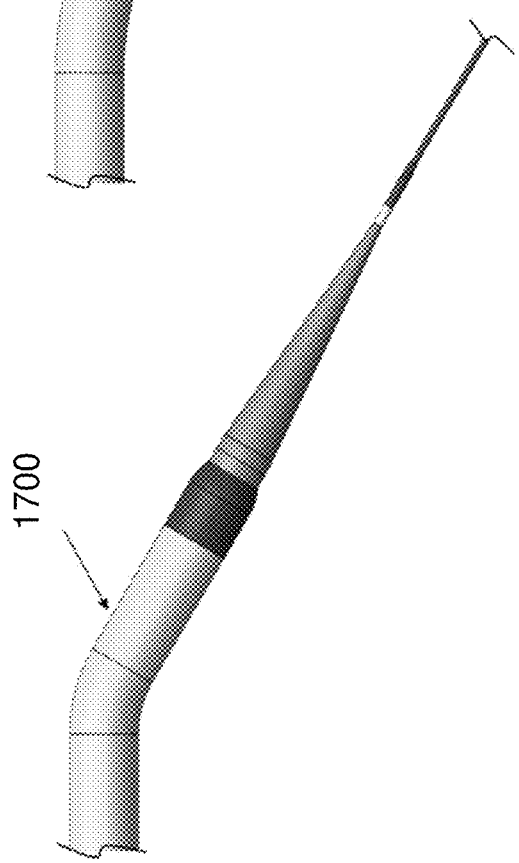
Figure 17C:
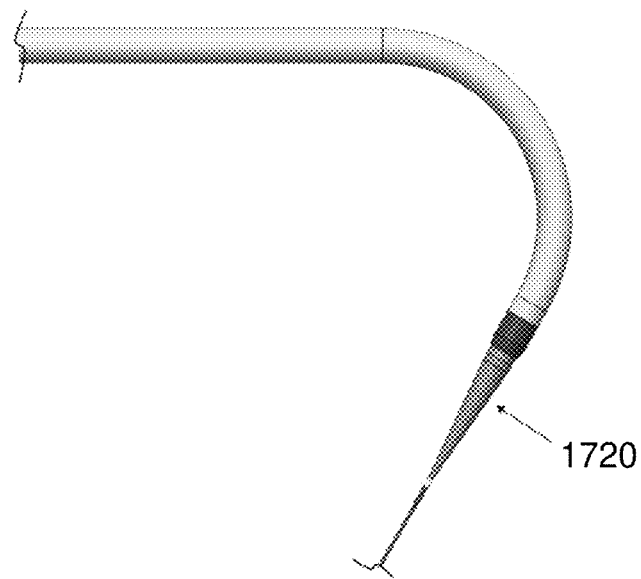
Figure 17D:
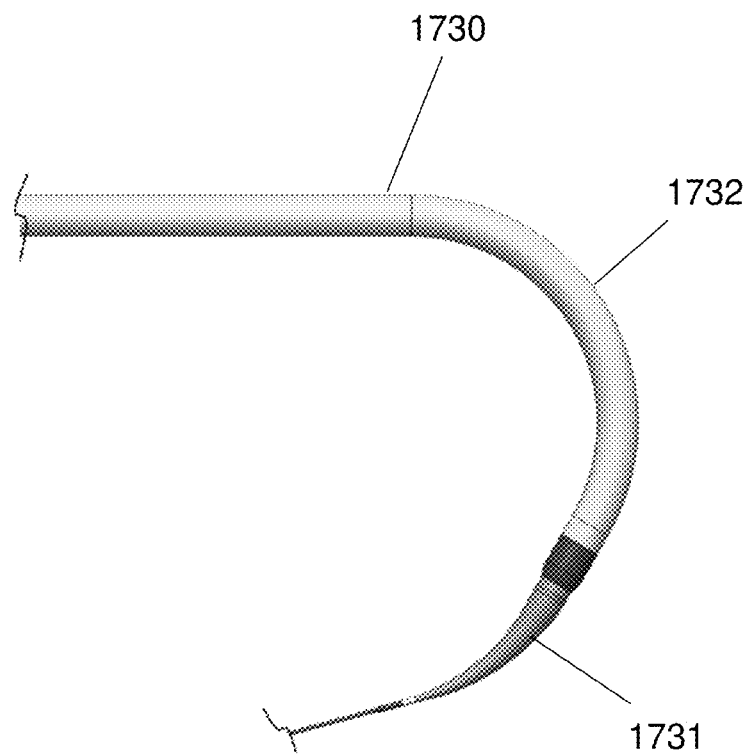

FIGS. 17A-D show example outer catheter shapes. FIG. 17A shows an outer catheter 1700 having 30 degree acute bend. FIG. 17B shows an outer catheter 1710 having a 30 degree smooth bend. FIG. 17C shows an outer catheter 1720 having a smooth 120 degree bend. FIG. 17D shows an outer catheter 1730 having a smooth 120 degree bend along with a distal tip 1731 of an inner catheter 1732 having a 45 degree bend. The examples of FIGS. 17A-17D are meant to be exemplary and not limiting. For example, any feasible combination of bends and/or bend angles are possible.

FIGS. 18A-18L show example steps of using the TAVR apparatus 100 of FIG. 1A to introduce a replacement aortic valve into a patient. The steps described herein are merely exemplary and are not meant to be limiting. Other steps may be used, and in some cases, the steps may be performed in a different order. In particular, the FIGS. 18A-18L show various interchangeable inner catheters being used with the TAVR apparatus 100.

Figure 18A:
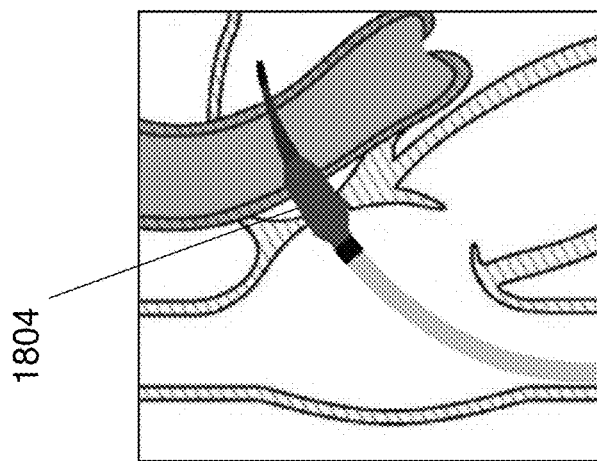
FIGS. 18A-18L show example steps of using the TAVR apparatus 00 of FIG. 1A to introduce a replacement aortic valve into a patient.

In FIG. 18A, a guidewire 1801 is introduced via a transseptal puncture (through an atrial septum) into the left atrium of a heart. For example, the guidewire 1801 may be percutaneously introduced into a patient's femoral artery using, at least in part, the TAVR apparatus 100. The guidewire 1801 may be a 0.035-inch guidewire, however, in other examples, the guidewire 1801 may be other thicknesses or gauges. In some examples, the transseptal puncture may be performed using a radio-frequency device disposed on or near a distal end of the guidewire 1801.

Figure 18B:
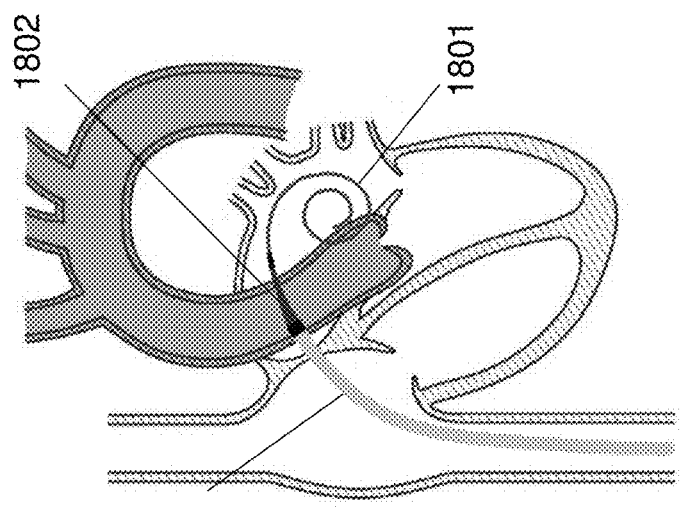

Next, in FIG. 18B, a first interchangeable inner catheter 1802 and an outer catheter 1803 may be advanced to the transseptal puncture. For example, the first interchangeable inner catheter 1802 and the outer catheter 1803 may use the guidewire 1801 as a monorail guide. For example, the first interchangeable inner catheter 1802 may be introduced over the guidewire 1801 and positioned into the inferior vena cava (IVC) and the right atrium. The transseptal puncture may then be performed and the first interchangeable inner catheter 1802 advanced through the puncture. Note that a distal tip of the first interchangeable inner catheter 1802 may be relatively straight.

Figure 18C:
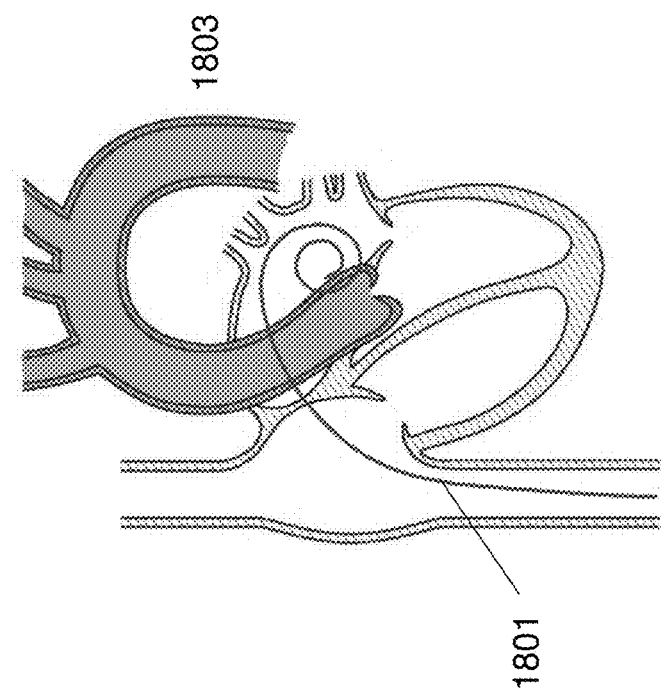

FIG. 18C shows an optional step of a balloon septostomy. In this step, a dilation balloon 1804 may be advanced to the transseptal puncture and inflated to dilate (enlarge) the puncture. In some examples, the dilation balloon 1804 may have an inflated diameter of 6 mm. After the septostomy, the dilation balloon 1804 may be removed. After the dilation, the dilation balloon 1804 may be deflated and withdrawn.

Figure 18F:
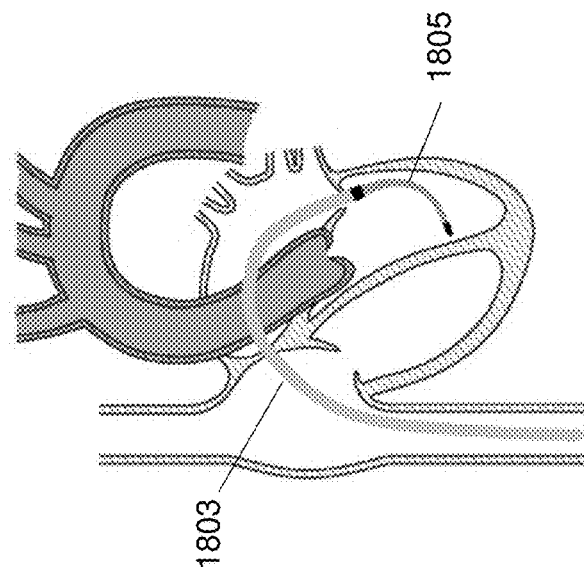
Figure 18E:
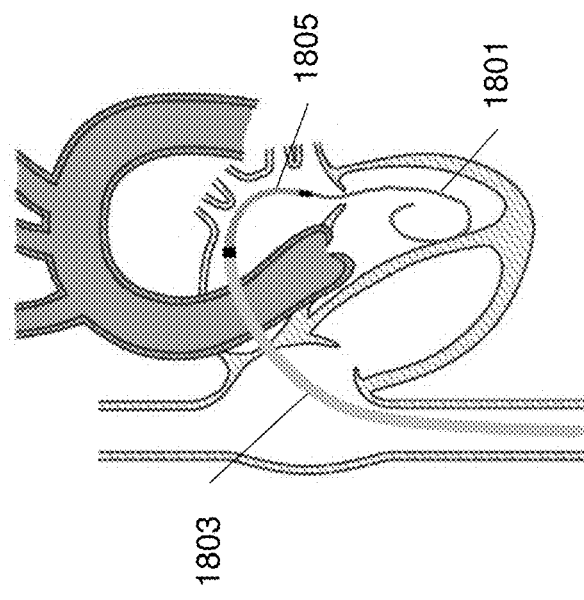
Figure 18D:
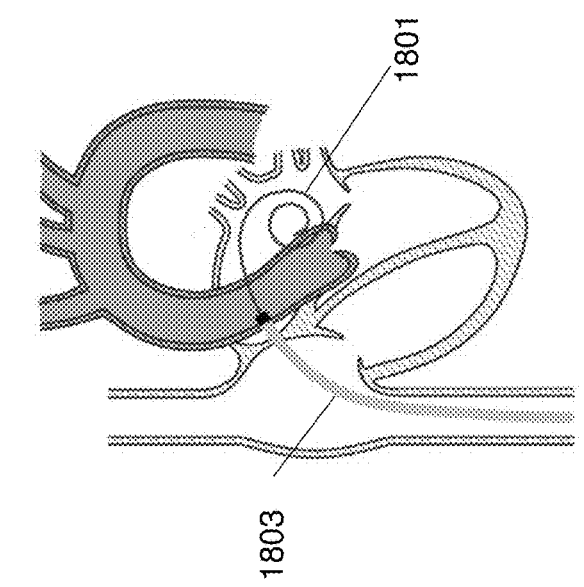

FIG. 18D shows the guidewire 1801 and the outer catheter 1803 in place. For example, the first interchangeable inner catheter 1802 may be unlocked from the outer catheter 1803 and then removed/withdrawn from the patient. As shown, the guidewire 1801 remains in the left atrium.

FIG. 18E shows an introduction of a second interchangeable inner catheter 1805 through the outer catheter 1803. The second interchangeable inner catheter 1805 may include a distal end and/or tip that is curved beyond an angle of approximately 30 degrees. The second interchangeable inner catheter 1805 may be locked (through a lock ring and a coupler, for example) to the outer catheter 1803. The second interchangeable inner catheter 1805 may use the guidewire 1801 as a monorail guide.

FIG. 18F shows the second interchangeable inner catheter 1805 and the outer catheter 1803 advanced through the mitral valve and into the left ventricle. The second interchangeable inner catheter 1805 and the outer catheter 1803 may be guided by the guidewire 1801 (not shown).

Figure 18I:
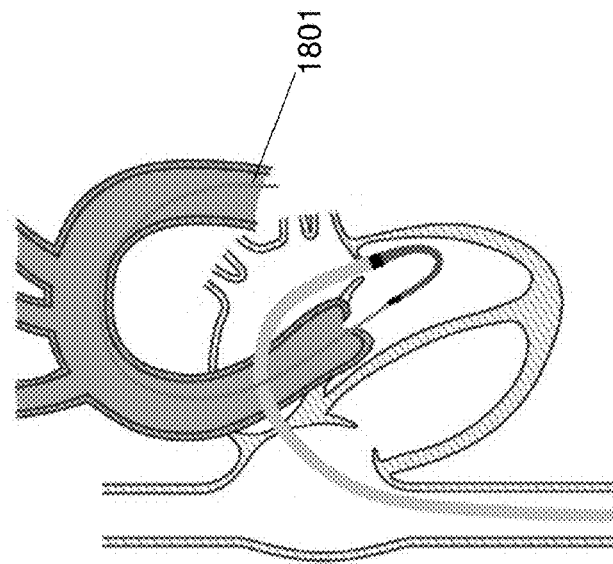
Figure 18H:
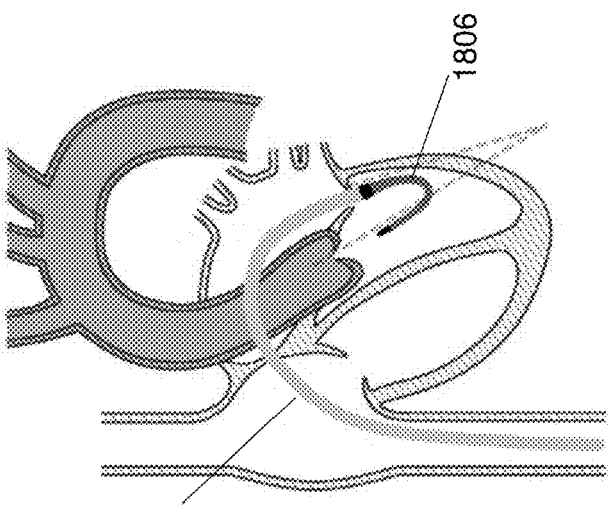
Figure 18G:
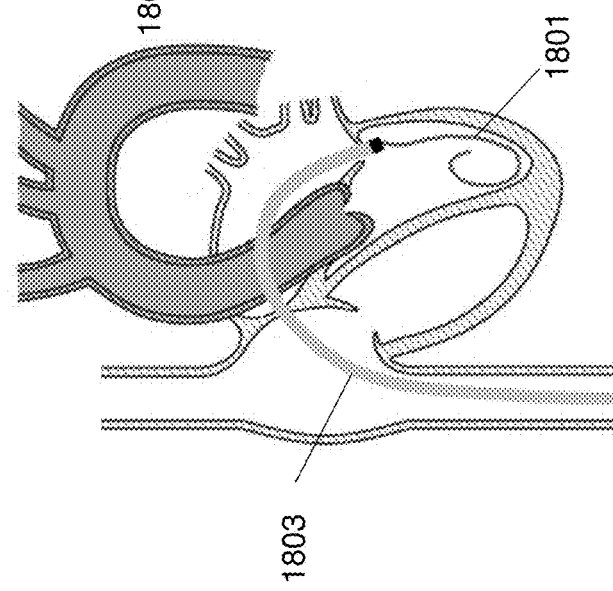

Next in FIG. 18G, the second interchangeable inner catheter 1805 is unlocked from the outer catheter 1803 and withdrawn. The position of the guidewire 1801 and the outer catheter 1803 is maintained in the left ventricle.

FIG. 18H shows a third interchangeable inner catheter 1806 inserted and guided into the left ventricle. The third interchangeable inner catheter 1806 may include a distal end and/or tip that is curved at or beyond an angle of approximately 120 degrees. In some examples, the third interchangeable inner catheter 1806 may be inserted and locked into the outer catheter 1803. In some examples, the guidewire 1801 may optionally be removed. The third interchangeable inner catheter 1806 may be positioned so that a distal end of the third interchangeable inner catheter 1806 may be pointed towards the aortic valve.

FIG. 18I shows the guidewire 1801 advanced distally (antegrade, in the direction of blood flow) through the left ventricle outflow tract (LVOT) and across the aortic valve. In some cases, the guidewire 1801 may optionally be a stiffer guidewire than guidewires used earlier in the procedure (e.g., FIGS. 18A-18G).

Figures 18J, 18K, 18L:
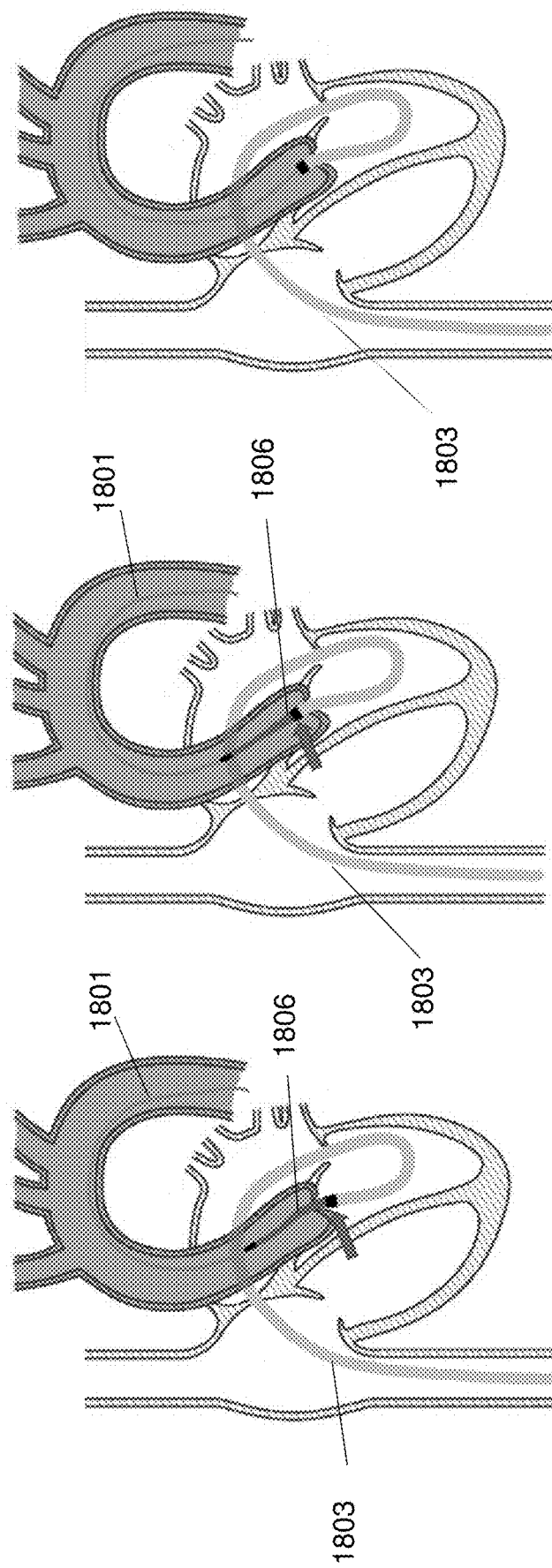

FIG. 18J shows a first optional positioning of the third interchangeable inner catheter 1806 and the outer catheter 1803 within the patient's heart. Note, the curve of the third interchangeable inner catheter 1806 may be straightened, at least in part, by the guidewire 1801. As shown, the distal tip of the outer catheter 1803 may be below the annulus of the aortic valve.

FIG. 18K shows a second optional positioning of the third interchangeable inner catheter 1806 and the outer catheter 1803 within the patient's heart. As shown, the distal tip of the outer catheter 1803 may be advanced across the aortic valve.

FIG. 18L shows the TAVR apparatus 100 as the third interchangeable inner catheter 1806 is withdrawn. For example, the third interchangeable inner catheter 1806 may be unlocked from the outer catheter 1803 and completely withdrawn from the patient. In this position, the outer catheter 1803 is ready to deliver a replacement aortic valve. In some cases, if the distal tip of the outer catheter 1803 is across the aortic valve, the surgeon may optionally withdraw or position the distal tip of the outer catheter 1803 below the aortic valve annulus to assist in positioning and deployment of the replacement aortic valve.

Note that the position of any of the elements of the TAVR apparatus 100 during any steps may be confirmed using any feasible techniques including, but not limited to echocardiography, transesophageal echocardiography, aortic contrast injection, or the like. Positioning of the TAVR apparatus 100 may be enhanced by the embedded and/or included radiopaque elements (e.g., radiopaque markers).

Figure 19:
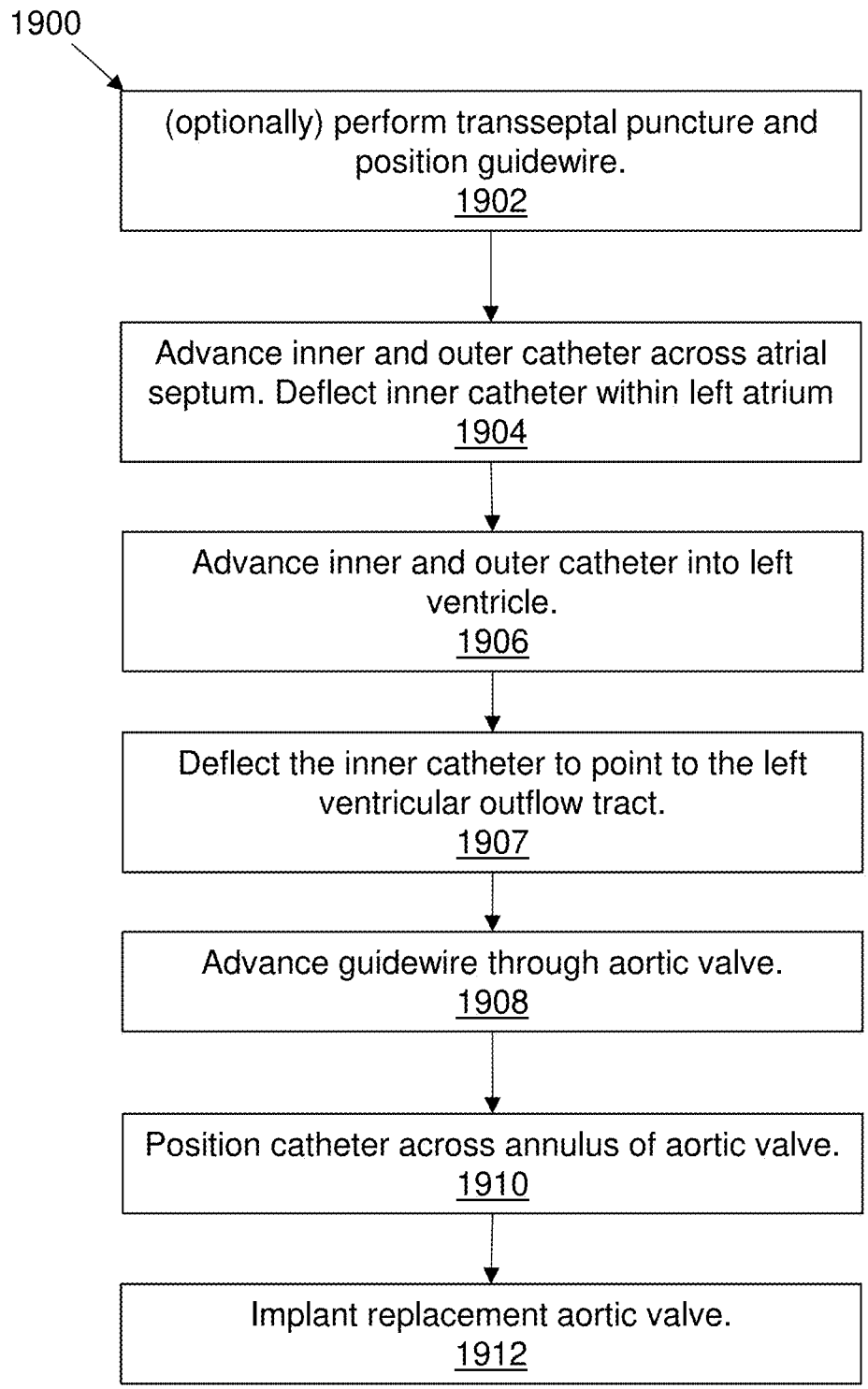
FIG. 19 is a flowchart showing an example method for a transseptal implantation of a replacement aortic heart valve.

FIG. 19 is a flowchart showing an example method 1900 for a transseptal implantation of a replacement aortic heart valve. Some examples may perform the operations described herein with additional operations, fewer operations, operations in a different order, operations in parallel, and some operations differently. The method 1900 is described below with respect to the TAVR apparatus 100 of FIG. 1A, however, the method 1900 may be performed by any other suitable system or device.

The method 1900 may optionally include performing a transseptal puncture. A TAVR apparatus may position a guidewire in the heart 1902. For example, the TAVR apparatus may introduce the guidewire percutaneously into an artery, such as a femoral artery, although the use of other arteries or veins is possible. In some examples, a transseptal puncture may be performed with a radio-frequency device. The TAVR apparatus may be advanced through the atrial septum and positioned within the left atrium of the heart 1904. The inner and outer catheters may be advanced across the atrial septum. For example, the first interchangeable inner catheter may be coupled (locked) to the outer catheter and advanced over the guidewire using the guidewire as a monorail. In some cases, the first interchangeable inner catheter may include a dilation balloon that may be used to expand or enlarge the septal puncture. After dilation, the dilation balloon and/or the first interchangeable inner catheter may be removed. Optionally, the same inner catheter may be used. Either the same or a different inner catheter may be deflected (e.g., bent, turned, angled, etc.) within the let atrium so that that a distal end region of the inner catheter assumes a first bend 1904. The guidewire may then be directed distally from the inner catheter and into the left ventricle.

Next, an inner and outer catheter may be advanced into the left ventricle 1906. For example, the inner and outer catheters may be advanced through the atrial valve. In some examples, a second interchangeable inner catheter 1805 may be inserted and locked within the outer catheter 1803. Alternatively, the same inner catheter may be used (e.g. particularly where the inner catheter is steerable or deflectable to greater than 120 degrees, as described below). In this manner, the inner catheter (or a new inner catheter) and the outer catheter 1803 may be advanced into the left ventricle. Once in the left ventricle, the inner catheter (either the same inner catheter or a new inner catheter) may be deflected within the left ventricle so that the distal end region of this inner catheter assumes a second bend (typically >120 degrees) and faces the left ventricular outflow tract 1907.

The guidewire may then be advanced through the aortic valve 1908. In some examples, the guidewire may be advanced through the aortic valve and into the aorta. Furthermore, in some examples, the inner catheter used in the previous step may be removed and replaced with another interchangeable inner catheter.

The catheter may then be advanced and positioned across the annulus of the aortic valve 1910. For example, the inner catheter and the outer catheter may be positioned at or near the annulus of the aortic valve (or in some examples, across the aortic valve. In some examples, the distal end of the outer catheter may be above the annulus of the aortic valve. In some other examples, the distal end of the outer catheter may be below the annulus of the aortic valve.

The guidewire (or a second guidewire having a different stiffness) may be advanced out of the distal end of the inner catheter and across an aortic valve of the patient's heart.

A replacement aortic valve may then be implanted 1912. In some examples, the inner catheter may be unlocked and withdrawn from the outer catheter prior to the placement and implantation of the replacement aortic valve.

FIGS. 20A and 20B illustrate another example of a system 2000 for antegrade delivery of a replacement aortic valve. In this example, the system includes an outer catheter, and an inner catheter. The inner catheter is inserted into an outer catheter hub 2021 (as shown in FIG. 20A) of the outer catheter 2030. The inner catheter 2040 in this example, is deflectable or bendable at a distal end region (shown in FIG. 20B). Deflection may be controlled by actuation of a deflection control 2056 on the inner catheter deflection handle 2055. In this example, moving the control forwards or backwards (shown by arrow 2057) may deflect the deflectable region 2061 of the inner member that is distal to the coupling region 2063 to the outer catheter, but proximal to the distal (tapered) end 2065 of the inner catheter. In this example, the inner catheter, when coupled to the distal end of the outer catheter, is configured to deflect more than 120 degrees (e.g., in FIG. 20B, the deflection is greater than 180 degrees, as shown by the arrow 2058). Thus, the bend region 2061 between the engagement surface and the distal end that is configured to assume a bend of greater than 120 degrees. In some examples the bending may be actuated by a wire or tendon (e.g., a pull wire) that may extend through the inner catheter or through a wall of the inner catheter. Any appropriate actuating mechanism may be used. For example, the catheters described herein may be tendon driven catheters, magnetic navigation catheters, soft material driven catheters (e.g., shape memory effect catheters, steerable needles, concentric tubes, conducting polymer driven catheters and hydraulic pressure driven catheters, etc.), and hybrid actuation catheters. These catheters may have single sections or multiple sections As shown in FIG. 20B, the distal end region of the inner catheter is tapered 2065, and a proximal region of the inner catheter includes an engagement surface that is proximal to a distal end of the inner catheter, wherein the engagement surface forms part of the coupling region 2063 that is configured to detachably and sealingly couple to a distal end region of the outer catheter 2030 so that an outer surface of the first inner catheter is flush with an outer surface of the outer catheter without a gap.

The example shown in FIGS. 20A-20B is just one example of an inner catheter; other examples may include smaller bending angles (e.g., between 20-90 degrees, between 30-90 degrees, etc.). The outer catheter may also be steerable.

FIG. 21 illustrates one example of a method using a system including a steerable inner catheter such as the one shown in FIGS. 20A-20B. in this example the system is shown with the inner and outer catheter extending from the antegrade direction (e.g., through a septal opening, into the left atrium, then the left ventricle) similar to that shown in FIGS. 18A-18L. A relatively stiff guidewire 2110 is shown extending from the inner catheter 2140 and into the ascending aorta. The inner and outer catheters (coupled together as shown) may be advanced so that the outer catheter is adjacent to the aortic valve, but and the inner catheter may then be removed, leaving the outer catheter in position to deliver (along with the guidewire) the replacement valve. As mentioned above, in any of these examples the outer catheter (which may also be referred to as an outer sheath) could be delivered either through the diseased aortic valve or placed just proximal to the lower surface of the aortic valve. Thus, the guidewire may be extended across the valve and the replacement valve may be pushed across, without driving the sheath across the valve.

Although the examples shown above and in FIGS. 18A-18L illustrate methods for replacing an aortic valve, similar techniques may be used for replacement of a mitral valve from an antegrade approach. For example, the same basic steps may be followed as described above, but the outer and inner catheter may be advanced just to the mitral valve (e.g., without the need to deflect the inner catheter within the left ventricle. For example, a variation of FIGS. 18A-18G may be performed, leaving the distal end of the outer catheter adjacent to or through (e.g., beyond) the mitral valve. After delivery of the outer catheter (e.g., sleeve), a percutaneous mitral valve interventional device (e.g., a mitral valve replacement device, a mitral valve repair device, a clip, etc.) may be advanced, positioned and deployed through outer catheter to the mitral valve or the region proximate to the valve.

In general, the methods and apparatuses described herein may include one or more features that enhance their use for replacement of a valve. For example, the inner catheter(s) may be configured for rapid exchange over the guidewire (e.g., monorail) while the outer catheter does not, but is a full catheter. In general, the inner and outer catheters may sealingly lock onto each other as described, and the inner catheter may be steered when locked (and extending distally from) the outer catheter so that the inner catheter may be freely steered, without interference from the outer catheter, while the outer catheter remains locked onto the inner catheter in a predictable and safe manner. In addition, the inner catheter may have a steeply tapered distal end (e.g., from 3 F to 20 F in some examples); this tapered region may be relatively short (e.g., may extend about 4 cm or less, about 3.5 cm or less, about 3 cm or less, about 2.5 cm or less, about 2 cm or less, about 1.5 cm or less, etc.) which may both prevent damage to the tissue and may allow maneuvering within the heart. Further, in the steerable inner catheters, the deflecting region may stop proximally to the distal end of the inner catheter, so that the distal, highly flexible tip can track the guidewire. For example, the steerable region may end about 4-5 mm back from the distal tip. In general, the apparatuses and methods described herein are configured to prevent scraping, which may otherwise damage the vessel, and my cause the release of material (e.g., clot, plaque, calcified material, etc.) from the valve and/or wall(s) of the heart.

Filters

Figure 22A:
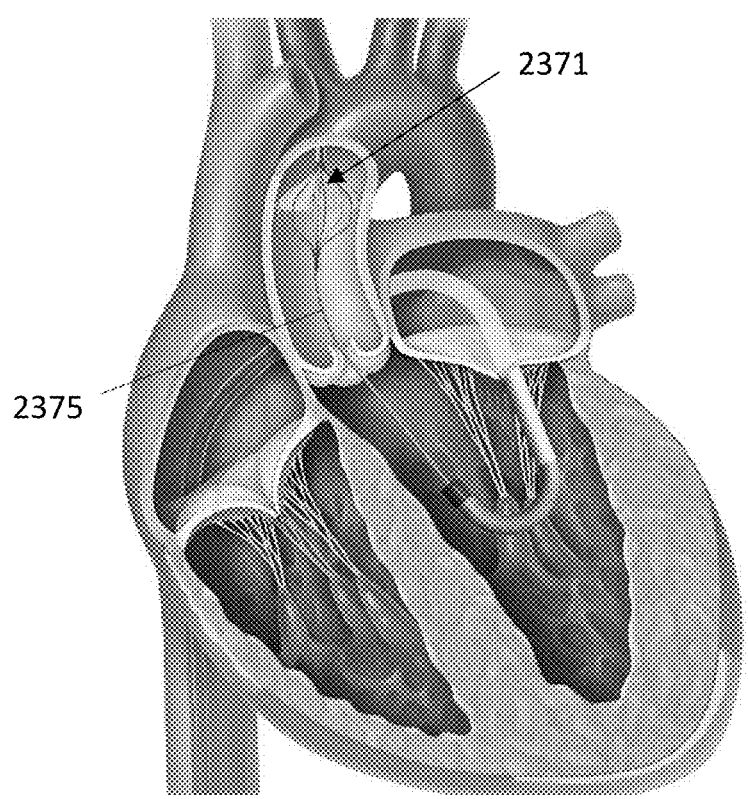
FIG. 22A shows one example of a method of using a system including a filter (e.g., filter wire or filter on a wire) that may be used with any of the methods and apparatuses described herein.

In general, any of the apparatuses and methods described herein may include one or more filters that may be configured to be positioned distally from the apparatus as it is positioned (or after it is positioned) relative to the valve. The filter 2371 may be a filter wire, such as the one shown in FIG. 22A, which is configured to capture loose material during valve positioning and deployment. FIG. 22A illustrates the placement of a filter 2371 as part of a system as described above. For example, a filter may be coupled to a wire 2375 (e.g., a 0.035" wire) and may be deployed into the ascending aorta, to catch debris from valve deployment and replacement. The filter may be self-expanding and may be deployed as part of a guidewire (e.g., attached to the guidewire), or applied using (e.g., over) the guidewire, or adjacent to the guidewire, and may be advanced into position in a collapsed configured with a sheath (not shown) over the self-expanding filter 2271. Once in position distal to the distal end of the outer catheter and further antegrade, the filter sheath may be removed, and the filter deployed as shown. Once deployed, the filter may capture any debris arising from the procedure. Following the procedure, the filter may be removed, e.g., re-sheathed, and withdrawn to remove any captured debris.

In some examples the filter wire may act as the 0.035' guide wire to deliver the valve. In some examples, the filter may be deployed into the ascending aorta and the sheath for the filter may be completely removed (e.g., pulled all the way out of the body) so that the replacement valve (e.g., TAVR valve) may be advanced over the filter wire. Once the valve is deployed, debris can be caught in the filter, which can be removed to retrieve the filter and any debris that was captured during the procedure, in order to reduce the risk of embolic embolization to the intracerebral blood vessels of other more distal arteries.

Any appropriate wire for the filter wire and/or guidewire may be used. For example, in some cases the distal end of the wire may be, e.g., an A 3J guidewire (e.g., the distal end may have a pre-set curve or shape) and may be any appropriate length. In some examples the filter region may be mounted or poisoned on a region that is proximal to the distal end. For example, the 15 cm proximal to tip of wire may include a filter mounted on wire. The filter may be, for example, an expandable nitinol filter that may be delivered constrained by an outer sheath. Pulling the sheath may expand the filter (e.g., to 3 cm or larger diameter) and in some examples may contact a wall of the ascending aorta, e.g., approximately 8 cm above valve but before first branch of the aortic arch). Thus, any of the methods and apparatuses described herein may include the user of a filter (and antegrade filter) as described.

Alternatively, or additionally, the wires (e.g., filter wires, guide wires, etc.) may also be used to deliver contrast distally to the proximal aorta (e.g., a contrast-deploying guidewire). For example, any of the wires described herein (e.g., guidewires, filter wires, etc.) may be hollow and may include one or more distal openings (holes, slits, etc.) through which contrast may be applied. For example, any of these apparatuses may include a wire to deliver contrast (and optionally to deliver and/or control a filter). In some examples the wire may include one or more side holes in the wire, so that contrast may be delivered from out of the side holes; for example, a syringe may be applied to the proximal end of the wire and contrast may be injected through the wire. The contrast may be delivered this way with or without the use of a filter. Alternatively, or additionally, contrast may be applied through the outer catheter to assist in the accurate placement of the valve.

Figure 22B:
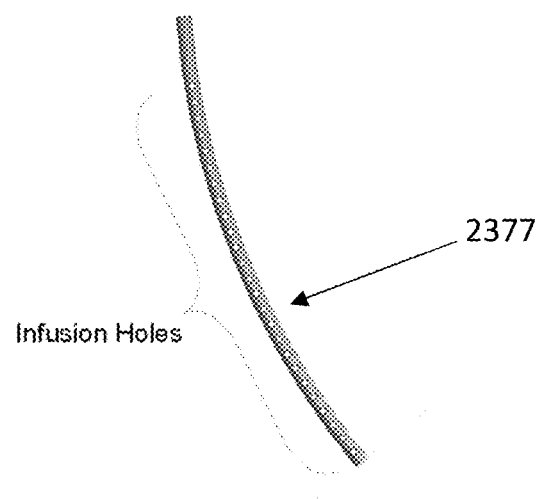
FIG. 22B shows an example of a wire (e.g., guidewire) including infusion openings along a region of the length of the wire.

FIG. 22B illustrates an example of a contrast-deploying guidewire 2377 that includes a plurality of infusion holes 2379 arranged down a length of the side of the guidewire. The distal tip region of the contrast-deploying guidewire may be solid (e.g., does not allow contrast material to pass out of the distal end). Alternatively in some examples the distal tip region may be open instead or as well as the side openings. The length of the region of the contrast-deploying guidewire that includes the plurality of openings may be, e.g., between 0.5 cm and 10 cm (e.g., 0.5 cm or more, 0.75 cm or more, 1 cm or more, 1.5 cm or more, 2 cm or more, 3 cm or more, 4 cm or more, 5 cm or more, between about 0.5-10 cm, between about 0.5-8 cm, between about 0.5-7 cm, between about 0.5-6 cm, between about 0.5-5 cm, between about 0.5-3 cm, etc.). The solid distal tip region of the contrast-deploying guidewire may extend any appropriate length (e.g., about 0.5 cm or less, about 1 cm or less, about 2 cm or less, about 3 cm or less, about 4 cm or less, about 5 cm or less, between about 0.5-10 cm, between about 1-8 cm, between 0.5-7 cm, between about 0.5-6 cm, between about 0.5-5 cm, etc.).

The contrast-deploying guidewire may be formed of any appropriate material, including polymeric and/or metal (e.g., stainless steel, Nitinol, etc.) materials.

Expandable Deflectors

The methods and apparatuses for replacing a valve described herein may include an expandable deflector to deflect the chordae tendinae in order to prevent entangling any of the components (e.g., guidewire, inner catheter(s), outer catheter, etc.) in the chordae tendinae during the procedure. For example any of the methods an apparatuses described herein may include an expandible deflector that is configured to deflect the chordae tendinae, to prevent damaging the valve and/or the chordae tendinae, including preventing cutting the chordae tendinae which may otherwise result in mitral regurgitation.

An expandable deflector may include any expandable member, such as a balloon, basket, mesh, etc. that may be controllably expanded and contracted. In some examples the apparatuses may include one or more expandable deflectors on a distal end region of the guidewire, an inner catheter, and/or an outer catheter. The expandable deflector may be expended before, during or shortly after inserting the apparatus into the ventricle (e.g., left ventricle) as described above, to displace away from the chordae tendinae, away from the apparatus and to prevent the apparatus from being caught between a chordae tendinae and the wall of the ventricle. In some examples the expandable deflector may act to center the apparatus within the mitral apparatus and/or the left ventricle.

Figure 24A:
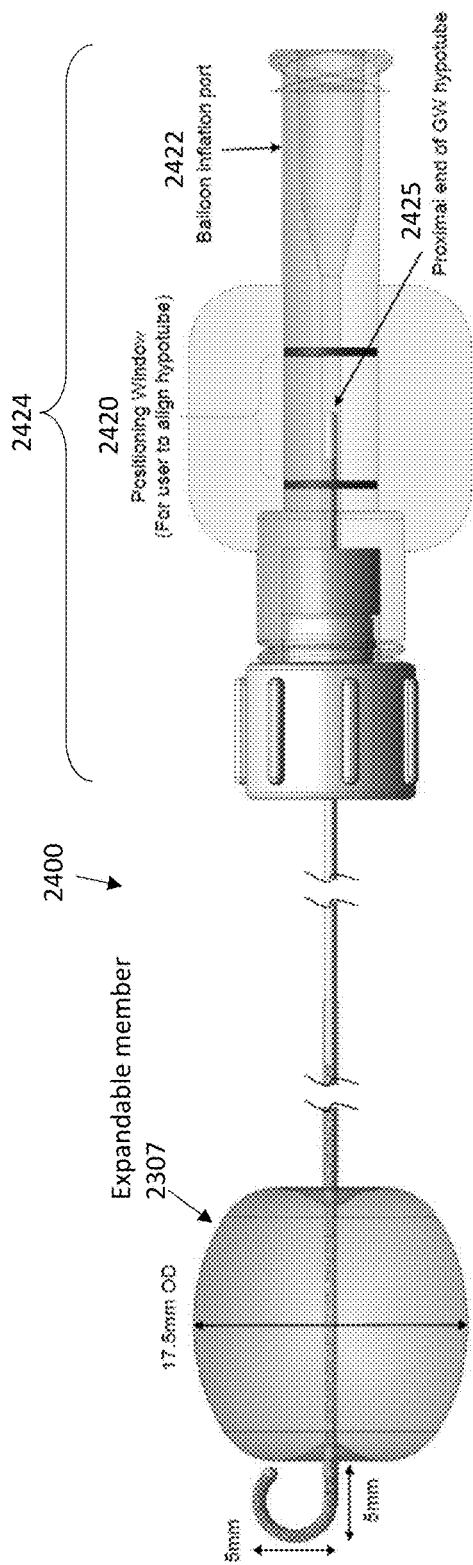
FIG. 24A illustrates the mitral valve centering guidewire of FIGS. 23A-23C with the expandable deflector expanded and also includes the proximal end region.

FIGS. 23A-23C illustrate a first example of an apparatus including an expandable deflector. FIG. 23A shows a guidewire 2300 including an expandable deflector 2307 configured as a compliant balloon, that extends over a distal region of the apparatus. In FIG. 23A the guide wire is configured as a mitral valve centering guidewire. The expandable deflector 2307 may be expanded (as shown in FIG. 24A) to deflect away from the chordae tendinae when in the ventricle. In FIG. 23A, the guidewire has a diameter of approximately 0.035" and has a J-shaped tip (J-tip) 2305, which may be atraumatic and may include a radiopaque marker. The expandable member may be formed of a compliant tube forming the balloon that is coupled to the outer surface of the guidewire by a polymer jacket 2309. A more proximal outer surface region 2311 of the guidewire may be configured to have a textured surface that may provide added grip for the inflation hub Tuohy region, shown in FIG. 24B.

As shown in the sectional view of FIG. 23B, the guidewire may be cut (e.g., laser-cut) in the distal end region 2313 to increase and/or enhance flexibility. The guidewire in this example may be formed of a hypotube 2315 that may be laser cut and coated, laminated, or otherwise configured to seal the inner lumen, so that the inner lumen of the hypotube may be configured as an inflation lumen for inflating the expandable deflector (e.g., balloon). For example, as shown in FIG. 23C, the guidewire may be a cut hypotube that is sealed by a laminated polymer jacket 2327. FIG. 23C shows a slightly enlarged view of the guidewire distal section shown in FIG. 23B. In FIG. 23C, the distal tip 2317 is shown as an atraumatic distal tip that is attached (e.g., soldered, welded, etc.) to a J-shaped distal region 2319 that may include a shape-set inner core (e.g., nickel titanium inner core) to have a J-shape. The distal end (J-shape) may be hermetically welded between the hypotube and a core wire 2321, as shown in this example, The expandable deflector 2307 may be expanded by filling it with inflation fluid that may flow through and into the inner lumen of the guidewire. The distal end 2329 of the expandable deflector and the proximal end of the expandable deflector 2325 may be sealed to the guidewire as shown.

Figure 24B:
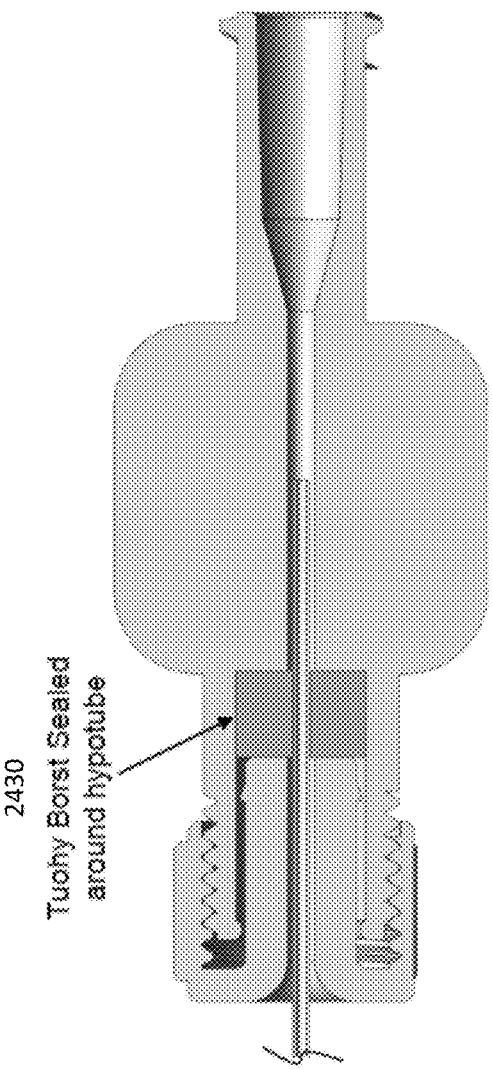
FIG. 24B shows a section view of a proximal hub that may couple to the proximal end region of FIG. 24A (For inflating/deflating of the expandable deflector).

FIG. 24A shows an example of a guidewire apparatus 2400 similar to that shown in FIGS. 23A-23C. As shown in FIG. 24A, the expandable member 2307 may be expanded, e.g., to between about 4 mm and about 25 mm (e.g., between about 12 mm and about 20 mm, etc.). FIG. 23C is a slightly enlarged view of the device of FIGS. 23A-23B with the expandable deflector (e.g., balloon) in a collapsed configuration. FIG. 24A also includes a proximal end 2425 that may be coupled to a sealing removable inflation hub with a rotating Tuohy Borst seal 2424 (which may be used as a handle). The hub in this example may include a positioning window 2420 for aligning the guidewire, as well as an inflation port 2422 (e.g., balloon inflation port). FIG. 24B shows an enlarged view of this handle (inflation hub with a rotating Tuohy Borst seal 2424) of FIG. 24A, including the Tuohy Borst seal 2430 sealed around the guidewire's proximal end region.

Figure 25A:
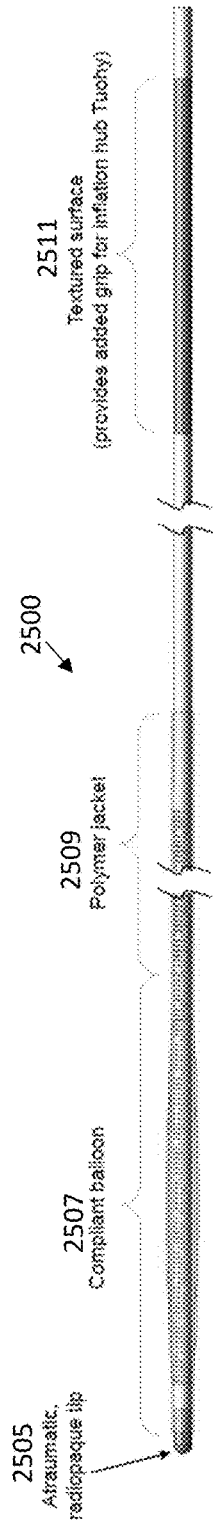
FIGS. 25A-25D illustrate an example of a mitral valve centering guidewire including an expandable deflector. This example is a 0.035" diameter centering guidewire having a straight tip.
Figure 25B:
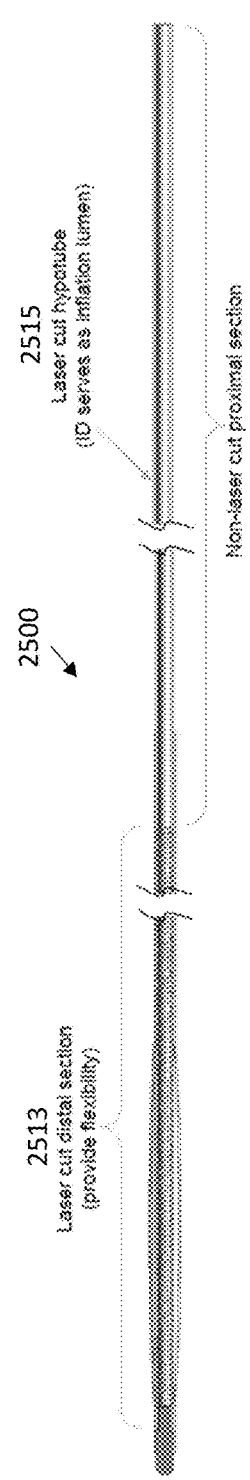

FIGS. 25A-25D illustrate another example of a guidewire including an expandable deflector 2507 (also configured as a compliant view in this example). As shown in FIG. 25A, the guidewire 2500 of FIGS. 25A-25D has a straight distal end 2505 (shown as an atraumatic, radiopaque tip) rather than the J-shaped distal end region of FIGS. 23A-23C. The other features may be the same, however, including the polymer jacket region 2509, and proximal textured surface 2511. As describe above for FIGS. 23A-23C, the guidewire may be formed of a hypotube 2515 that may be cut (e.g., laser cut) to increase flexibility of the distal end region 2513.

Figure 25C:
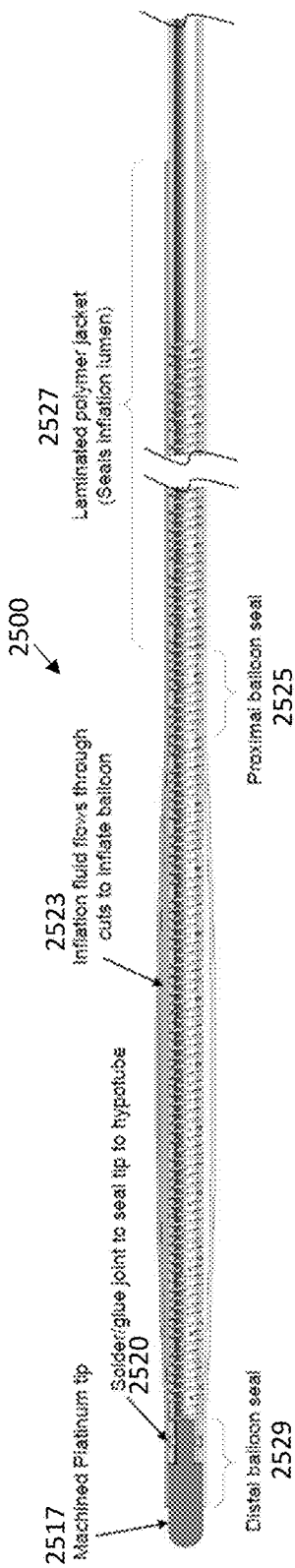
Figure 25D:
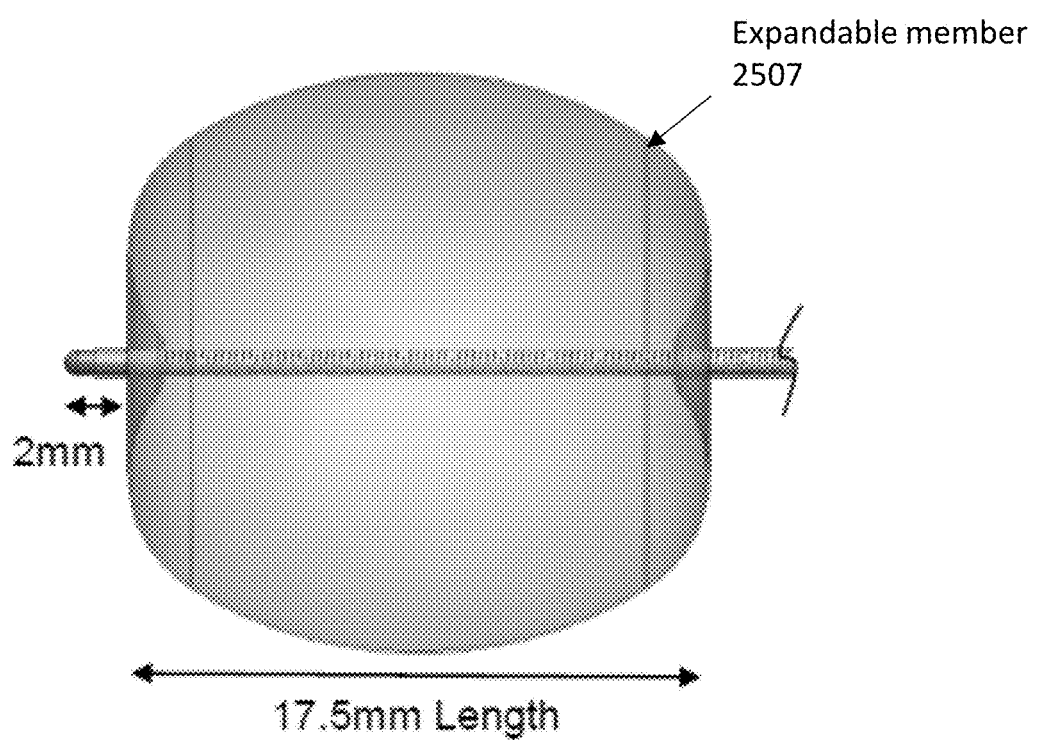

The guidewire 2500 may also include a machined platinum tip 2517, which may be an atraumatic tip, and a solder/glue joint 2520 coupling the seal tip to the hypotube. The expandable deflector may be inflated by injecting a fluid 2523 through the hypotube to inflate the balloon 2507 (as shown in FIG. 25D). The balloon may be seated in fluid communication with the lumen of the guidewire at a proximal balloon seal 2525 and a distal balloon seal 2529. As mentioned, the laser cut hypotube may be sealed, e.g., by laminating a polymeric jacket over the laser cut hypotube 2527 as illustrated in FIG. 25C.

Figure 26A:
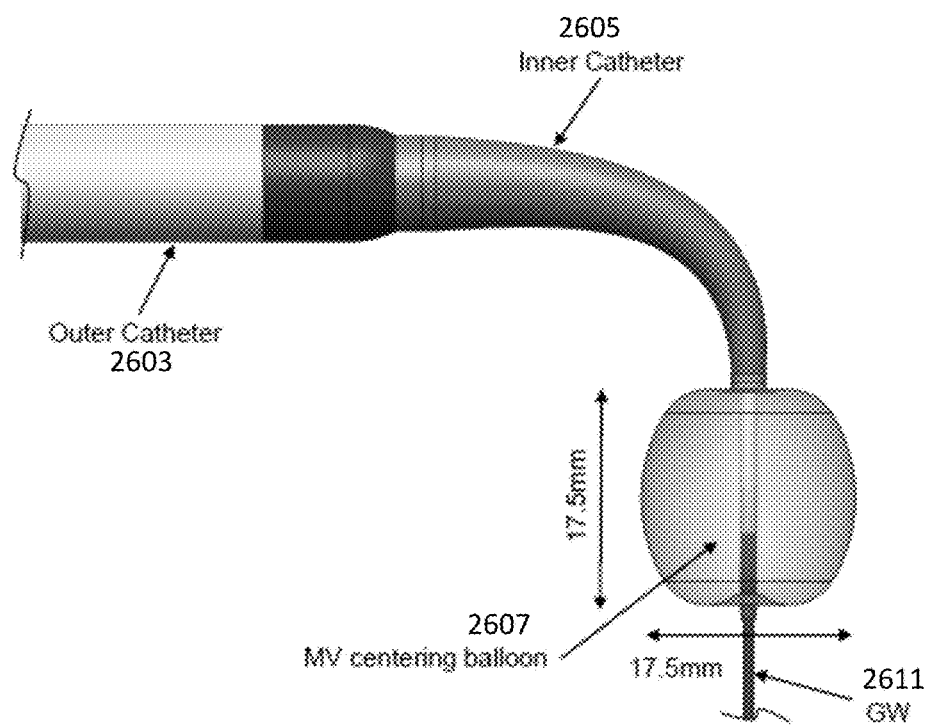
FIGS. 26A-26C illustrates an example of an inner catheter including an expandable deflector.
Figure 26B:
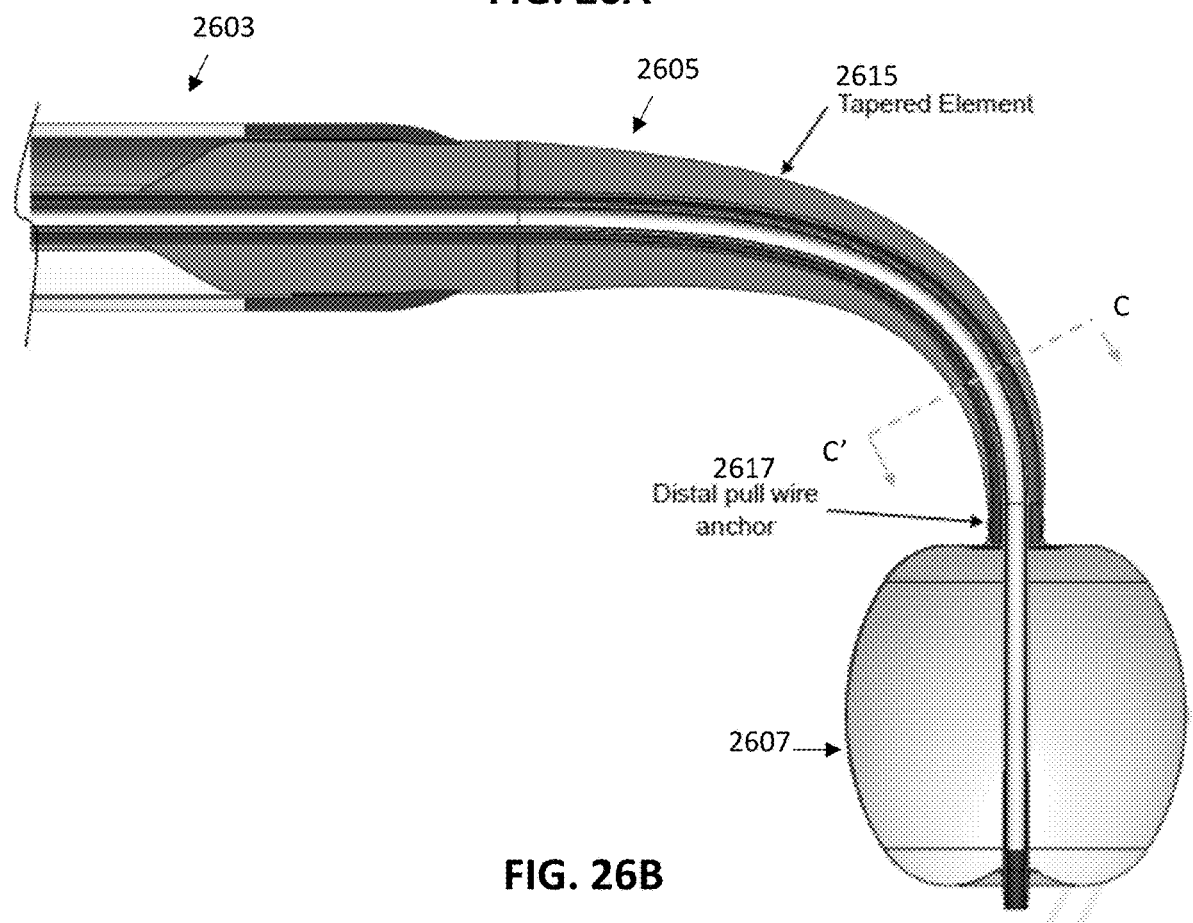
Figure 26C:
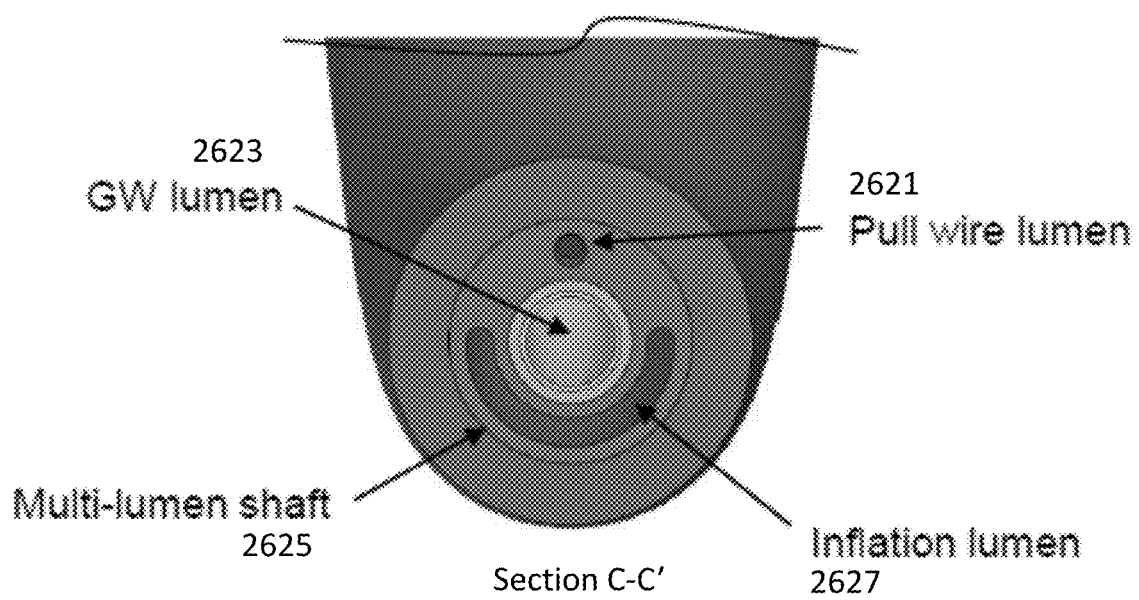

FIGS. 26A-26C illustrate an example of an inner catheter 2605 including an expandable deflector 2607. As shown in FIG. 26A, the inner catheter ay be engaged with an outer catheter 2603, as discussed above. The expandable deflector (balloon 2607) may be positioned at a distal end region of the inner member and may be in fluid communication with an inflation lumen 2627, as shown in FIG. 26C. The distal end region of the inner catheter of FIGS. 26A-26C may be bendable or steerable using a pull wire within a pull wire lumen 2621; the distal end of the pull wire may be anchored 2617 within the distal end region, as shown in FIG. 26B. A guidewire 2611 may extend into and out of a guidewire lumen 2623. Thus, the inner catheter in this example may include a multi-lumen shaft 2625.

Figure 27A:
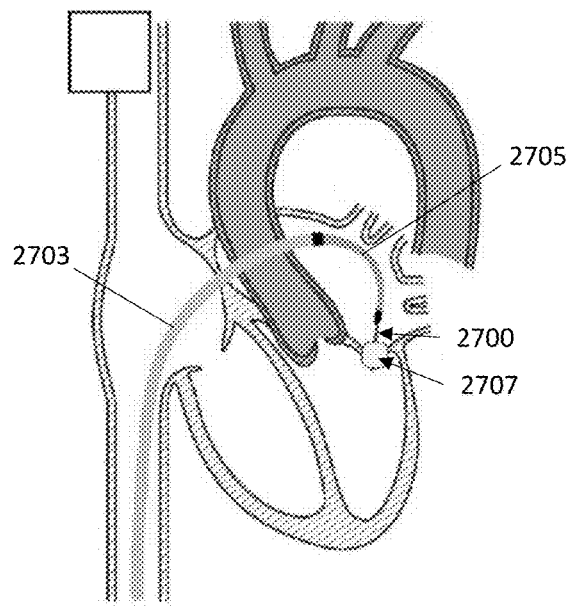
FIGS. 27A-27B illustrate an example of a method of deflecting away from the chordae tendinae using a guidewire having an expandable deflector (similar to that shown in FIGS. 25A-25C).
Figure 27B:
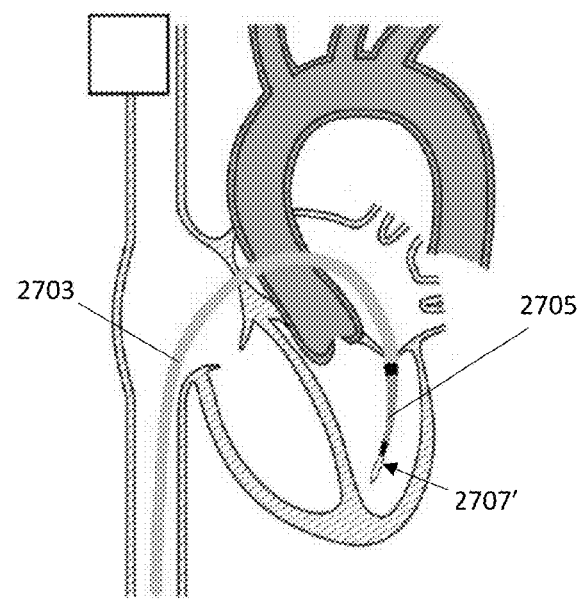

In operation the chordae tendinae of the ventricle may be avoided as part of any of the methods described herein for valve replacement. For example, FIGS. 27A-27B illustrate the use of a guidewire 2700 with an expandable deflector 2707 similar to that shown in FIGS. 25A-25D. The expandable deflector 2707 may be inflated while at the mitral valve or just proximal to the mitral valve, or in some examples just distal to the mitral valve. In some examples inflation of the expandable deflector may help advancing and centering of the guidewire, avoiding the chordae tendinae. For example, expansion of the expandable deflector may also allow the expandable deflector to be drawn into the ventricle and to the valve during diastole, as it may act as a sail to and the flow of blood within the ventricle may draw the expanded deflector forward. The expandable member may be deflated 2707' once positioned, or in some examples may be left inflated while performing other steps of the method.

Figure 28A:
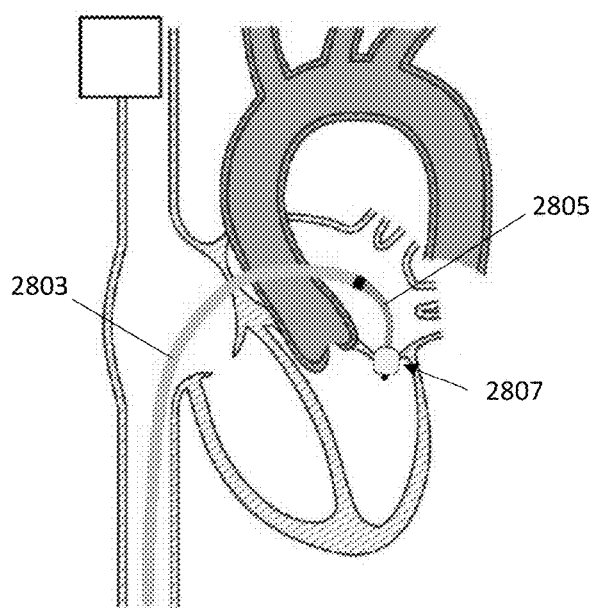
FIGS. 28A-28B illustrate an example of a method of deflecting away from the chordae tendinae using an inner catheter having an expandable deflector (similar to that shown in 26A-26C).
Figure 28B:
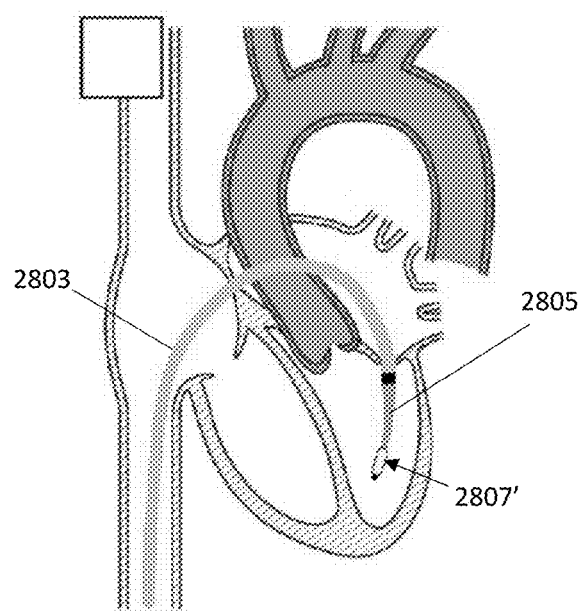

FIGS. 28A-28B illustrate the same operation using an inner catheter 2805 (extending from an outer catheter 2803) including an expandable deflector 2707 similar to that shown in FIG. 27A-27B. In FIG. 28B the expandable deflector 2807' is shown unexpanded.

In any of the figures shown herein, the dimensions may be illustrative only, and other dimensions may be used (e.g., +/−5%, 10%, 15%, 20%, 25%, 50% or more).

Figure 29:
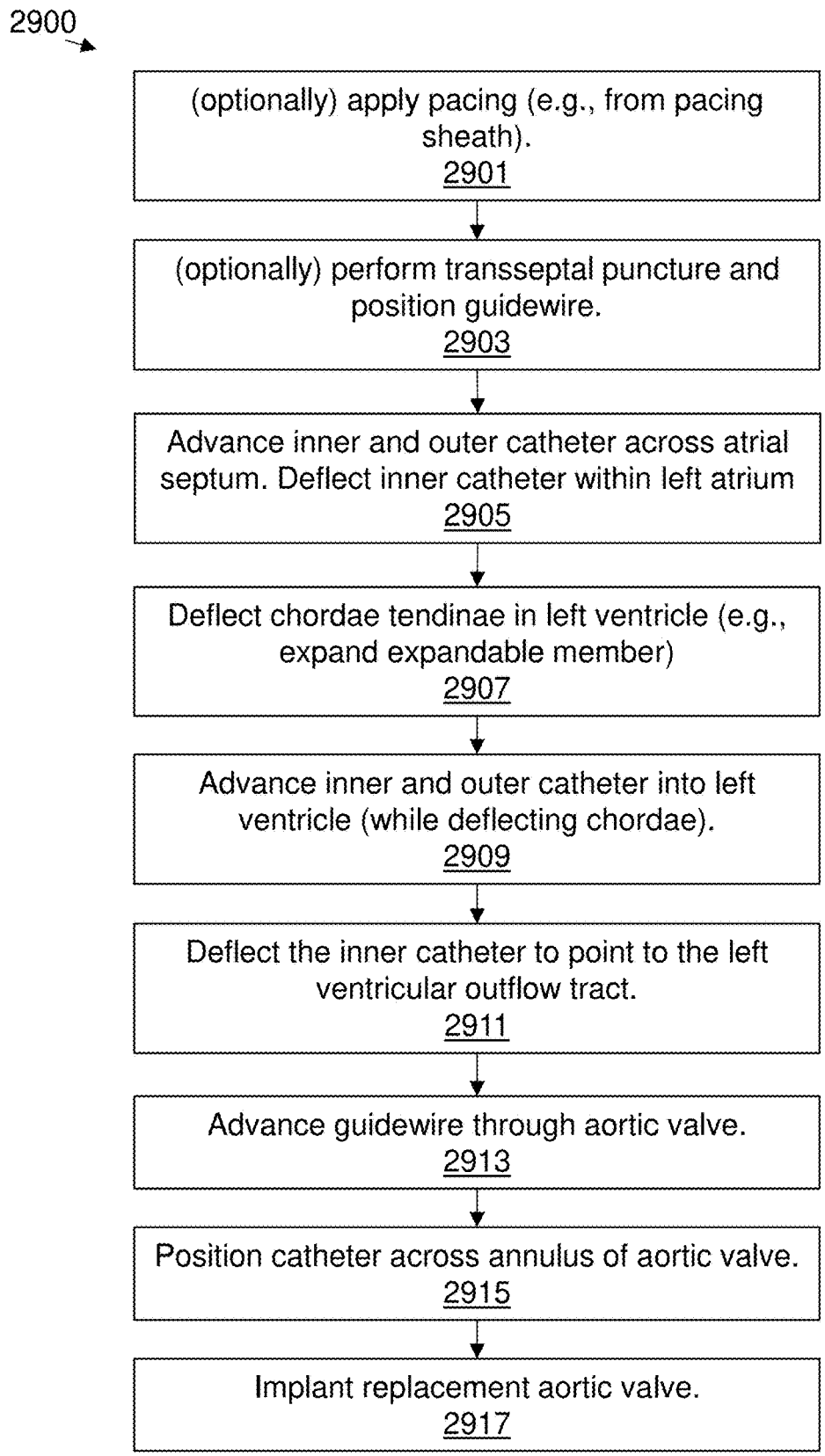
FIG. 29 illustrates one example of a method of replacing a valve as described herein.

FIG. 29 illustrates one example of a method of replacing a heart valve using an expandable deflector. In general, the expandable deflector may be used for any step of the procedure in which the apparatus is maneuvering within the ventricle. In FIG. 29, the procedure may be performed while applying a pacing signal to the heart in order to create a paced rhythm 2901. In any of the methods described herein this may be performed using an outer catheter configured as a pacing sheath, as will be described in greater detail below.

The method 2900 may optionally include performing a transseptal puncture 2903. As mentioned above, a TAVR apparatus may position a guidewire in the heart. For example, the TAVR apparatus may introduce the guidewire percutaneously into a vein or an artery, such as a femoral vein or artery, although the use of other arteries or veins is possible. In some examples, a transseptal puncture may be performed with a radio-frequency device. The TAVR apparatus may be advanced through the atrial septum and positioned within the left atrium of the heart. The inner and outer catheters may be advanced across the atrial septum 2905. For example, the first interchangeable inner catheter may be coupled (locked) to the outer catheter and advanced over the guidewire using the guidewire as a monorail. In some cases, the first interchangeable inner catheter may include a dilation balloon that may be used to expand or enlarge the septal puncture. After dilation, the dilation balloon and/or the first interchangeable inner catheter may be removed. Optionally, the same inner catheter may be used. Either the same or a different inner catheter may be deflected (e.g., bent, turned, angled, etc.) within the left atrium so that that a distal end region of the inner catheter assumes a first bend. The guidewire may then be directed distally from the inner catheter and into the left ventricle.

Prior to advancing the guidewire and/or inner catheter into the ventricle, the system may prepare to deflect away from the chordae tendinea by expanding an expandable deflector 2907. As shown in FIG. 27A or 28A the expandable deflector may be expanded (e.g., by inflating the balloon) at the mitral orifice. The expandable deflector may be on the guidewire (either straight or J-tip guidewire) and/or it may be on the distal portion of the inner catheter. In some examples the inner catheter (or the inner catheter and guidewire) may be advanced into the ventricle so that the expandable deflector is advanced first 2909; as mentioned above, the expanded expandable deflector may be advanced into the ventricle, e.g., towards the ventricular apex, by the flow of blood.

Thus, the inner (and outer) catheter may be advanced into the left ventricle 2909 while deflecting away from the chordae tendinae. In some examples, a second interchangeable inner catheter may be inserted and locked within the outer catheter. Alternatively, the same inner catheter may be used (e.g. particularly where the inner catheter is steerable or deflectable to greater than 120 degrees). In this manner, the inner catheter (or a new inner catheter) and the outer catheter may be advanced into the left ventricle. Once in the left ventricle, the inner catheter (either the same inner catheter or a new inner catheter) may be deflected within the left ventricle so that the distal end region of this inner catheter assumes a second bend (typically >120 degrees) and faces the left ventricular outflow tract 2911.

The expandable deflector may be used when maneuvering within the ventricle, including steering or bending the inner catheter to face the outflow tract, and used in order to prevent entangling of the chordae. The expandable deflector may be collapsed once the path through the ventricle has been established.

A guidewire (the same or a different guidewire) may then be advanced through the aortic valve 2913. In some examples, the guidewire may be advanced through the aortic valve and into the aorta. Furthermore, in some examples, the inner catheter used in the previous step may be removed and replaced with another interchangeable inner catheter.

The catheter may then be advanced and positioned across the annulus of the aortic valve 2915. For example, the inner catheter and the outer catheter may be positioned at or near the annulus of the aortic valve (or in some examples, across the aortic valve. In some examples, the distal end of the outer catheter may be above the annulus of the aortic valve. In some other examples, the distal end of the outer catheter may be below the annulus of the aortic valve, or even left closer to the left ventricular apex.

The guidewire (or a second guidewire having a different stiffness) may be advanced out of the distal end of the inner catheter and across an aortic valve of the patient's heart. A replacement aortic valve may then be implanted 2917. In some examples, the inner catheter may be unlocked and withdrawn from the outer catheter prior to the placement and implantation of the replacement aortic valve.

Pacing Sheaths

In any of these methods a single vascular entry point may be used to do pacing. As mentioned above, any of the methods and apparatuses (e.g., systems) described herein may include an outer catheter configured as a pacing sheath that may simplify the operation of the procedure. The pacing electrodes may be part of the distal portion of a sheath that may be positioned at the left ventricular apex to allow escaped pacing or rapid pacing during valve implantation. A pacing controller may apply pacing signals to provide pacing in case there is disruption of the sinus rhythm of the heart, and to avoid the need for a pacemaker insertion. In general, an outer catheter configured as a pacing sheath (also referred to herein as a "rapid pacing sheath") may include any of the features discussed above, including in particular the distal end region for sealingly engaging with an inner catheter.

A pacing signal may be applied to the heart so that the heart may be electrically paced to ensure pacing capture and to establish periodicity and predictability of the cardiac cycle during the procedure. One or both of atrial and ventricular pacing may be applied. The pacing signal may be controlled by a pacing controller that may be part of the pacing apparatus (e.g., pacing sheath). The controller may include a signal generator and one or more processors. The pacing apparatus may be suitably coupled to the patient and configured to provide a heart pacing signal generated by the apparatus for cardiac stimulation, and also to allow rapid ventricular pacing during valve implantation.

As mentioned, the same sheath (outer catheter) may be used to insert multiple inner catheters and may be used to provide electrical pacing.

Figure 30A:
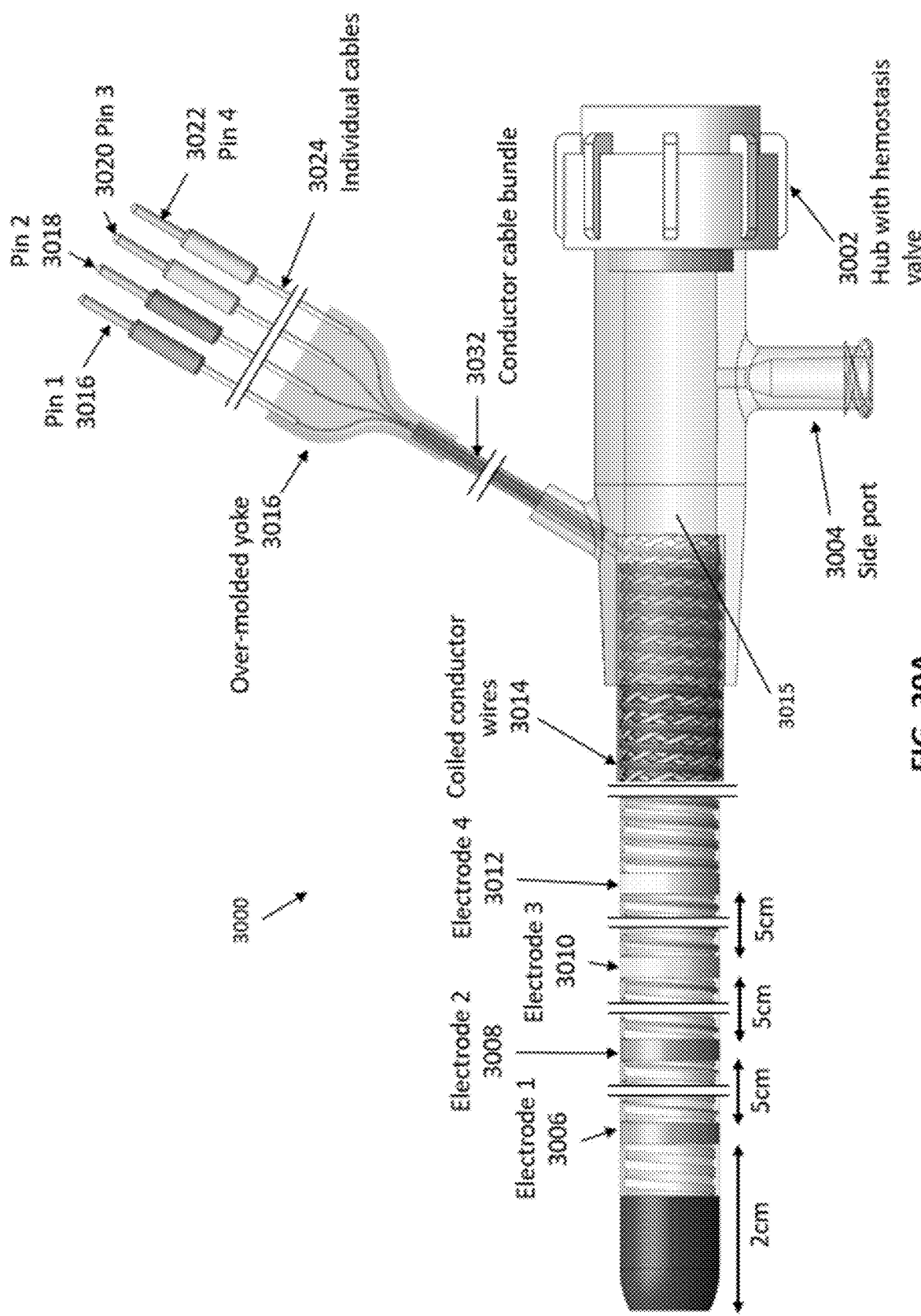
FIG. 30A illustrates one example of an outer catheter configured as a pacing sheath as described herein.

For example, FIG. 30A illustrate one example of a pacing sheath as described herein. This pacing sheath may be particularly advantageous because it may be adapted for rapid use with the retrograde systems described herein, including engaging with the catheter (e.g., one or more inner catheter) while simplifying control of pacing and performance of the valve replacement procedure. In FIG. 30A the pacing sheath 3000 has an elongate body with a proximal end having a hub and a distal end having a plurality of electrodes for applying a pacing signal to the heart (e.g., to the apex of the ventricle).

The distal end region of the pacing sheath may include a plurality of electrodes 3006, 3008, 3010, 3012 at or near the distal tip. The electrodes may be circumferential, as shown in FIG. 30A, or they may be positioned on just a portion of the circumference. The ring electrodes shown in FIG. 30A may be spaced apart by between about 1 and about 10 cm (e.g., between about 3 and 7 cm, etc.) in FIG. 30A the electrodes are separated by about 5 cm, and are spaced about 2 cm from the distal end on the elongate body. In some examples, the distal tip of the apparatus shown in FIG. 30A may be configured to lock onto the outer diameter of the inner catheter, as described above. The electrodes may each be coupled to a helical lead electrically coupling the electrodes to connectors (e.g., pins 3016, 3018, 3020, 3022) extending from a proximal end of the device. The connectors may couple to a controller (not shown), as described above. In some examples the leads may be helically wound around the elongate body to extend the length of the sheath. In the example shown in FIG. 30A the leads comprise coiled conductor wires 3014 that helically wind around the elongate body and couple to an over-molded yoke 3016 at the proximal end of the sheath. The leads (individual cables 3024) may be combined into a conductor cable bundle 3032 that is coupled to the yoke 3016 and supports the connectors (e.g., pins) for connecting to the controller. The conductive cables (e.g., wires, leads, etc.) may be bundled together and extend together helically around the length of the elongate body.

The proximal end of the sheath may also include a hub 3002 with a hemostasis valve for receiving and sealing onto the inner catheter (or multiple, nested, catheters and/or guidewire(s). The hub may also include a side port 3004 that may be used to apply and/or remove material through the central lumen 3015 of the sheath.

Figure 30B:
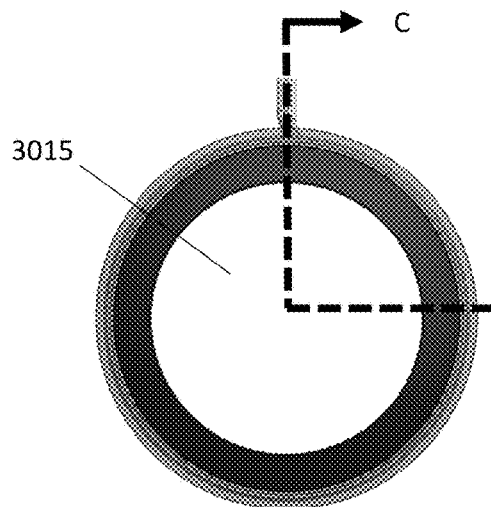
FIG. 30B shows a transverse section through a distal end region of the outer catheter (pacing sheath) of FIG. 30A.
Figure 30C:
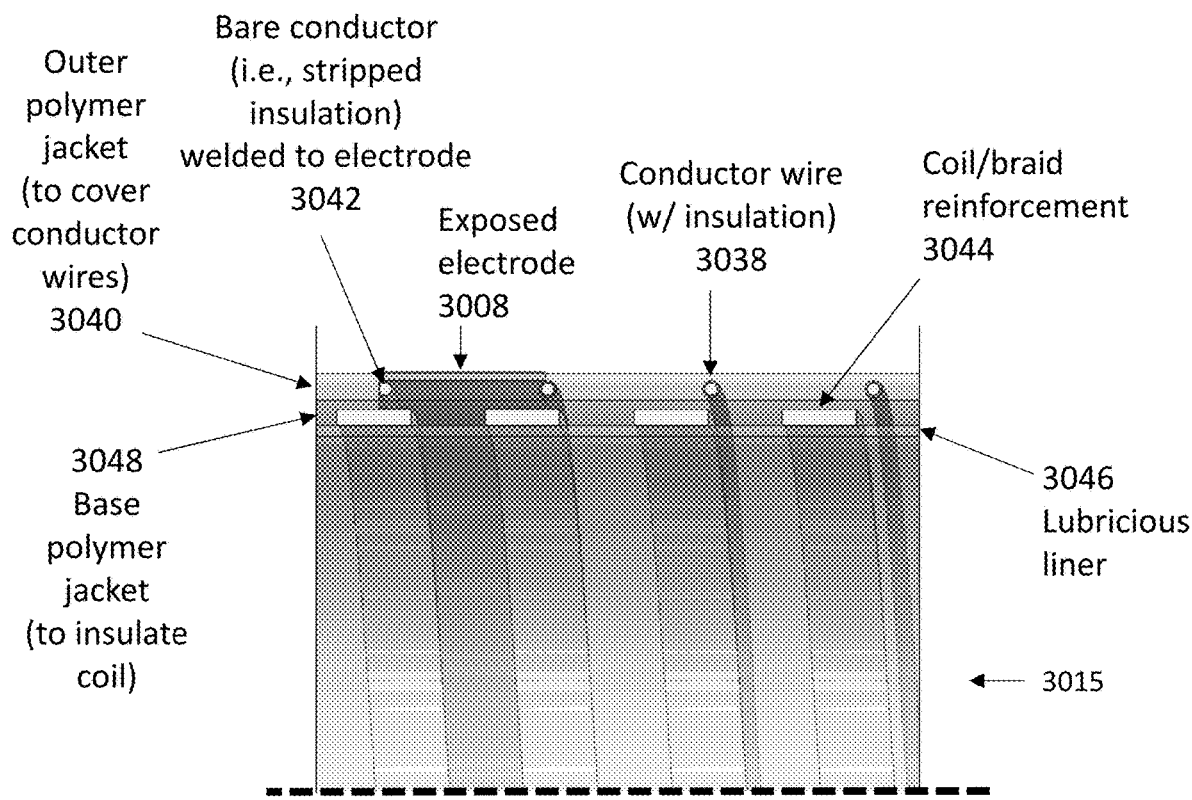
FIG. 30C shows a longitudinal section through a portion of the distal end region of the outer catheter of FIG. 30A (transverse to the section shown in FIG. 30B).

FIGS. 30B and 30C show sections through the distal end region of the sheath, illustrating one configuration of electrodes that may be used. In FIG. 30C the portion of the distal end region shown includes an exposed ring electrode 3008 that tis coupled to a conductive wire or lead 3038 that is insulated except for the exposed region 3042 in contact with the electrode. As mentioned, the conductive lead may be helically wound around the elongate body of the sheath. In this example the insulated wire is embedded and/or covered by an outer polymer jacket that covers the wires 3040.

The elongate body of the sheath may be reinforced, e.g., by a coil or braid 3044. The coil or braid may be supported by one or more layers, including being sandwiched between two or more layers. As shown in FIG. 30C, the sheath also includes an inner or base polymeric jacket 3048 that may insulate (and smooth) the inner wall of the lumen 3015 of the sheath. In some examples the sheath may also include a lubricious layer, such as a lubricious inner liner 3046. Alternatively, in some examples the base polymeric layer may be lubricious.

Figure 31:
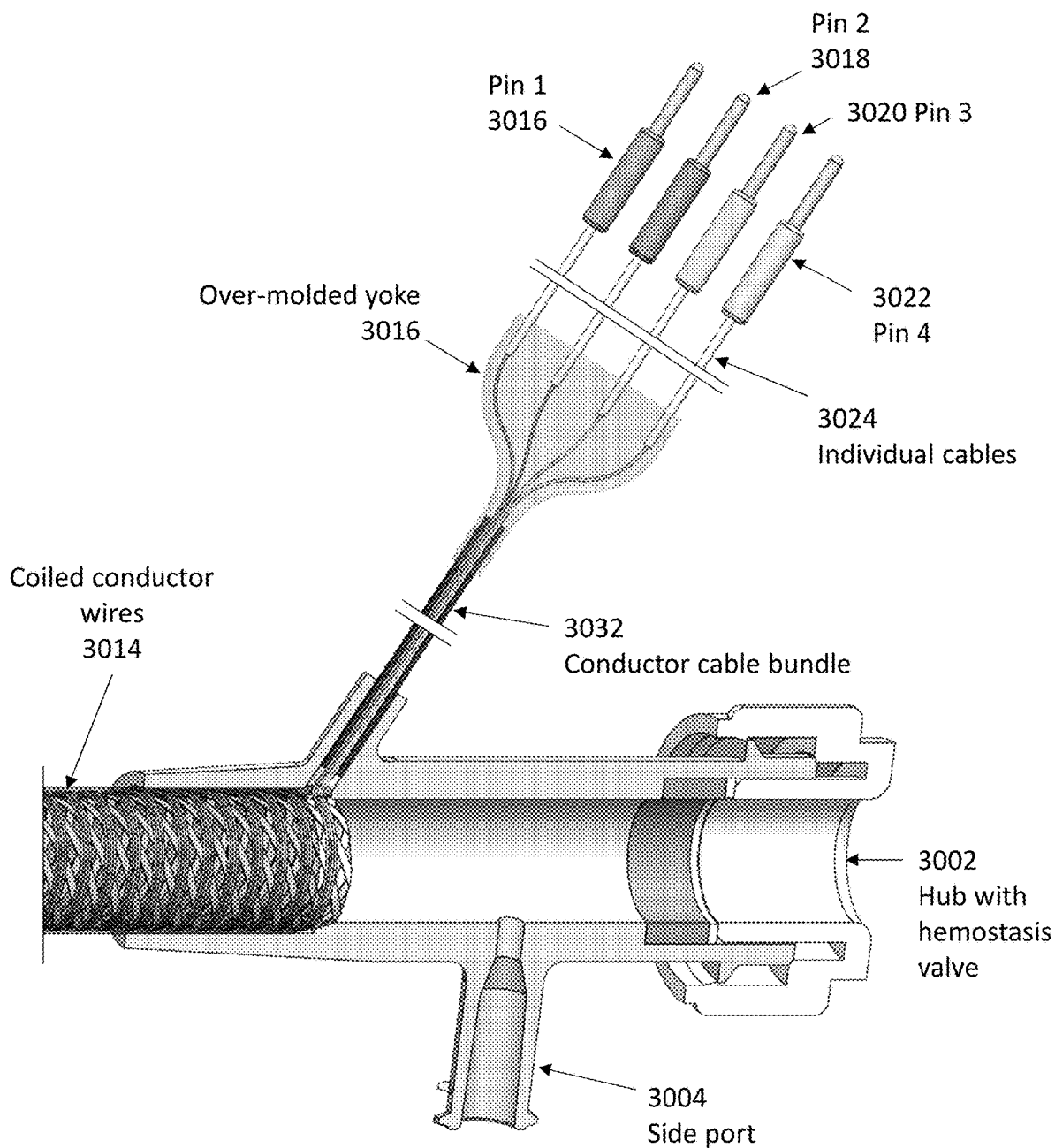
FIG. 31 is a section through the proximal region of the outer catheter of FIG. 30A.

FIG. 31 shows an enlarged view of the proximal end of the pacing sheath of FIGS. 30A-30C. The hub 3002 includes a hemostasis valve, as mentioned above, as well as a side port 3004, and a port for the bundle of conductor cables 3032. The hub may also or alternatively be configured as a handle. In FIG. 31 the conductor cables may be coupled to a yolk 3015 supporting the individual connectors (e.g., pins 3016, 3018, 3220, 3022).

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively, or in combination, the processor can be configured to combine one or more steps of one or more methods as disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system for antegrade delivery of a replacement valve, the system comprising:
   an outer catheter configured as a sheath for a catheter, the outer catheter comprising:
     an elongate body having a lumen configured to receive the catheter, and
     an engagement region within the lumen at a distal end region of the outer catheter; and
   an inner catheter comprising:
     a tapered distal end region,
     an engagement surface proximal to the tapered distal end of the inner catheter, wherein the engagement surface is configured to detachably couple to the engagement region of the outer catheter so that an outer surface of the inner catheter is flush with an outer surface of the outer catheter without a gap,
     a deflector on an outer surface of the inner catheter distal to the tapered distal end region, wherein the deflector is configured to radially expand to deflect away from chordae tendinae of the left ventricle,
     a steering region between the engagement surface and a distal end of the inner catheter that is configured to bend, and
     a guidewire lumen.

2. The system of claim 1, wherein the steering region is configured to assume a bend of greater than 120 degrees.

3. The system of claim 1, wherein the steering region comprises a wire configured to bend the steering region.

4. The system of claim 1, wherein the steering region comprises a pre-bent region.

5. The system of claim 1, wherein the steering region comprises a bend setting material.

6. The system of claim 1, wherein the inner catheter further comprises a pull wire configured to bend the steering region.

7. The system of claim 1, wherein the distal end region of the outer catheter has a tapered outer surface.

8. The system of claim 1, wherein the engagement region comprises an inner diameter that is at least one French (1 Fr.) smaller than the inner diameter of the lumen in a proximally adjacent region of the lumen.

9. The system of claim 1, wherein the engagement region comprises a coupler configured to engage with a lock ring on the engagement surface of the inner catheter.

10. The system of claim 1, wherein the tapered distal end region tapers from 3 Fr or smaller to 14 Fr or larger.

11. The system of claim 1, wherein the outer catheter comprises a thin-walled flexible outer layer of 22 Fr or larger configured to track with the inner catheter when the inner catheter is in a bent configuration.

12. The system of claim 1, wherein the steering region is between 3-6 mm from a distal tip of the inner catheter.

13. The system of claim 1, wherein the guidewire lumen comprises a rapid exchange monorail connection.

14. The system of claim 1, further comprising a guidewire.

15. The system of claim 1, wherein the inner catheter has a decreasing stiffness along the distal end region.

* * * * *